(12) United States Patent
Nambu et al.

(10) Patent No.: US 6,196,715 B1
(45) Date of Patent: Mar. 6, 2001

(54) X-RAY DIAGNOSTIC SYSTEM PREFERABLE TO TWO DIMENSIONAL X-RAY DETECTION

(75) Inventors: Kyojiro Nambu; Katsuyuki Taguchi, both of Tochigi-Ken; Satoru Oishi, Otawara, all of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/066,772

(22) Filed: Apr. 27, 1998

(30) Foreign Application Priority Data

Apr. 28, 1959 (JP) .................................................. P9-109642

(51) Int. Cl.$^7$ .................................................. G03B 42/02
(52) U.S. Cl. ........................ 378/197; 378/205; 378/98.8; 378/11
(58) Field of Search .................................... 378/197, 205, 378/98.8, 11, 14, 15, 195, 196, 20

(56) References Cited

U.S. PATENT DOCUMENTS 5,307,264 * 4/1994 Waggener et al. .............. 364/413.21
5,764,719 * 6/1998 Noettling .................................. 378/4
5,848,114 * 12/1998 Kawai et al. ............................. 378/4

FOREIGN PATENT DOCUMENTS 57-203430  12/1982 (JP) .

OTHER PUBLICATIONS

Shusuke Sone, et al., RadioGraphics, vol. 11, pp. 807 to 822, "Development of a High–Resolution Digital Tomosynthesis System and its Clinical Application", 1991.

* cited by examiner

Primary Examiner—David P. Porta
Assistant Examiner—Pamela Hobden
(74) Attorney, Agent, or Firm—Oblon, Spivak, McClelland, Maier & Neustadt, P.C.

(57) ABSTRACT

An X-ray tomosynthesis system as an X-ray diagnostic system is provided. The system comprises an X-ray generator irradiating an X-ray toward a subject, and a planar-type X-ray detector detecting the X-ray passing through the subject and outputting two dimensional imaging signals based on the detected X-ray. The system comprises a supporting/moving mechanism supporting at least one of the X-ray generator and the X-ray detector so that the at least one is moved relatively to the subject. The system also comprises an element setting a ROI position of the subject, an element for obtaining a plurality of three dimensional coordinates of pixels included in the ROI, a calculating element obtaining two dimensional coordinates of data in the two dimensional imaging signals for each of the two dimensional imaging signals detected by the X-ray detector, the data being necessary for obtaining pixel values of the three dimensional coordinates; and an element for obtaining the pixel value of each of the three dimensional coordinates by extracting the corresponding data of the two dimensional coordinates from the detected two dimensional imaging signals and adding the extracting data.

23 Claims, 63 Drawing Sheets

(ANOTER EXAMINATION)

(TOMOGRAPHY)

• FOCUS

PLANAR PLANE INCLUDING FOCUS S1 AND IN PARALLEL WITH DETECTOR

CORRECTION OF
SCATTERED-RAYS
(7.1.)

NON-LINEAR PROCESSING
FOR IMPROVED CONTRAST
(7.2.)

LOGARITHMIC
CALCULATION (7.3.)

CORRECTION OF BEAM
SPREADS/INCLINED
ANGLES (7.4.)

FILTERING PROCESSES
(7.5.)

DETECTION AND REMOVAL
OF MOVEMENT COMPONENTS
(7.6.)

CORRECTION OF
DISTORTION IN DETECTOR
INSIDE (7.7.)

REMOVAL OF STRUCTURES
OF OTHER SLICES
(7.8.)

FIG. 62B

X-RAY DIAGNOSTIC SYSTEM PREFERABLE TO TWO DIMENSIONAL X-RAY DETECTION

BACKGROUND OF THE INVENTION

1. Field of the Invention

The present invention relates to an X-ray diagnostic system, preferably to a system having a two dimensional X-ray detector, in particular, to the system which is capable of producing a tomogram at any slice only by adding projection data of a plurality of frames acquired by multiple exposures of X-rays to a subject, and the system which is capable of not only altering an X-ray incidence angle on the detector for multiple-purpose imaging but also performing imaging at arbitrary enlargement ratios using the two dimensional X-ray detector.

2. Discussion of the Background

At present, such modalities as an X-CT scanner, X-ray tomosynthesis system, magnetic resonance imaging (MRI) system, and diagnostic ultrasound apparatus have been clinically used for acquiring tomographic images of patients.

Of these X-ray tomosynthesis systems were temporarily used in the past because of relatively easier acquisition of tomograms, but advance in X-ray CT scanners and MRI systems have removed them from clinical fields. Recently, however, easy processing of images and other factors in the X-ray tomosynthesis systems have returned them to the spotlight again.

X-ray tomosynthesis systems are categorized into two types of analog and digital. The analog type of X-ray tomosynthesis uses an X-ray film as an X-ray detector, in most cases. With an X-ray tube including an X-ray focus and an X-ray film positioned face to face across a patient intervened therebetween, the tube and film are driven into their relative movement such that X-ray beams irradiated by the tube pass necessarily through an arbitrarily-set section within a subject to be imaged. As loci of the movement, various loci including a linear locus and 8-shaped curve locus can be selected. This multi-exposure of X-rays can blur image pixels in slices other than a desired slice and focus image pixels in only the desired slice, thereby providing its image.

In this analog type system, whenever slices are set, it is required that X-ray films be replaced and the X-ray tube be scanned in mutually changed movement loci. This requires troublesome handling for exchange of the X-ray films, while exposure of patients becomes large. Additionally, patients need to do their breath hold for each scan. Thus, as the number of set slices increases, variance in the breath hold becomes larger, being likely to cause phase shifts resulting in artifacts on tomograms.

To overcome the drawback, there is provided a digital type of X-ray tomosynthesis system, as is proposed by Japanese Patent Laid-open 57-203430. Like the analog type system, the digital-type tomosynthesis system is constructed such that an X-ray tube and digital X-ray detector are relatively moved in mutually opposite directions, the spatial positions of both the tube and the detector are determined, image information coming from the detector is stored in association with each position, and an image at an arbitrary slice is produced from the stored image information. This makes it possible to produce images at any slice from data acquired by only one time of X-ray scan.

As a digital X-ray detector used by the digital X-ray tomosynthesis system, there are known an imaging plate (IP), I.I.-TV unit, indirect-type planar detector having X-rays/light converting layer (such as intensifying paper, ceramic, or scintillator) and light/electric charge converting layer (such as liquid crystal such as TFT, or photodiode), direct-type planar detector converting X-rays to electric charges, or the like.

However, the above analog- and digital-type X-ray tomosynthesis systems still have some shortcomings which have not been unsolved.

First, control for moving the X-ray tube and the detector in synchronized timing is extremely difficult in terms of technical aspects. The accuracy of this synchronization control is very important to image quality of tomograms. Higher accuracy synchronization control requires more complex control mechanisms and control circuits, resulting in an increase in manufacturing costs.

Second, there is a problem of positional shifts of the X-ray tube (i.e., X-ray focus). Since the conventional tomosynthesis systems do not have particular countermeasures in this respect, such positional shifts surely causes artifacts, deteriorating image quality.

Third, there is a problem concerning movement loci made by the X-ray tube. The conventional systems do not take account of any special countermeasure, image artifacts arisen due to such movement loci may reach to unnegligible levels. For example, when a linear orbit is employed, linear artifacts tend to appear distinctly on a tomogram.

The fourth problem is about contrast resolutions. This type of X-ray tomosynthesis system basically depends on a technique by which constitution members present in slices other than an objective slice are made blurred to produce an image of the objective slice. This technique is likely to produce lowered contrast resolutions. The prior digital type systems, which do not employ any particular prevention of this influence, also suffer from the same drawback.

The fifth problem concerns enlargement ratios of images. The conventional tomosynthesis system cannot produce tomograms in which the image enlargement ratio is taken into account for each slice. Thus, for example, when coronal images etc. separately taken at a plurality of slice positions are displayed in animation, differences in enlargement ratios of images become distinct, thereby making interpretation difficult because of deteriorated visibility of lesions to be diagnosed.

As the sixth, there is a situation that acquired image data of slices have not fully been utilized, though they might have some important information still useful for diagnosis. In the case of the foregoing digital-type system, for example, although it is possible to acquire image data of, as an example, a plurality of coronal slices at one time of scanning, the acquired image data are used for only limited purposes such as displaying as-acquired images.

Still, the seventh problem is derived from a situation that the foregoing digital-type system has two limitations. One is a limitation concerning the scan orbit along which the X-ray tube and the detector should be moved in opposite directions with each other, and the other a limitation for data processing by which signals from the detector are required to be distinguishably memorized for each of the moved positions of the detector. Their limitations lead to a problem that degrees of freedom of device allocation in design but also image processing procedures decrease.

Still further, the eighth problem is that the conventional digital-type system has not provided any practical process for obtaining tomograms when both the X-ray tube and the detector are two- or three-dimensionally moved.

On the other hand, as one X-ray diagnostic system, there is known a cardiovascular X-ray diagnostic system comprising an approximately C-shaped arm which has an X-ray source and X-ray detector attached at both the ends. The C-shaped arm is formed such that it can be rotated about a axis supporting the C-shaped arm (supporting-axis rotation), slide along its C-shape guide (sliding rotation), and the like. These various rotation and translation make fluoroscopic radiography possible in different directions and at different angles.

Further, when used in the diagnosis of digestive systems, known is an X-ray diagnostic system where an X-ray tube and X-ray detector are attached to a couch capable of standing up. In this system, X-ray radiography is executed as the tube is moved along a circular-arc orbit or linear orbit parallel with the couch top, thereby providing tomograms.

However, any of the above-explained X-ray systems has limited imaging modes, because the X-ray detector is restrained by the supporting member of the C-shaped arm. For instance, a cardiovascular X-ray diagnostic system comprising a rotating arm as the supporting member is limited to radiography at a given angle or rotational radiography. These limitations decrease degrees of freedom of the system for clinical applications. For example, contrast examination of the coronary artery sometimes requires setting an imaging angle selected from a range from 55 degrees in the superior (head side) direction to 35 degrees in the inferior (feet side) direction. It is impossible for the conventional cardiovascular X-ray system to perform such deeper angle setting, because the detector hits a subject to be imaged or the table top.

SUMMARY OF THE INVENTION

The present invention is provided to solve the above unsatisfactory situations concerning the conventional systems and has the following objects.

A first object of the invention is to relieve or exclude difficulties in association with the conventional control for moving both the x-ray tube and the X-ray detector synchronously.

A second object of the invention is to prevent or suppress the generation of artifacts caused by the positional shifts of the X-ray tube (i.e., X-ray focal point) in order to raise image quality of tomograms.

A third object of the invention is to avoid an unfavorable situation where image artifacts caused depending on the movement orbit of the X-ray tube become distinct.

Still, a fourth object of the invention is to improve contrast resolutions of tomograms.

Still, a fifth object of the invention is to prevent differences in enlargement ratios from being generated for a plurality of tomograms acquired at different slice positions, upgrading display and interpretation capabilities.

Still further, a sixth object of the invention is to fully utilize image data such that, for example, image data acquired from objective slices are made into those of another slice.

Still further, a seventh object of the invention is to moderate or remove limitations on the conventional scan orbit and/or image processing procedure, increasing degrees of freedom in system design and/or image processing.

Still, an eighth object of the invention is to provide highly-functional systems enabling image data processing for obtaining the tomograms of any slice even when the X-ray tube and the detector are moved along two- or three-dimensional orbits, not one-dimensional one.

These objects can be achieved by the following construction. As one aspect, there is provided an X-ray diagnostic system comprising: an X-ray generator irradiating an X-ray toward a subject to be imaged; a planar-type X-ray detector detecting the X-ray passing through the subject and outputting two dimensional imaging signals based on the detected X-ray; a supporting/moving mechanism supporting at least one of the X-ray generator and the X-ray detector so that the at least one is moved relatively to the subject; setting means setting a ROI position of the subject; means for obtaining a plurality of three dimensional coordinates of pixels included in the ROI; and means for obtaining a pixel value of each of the three dimensional coordinates on the basis of a plurality of sets of the two dimensional imaging signals detected by the X-ray detector.

As another aspect, there is provided an X-ray diagnostic system comprising: an X-ray generator irradiating an X-ray toward a subject to be imaged; a planar-type X-ray detector detecting the X-ray passing through the subject and outputting two dimensional imaging signals based on the detected X-ray; a supporting/moving mechanism supporting at least one of the X-ray generator and the X-ray detector so that the at least one is moved relatively to the subject; setting means setting a ROI position of the subject; means for obtaining a plurality of three dimensional coordinates of pixels included in the ROI; calculating means obtaining two dimensional coordinates of data in the two dimensional imaging signals for each of the two dimensional imaging signals detected by the X-ray detector, the data being necessary for obtaining pixel values of the three dimensional coordinates; obtaining the pixel value of each of the three dimensional coordinates by extracting the corresponding data of the two dimensional coordinates from the detected two dimensional imaging signals and adding the extracting data.

It is preferred that the setting means is constructed to set a planar cross section of the subject, of which inclination to the subject is changeable. Still it is preferred that the setting means is constructed to set a curved cross section of the subject.

Still another aspect, provided is an X-ray diagnostic system comprising: an X-ray generator irradiating an X-ray toward a subject; a two dimensional X-ray detector having a curved detecting surface or curved detecting plane onto which the X-ray impinges, detecting the X-ray passing through the subject by reception at the curved detecting plane, and outputting two dimensional signals for imaging corresponding to the detected X-ray; supporting/moving mechanism movably supporting the X-ray generator and the X-ray detector; and image processing means converting the two dimensional signals detected through the curved detecting plane into two dimensional signals corresponding to planar plane.

Still another aspect, provided is an X-ray diagnostic system comprising a two dimensional X-ray detector detecting an X-ray passing through a subject to be imaged and outputting two dimensional signals for imaging corresponding to the detected X-ray; and a supporting mechanism detachably supporting the two dimensional detector.

For example, the two dimensional X-ray detector consists of a plurality of X-ray detectors whose characteristics are different from each other, and the supporting mechanism is constructed to exchangeably support the plurality of X-ray detectors.

Still, there is provided, as another aspect, an X-ray diagnostic system comprising: an X-ray generator irradiating an X-ray toward a subject to be imaged; a two dimensional X-ray detector detecting the X-ray passing through the subject and outputting two dimensional signals for imaging corresponding to the detected X-ray; a supporting/moving mechanism supporting at least one of the X-ray generator and the X-ray detector so that at least one is moved relatively to the subject; means for obtaining three dimensional volume data by obtaining a plurality of tomograms at a plurality of slice positions, on the basis of a plurality of sets of the two dimensional signals detected in different positions; and filtering means performing a filtering process on the three dimensional volume data along a radial path directed along an irradiation direction of the X-ray.

Still, another aspect is provided by an X-ray diagnostic system comprising: an X-ray generator irradiating an X-ray toward a subject to be imaged; a two dimensional X-ray detector detecting the X-ray passing through the subject and outputting two dimensional signals for imaging corresponding to the detected X-ray; a supporting/moving mechanism supporting at least one of the X-ray generator and the X-ray detector so that at least one is moved relatively to the subject; means for measuring electrocardiograph data of the subject; and means for obtaining a tomogram on the basis of a plurality of sets of the two dimensional signals detected.

Furthermore, a ninth object of the present invention is to provide an X-ray diagnostic system providing a wide range of imaging modes, such as rotational radiography, digital tomography, three-dimensional reconstruction, and enlargement imaging, only by one system, without the deterioration of resolution and an increase in calculation time.

This object can be achieved by, as one aspect, by providing an X-ray diagnostic system comprising: X-ray generating means for irradiating an X-ray toward a subject to be imaged; a planar-type X-ray detector for converting the X-ray passing the subject into an electric image signal; image processing means performing an image process on the image signal; supporting means supporting the X-ray detector; and incidence angle adjusting means being arranged between the X-ray detector and the supporting means and adjusting an incidence angle of the X-ray to the X-ray detector by rotationally driving the X-ray detector.

For example, the supporting means comprises a C-shaped arm of which one end supports the X-ray generating means and of which other end angle-adjustably supports the X-ray detector, and an arm holder supporting the C-shaped arm slidably and rotatably, and a holder supporting mechanism rotatably supporting the arm holder.

Preferably, the image processing means is constructed to obtain an X-ray tomogram on the basis of a plurality of rectangular images. The supporting means comprises a C-shaped arm of which one end supports the X-ray generating means and of which other end angle-adjustably supports the X-ray detector, and an arm holder supporting the C-shaped arm slidably and rotatably, and a holder supporting mechanism rotatably supporting the arm holder.

It is preferred that the supporting means comprises a C-shaped arm supporting the X-ray generating means and the X-ray detector, sliding supporting means slidably and rotatably supporting the C-shaped arm, and rotatably supporting means rotatably supporting the sliding/supporting means, wherein the incidence angle adjusting means is arranged between the C-shaped arm and the X-ray detector.

It is also preferred that the image processing means is constructed to obtain a trapezoidal region based on the incidence angle and to convert data of the trapezoidal region into rectangular image data.

As another aspect, provided is an X-ray diagnostic system comprising: an X-ray generator irradiating an X-ray toward a subject to be imaged; a planar-type X-ray detector detecting the X-ray passing the subject; a C-shaped arm of which one end supports the X-ray generator and of which other end angle-adjustably supports the X-ray detector; an arm holder slidably and rotatably supporting the C-shaped arm; and a holder supporting mechanism rotatably supporting the arm holder.

According to the above construction, various modes, such as rotational radiography, digital tomography, and three dimensional reconstruction imaging, can be performed by only one X-ray diagnostic system. Still, adjusting X-ray incidence angles enables imaging at desired enlargement ratios.

Furthermore the X-ray diagnostic system provides an additional advantage. Discrete pixels in an imaging region and pixels formed in the solid X-ray detector can positionally be made to correspond to each other. Thus, without performing any non-linear conversion, acquired digital image data can be made into three dimensionally reconstructed images by only performing affine conversion processes (scaling-up, scaling-down, shift) and an addition process. As a result, resampling for non-linear processes does not need to be done, and the deterioration in MTF (spatial resolution) of images caused due to sampling pitches and/or correction processes can be prevented. Further, because resampling is not required, and neither is calculation for density values, shortening times for image processing.

BRIEF DESCRIPTION OF THE DRAWINGS

In the accompanying drawings:

FIGS. 62A to 62D are schematically shown flowcharts for procedures of imaging and data processing by and in the X-ray tomosynthesis system according to the embodiment;

PREFERRED EMBODIMENTS OF THE INVENTION

First of all, some significant technical terms used in the present invention and embodiments will now be defined as follows.

Coordinate System

Figure 1:
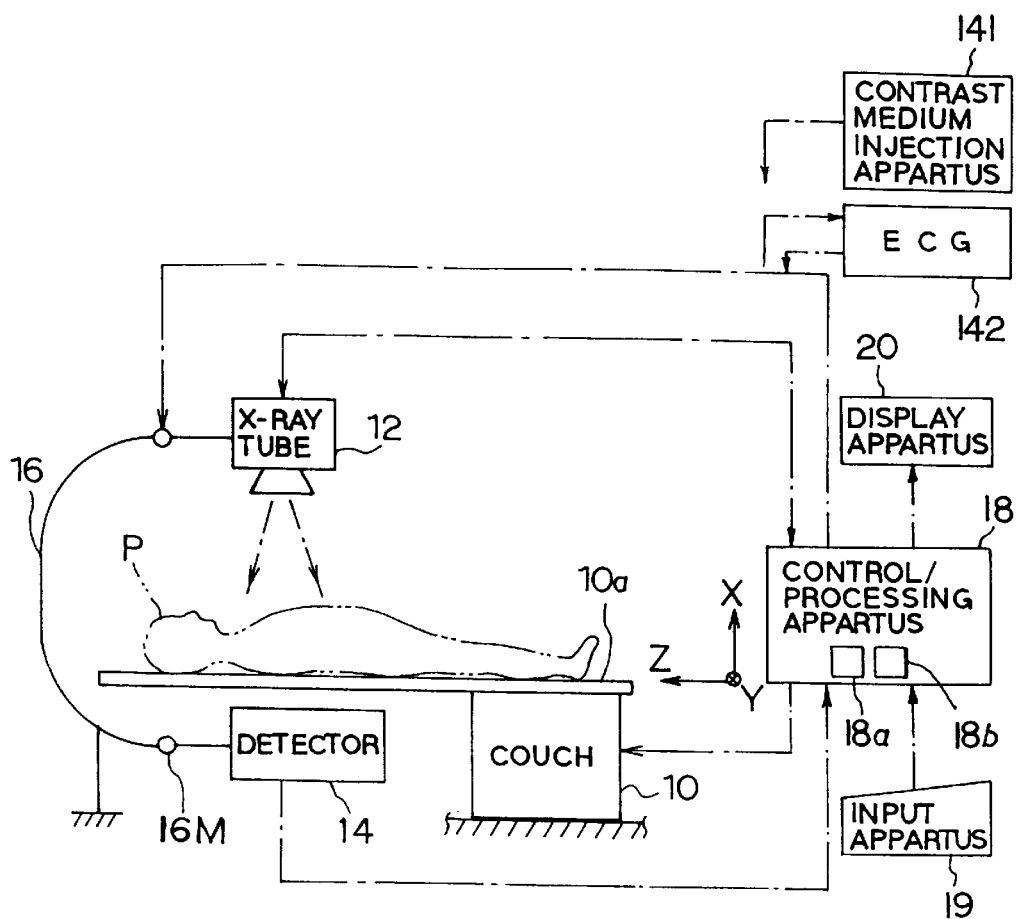
FIG. 1 is a schematic view showing an X-ray tomosynthesis system according to one example of the present invention.

For the sake of explanation, as shown in FIG. 1, a three-dimension orthogonal coordinate system is introduced where the Z-axis (normally corresponding to the body axis direction of patients) is assigned to the longitudinal direction of a tabletop of a patient couch, the Y-axis to the lateral direction of the tabletop orthogonal to the Z-axis, and X-axis to the vertical direction orthogonal to both the Z- and Y-axes.

Scan

A scan is a series of actions of X-ray irradiation and movement of an imaging system (an X-ray tube, X-ray detector, and subject to be imaged) carried out for obtaining a plurality of frames of projection data necessary for providing tomograms.

Projection Data

Projection data means a set of two-dimension projection data formed by X-ray beams transmitting through a subject in each view; the tomogram of one slice requires a plurality of frames of projection data acquired with inclusion of the same objective slice.

Slice

A slice is a cross section to be imaged of a subject.

Volume Data

Volume data are three-dimension data made up of tomographic data of a plurality of slices.

Voxel

A voxel is one pixel of a set of three-dimension data.

Image Recombination

This process broadly belongs to an image reconstruction process which has been employed in the various modalities. However, in the present invention supported by a first and second embodiments described below, a more descriptive term "recombination" is used. This recombination process is for producing slice tomograms, more specifically, is an adding process mutually adding a plurality of frames of projection data in a condition that those projection data are positionally matched frame by frame.

First Embodiment

First, features (functions and constructions) applicable to an X-ray tomosynthesis system according to the present invention will now be listed every category, and a first embodiment covering them all will then be explained. The X-ray tomosynthesis system can be constructed such that it is able to operate based on an arbitrary selected one feature or a plurality of arbitrary selected features.

The overall schematic construction of the X-ray tomosynthesis system is shown in FIG. 1.

The X-ray tomosynthesis system comprises a patient couch 10, X-ray tube 12, X-ray detector 14, supporting member 16, and control/processing apparatus 18. An input apparatus 19 and a display apparatus 20 are coupled with the control/processing apparatus 18.

The couch 10 has a tabletop 10a slidable in its longitudinal direction. On the tabletop 10a, a patient (subject to be imaged) is laid, normally, on one's back, for imaging. The X-ray tube 12 and X-ray detector 14 are arranged by the supporting member 16 so as to be faced to each other with the patient intervened therebetween. By the supporting member 16, at least the X-ray tube 12 is supported and movable three-dimensionally.

The X-ray tube 12 irradiates X-rays toward the patient P. The X-ray detector 14, which functions as X-ray detecting means, detects X-rays which have transmitted through the patient P. The control/processing apparatus 18 has memories (including an image acquisition memory 18a and three-dimension data memory 18b), a CPU and other necessary components, and is in charge of entire system control and data processing as well as production of a tomogram of any slice within a patient P. In the X-ray tomosynthesis system, there are provided a contrast medium injection apparatus 141 for injecting X-ray contrast medium into a patient and an electrocardiograph (ECG) 142 acquiring electrocardiographic signals of a patient.

The control/processing apparatus 18 functionally corresponds to driving means, part of X-ray detecting means, positional relation detecting means, image processing means, storing means, and positioning means of the invention. Moreover, these means functionally constitute various means for control and operation described later.

Figure 2:
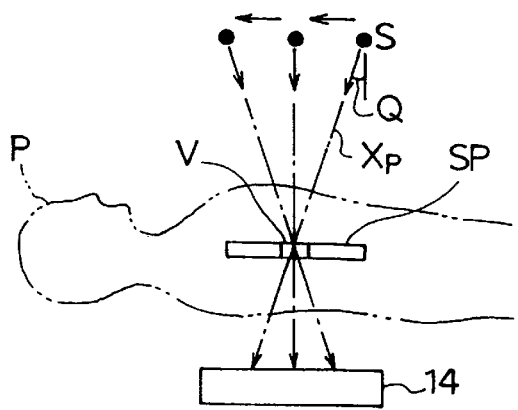
FIG. 2 shows the imaging principle of the present invention.

The imaging principle adopted in the X-ray tomosynthesis system according to the present invention will now be explained with reference to FIG. 2. As illustrated therein, it is supposed that a slice SP be set within a patient P and the slice SP is composed of a number of voxels V. Also suppose that a single X-ray path Xp coming from the focus S of the X-ray tube 12 transmits an observed one voxel V. Actual X-rays irradiated from the focus S are formed into cone-shaped beams where countless X-ray paths exist. The geometry among the X-ray tube 12, X-ray detector 14 and the patient P (specifically, the tabletop 10a) is adjusted such that the angle θ made by the X-ray path transmitting the observed one voxel V is changed view by view, and projection data are acquired at every view by the detector 14. A plurality of frames of projection data thus-acquired are positionally-shifted by amounts corresponding to changes in the geometry and then added pixel by pixel to each other. By this, only the supposed slice SP is focused and the projection data of each frame are added in turn to form image data of the slice SP, while image data of other slices become blurred.

The relative differences in blurring degrees provide tomograms of the observed slice SP.

Mechanical and electrical features of the X-ray tomosynthesis system and its embodiments will now be classified into various categories, and each feature and configuration and/or operation of the embodiment will be explained. For each feature, variations will also additionally be explained. These features, embodiments, and their variations can be combined and practiced in appropriate modes, or can solely be practiced.

As the categories of mechanical and electrical features and embodiments, there are listed: 1) system design, 2) mechanisms, 3) detector and tube, 4) scan orbits, 5) data acquisition, 6) data selection, 7) data processing prior to image recombination, 8) image recombination, 9) image processing/image cutting/correction, 10) multiple modalities, 11) entire system operation, and 12) other features, which will be described in this order.

1. System Design

Features concerning the overall system design of the X-ray tomosynthesis system includes the following items 1.1 to 1.4, which are arbitrarily selectable for practicing. In the following, the X-ray tube is sometimes abbreviated to "tube" and the X-ray detector to "detector".

1.1. Attaching Angle/position of Tube and the Detector

The X-ray tube 12 and X-ray detector 14 can be arranged in various attaching angles and positions against a patient P (i.e., tabletop 10a). In the system of the present invention, in principle, it is enough that the X-ray detector 14 can receive transmitted X-rays irradiated by the X-ray tube 12 during its movement. The detector itself may or may not be moved. A variety of examples of this arrangement are as follows.

1.1.1. Detector Side-arranged System

Figure 3:
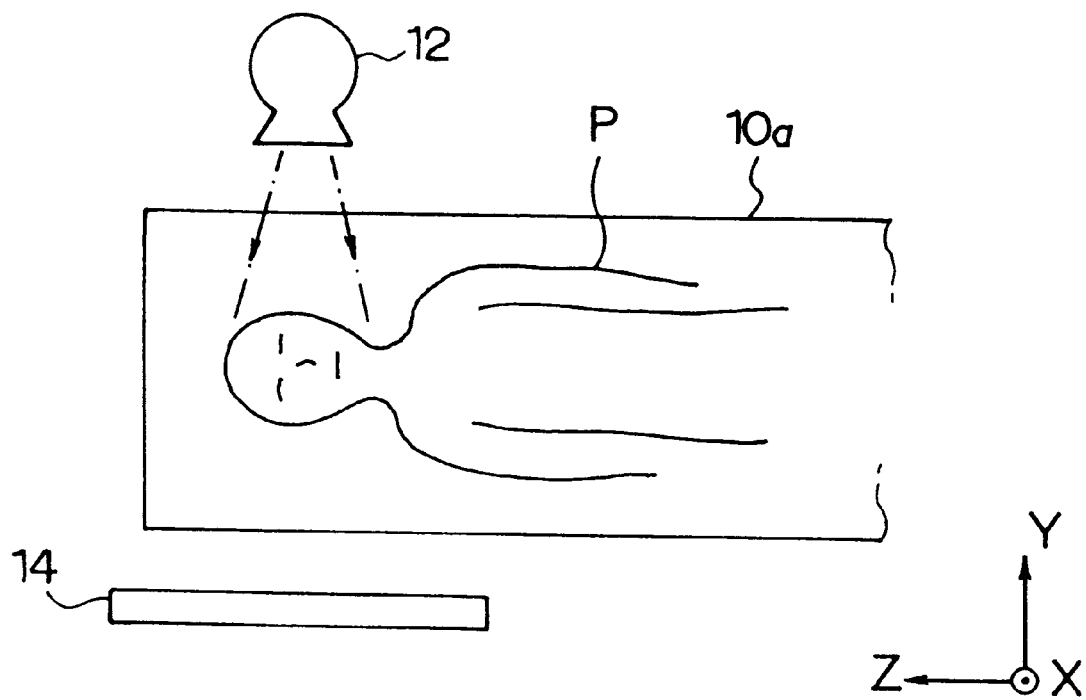
FIG. 3 shows a detector side-arranged system.

This example is concerned to a system referred to as "detector side-arranged system", where, as shown in FIG. 3, the X-ray tube 12 and the detector 14 are arranged at both lateral positions in the Y-axis direction (the right and left sides of a patient who is on one's back) with a patient intervened therebetween. Therefore, the tube 12 and the detector 14 are both oriented in parallel with the floor.

When employing the detector side-arranged system, it is advantageous in that physicians can easily access lesions of a patient from the top during operation.

As a variation, the tube 12 and the detector 14 may be arranged at oblique right and left side positions against a patient.

1.1.2. Detector Under-arranged System

Figure 4:
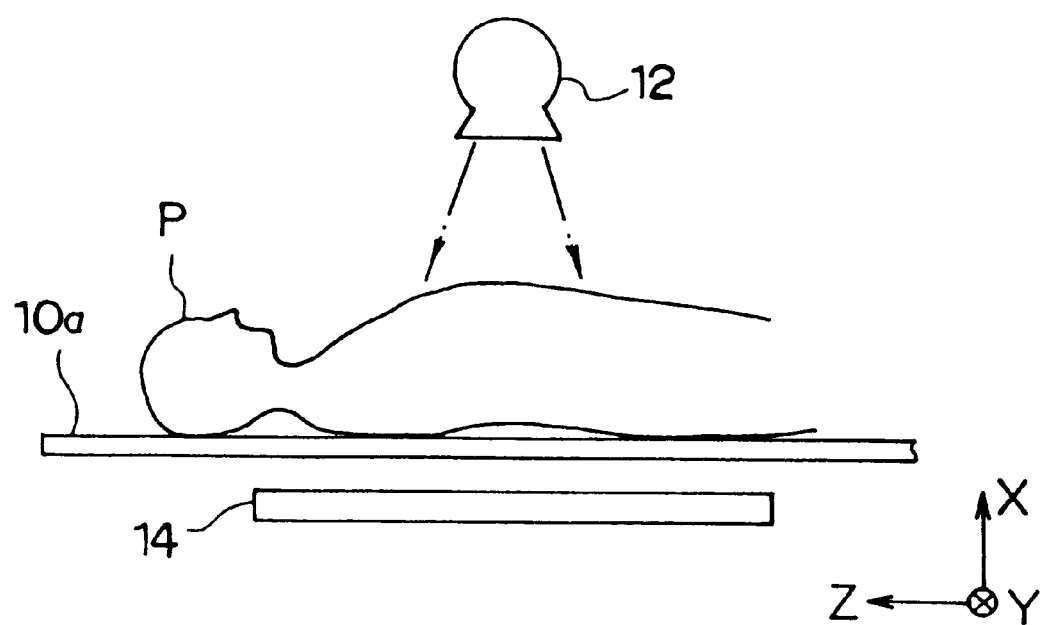
FIG. 4 shows a detector under-arranged system.

Another example is a system referred to as "detector under-arranged system". As shown in FIG. 4, in this system, the X-ray tube 12 and X-ray detector 14 are arranged face to face with a patient P intervening therebetween, and the tube 12 positions over the patient and the detector 14 positions under it, both in the X-axis direction.

1.1.3. Detector Over-arranged System

Figure 5:
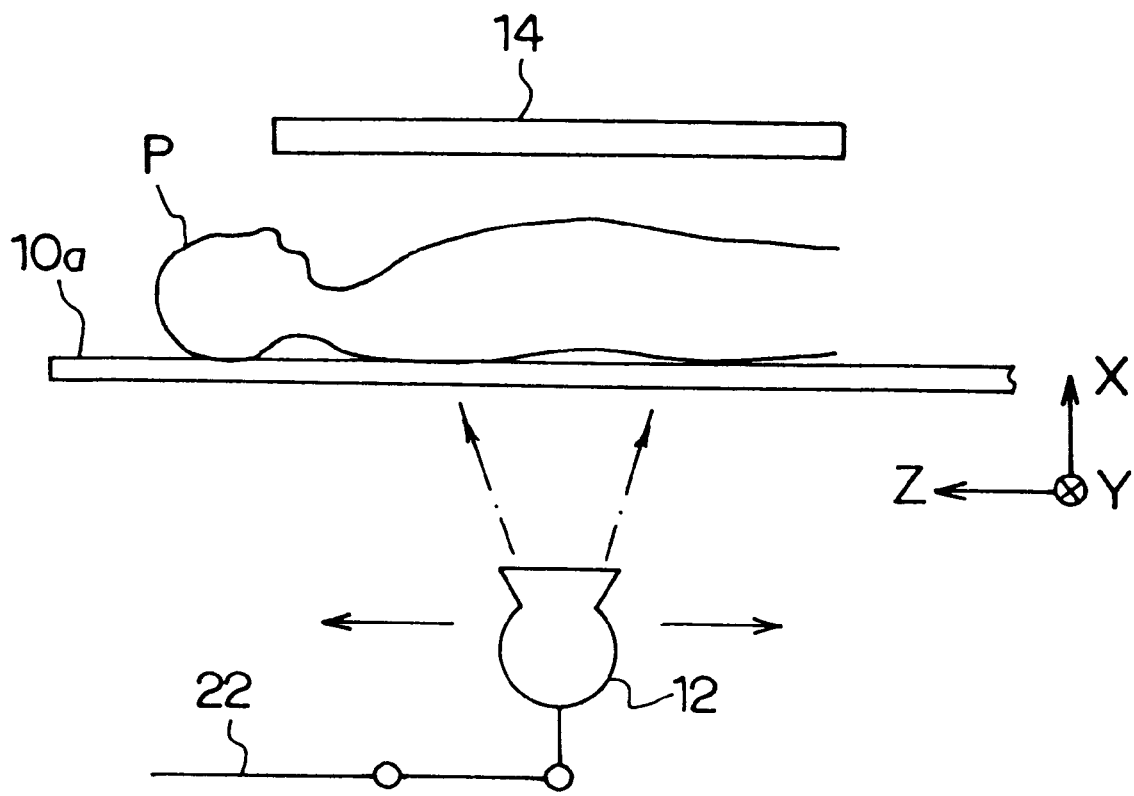
FIG. 5 shows a detector upper-arranged system.
Figure 6:
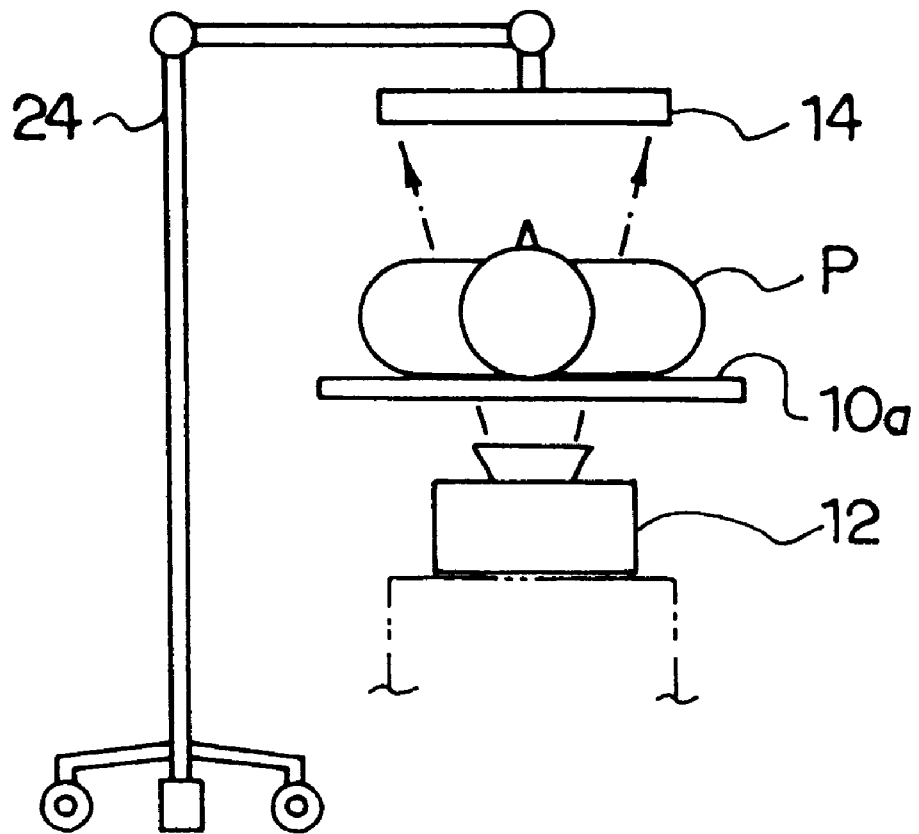
FIG. 6 also shows another detector upper-arranged system.

Another example relates to a system referred to as "detector over-arranged system". The system, as shown in FIGS. 5 and 6, has a configuration where the X-ray tube 12 and X-ray detector 14 are arranged face to face with a patient P intervening therebetween, and the tube 12 positions under the patient and the detector 14 positions over it, both in the X-axis direction. There are proposed two types of embodiments in conjunction with the detector over-arranged system, as below.

1.1.3.1. System Having Tube Moving Mechanism

In this embodiment, as shown in FIG. 5, the detector over-arranged system comprises a moving mechanism 22 capable of moving the under-arranged X-ray tube 12 within a confined space under the tabletop 10a. The tube 12 can be moved one-, two-, or three-dimensionally within the space.

1.1.3.2. System Having Portable Detector

When employing the detector over-arranged system, the detector 14 exists over a patient P, as explained above. Thus, as another embodiment for this system, the X-ray detector 14 is, for example, as shown in FIG. 6, attached to a portable apparatus 24 with casters, of which arm hangs the detector 14 from the tip, while the X-ray tube 12 is supported by a separate supporting device under the tabletop 10a. The tube 12 and the detector 14 are supported by independent supporting mechanisms, respectively. It is not necessary that the mechanism supporting the detector 14 is not always the portable apparatus 24.

Such configuration enhances convenience when setting the detector. For example, after a patient P has been laid on the tabletop 10a on one's back, the portable apparatus 24 can be moved to a lateral position of the tabletop, then the detector 14 can be set at a desired height over the patient. The detector is not in the way when a patient gets on and off the couch.

1.2. Detector-fixed System

Another feature of the system design is provided called "detector-fixed system", in which the X-ray detector 14 is fixedly supported.

1.2.1. System Where Detector is Inserted in Couch

Figure 7:
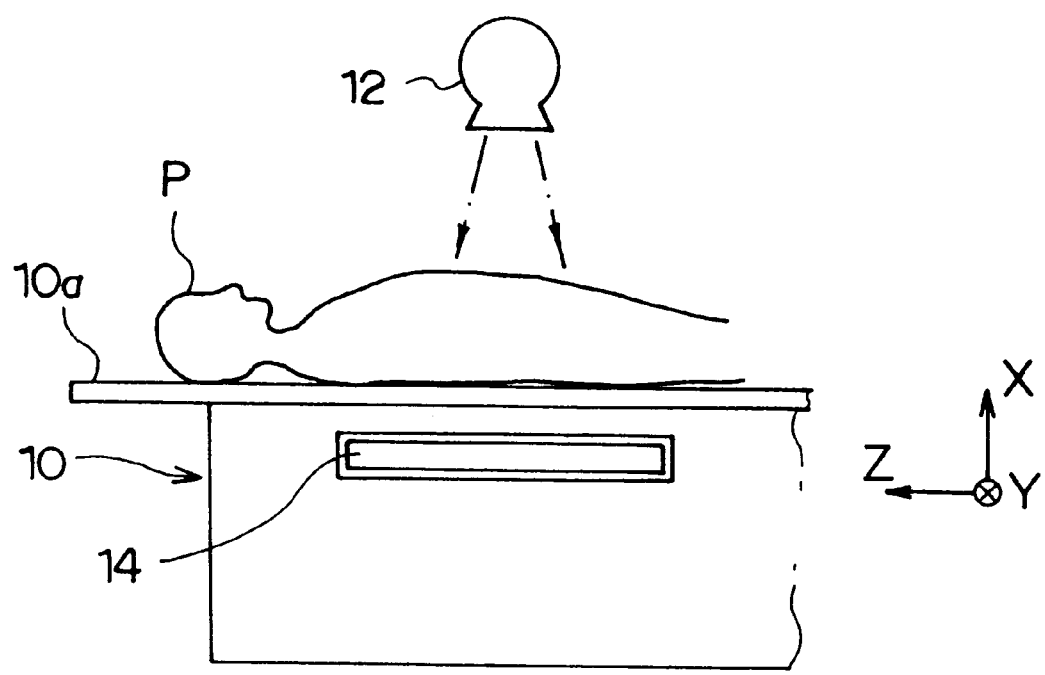
FIG. 7 illustrates a system where the detector is inserted into the couch.

One preferred example of the detector-fixed system is shown in FIG. 7, wherein the detector 14 is formed into a cassette type, and the cassette is detachably inserted into the body of the couch 10. When inserting the cassette, the X-ray detector 14 is fixedly set at a given position in the lower side of a patient P.

In cases where the same cassette is used for both conventional X-ray radiography and this inserting system, a greater convenience is provided.

1.3. Cover-attached System

Figure 8:
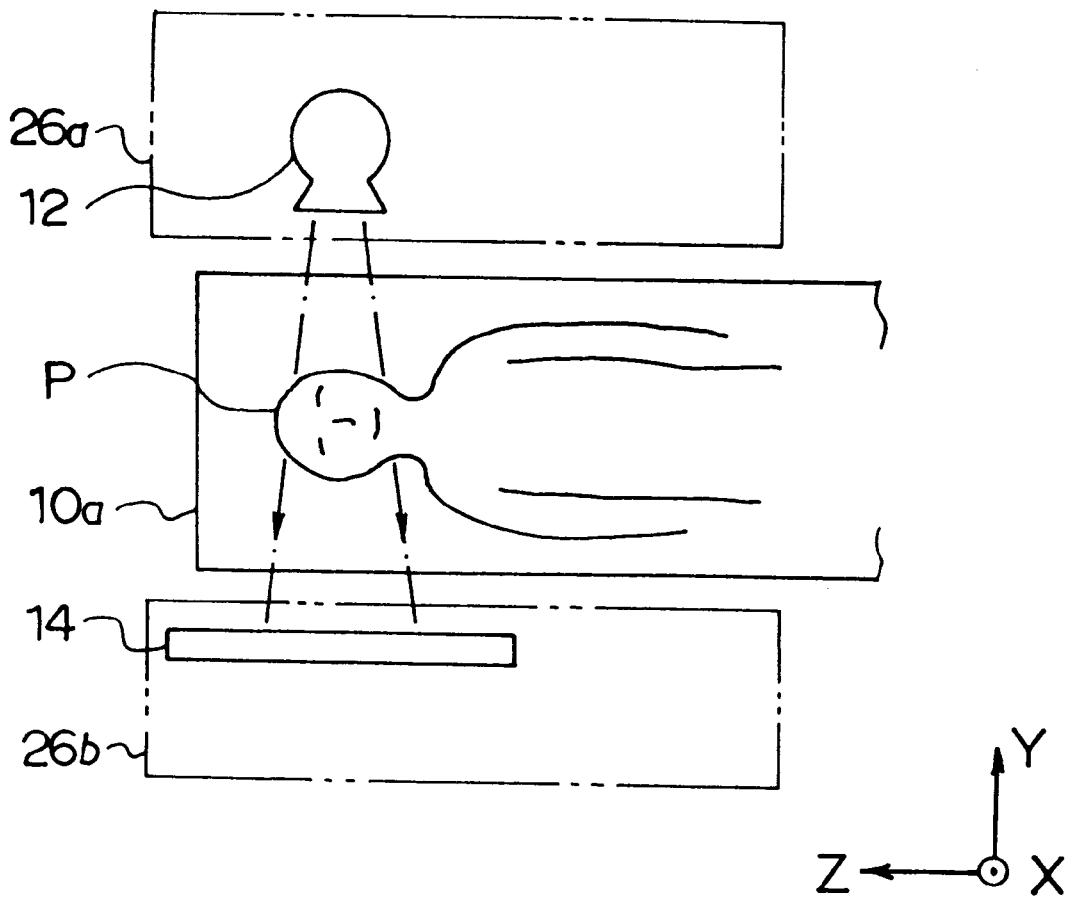
FIG. 8 illustrates a cover-attached system.

Another feature of the system design is provided by a system called "cover-attached system", wherein, as shown in FIG. 8, given spaces within which the tube 12 and the detector 14 are individually moved are shrounded by protective covers 26a and 26b. This structure prevents involving of other components when the tube and the detector are moved, while giving a patient comfort.

The cover-attached system may be used in either one of the tube 12 or detector 14 which is moved during imaging. The cover-attached system may be adopted to any of the foregoing detector side-arranged system, detector under-arranged system, and detector over-arranged system. The tube and the detector may be incorporated movably in the body member of the couch so that the body member itself functions as a protective cover.

1.4. System Moving Tabletop (Patient)

Another feature is that the tabletop 10a of the couch 10 can be slid in the Z-axis direction. In this slide motion, the X-ray tube 12 may solely be moved in asynchronism with the slide of the tabletop 10a, or both the tube 12 and the detector 14 may be moved asynchronously with each other. Still, with both the tube 12 and the detector 14 fixed, only the tabletop 10a (i.e., only patient) may be slid in the Z-axis direction for scanning, which produces relative movement of a patient to the X-ray beams.

1.5. System Allowing Detachment or Refuge of Tube/detector

Figure 9A:
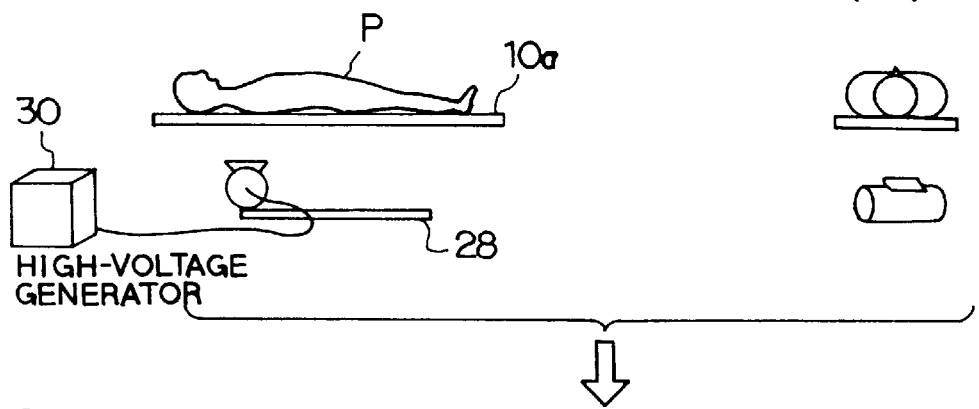
FIGS. 9A to 9C show systems allowing the detachment or refuge of the tube/detector.
Figure 9B:
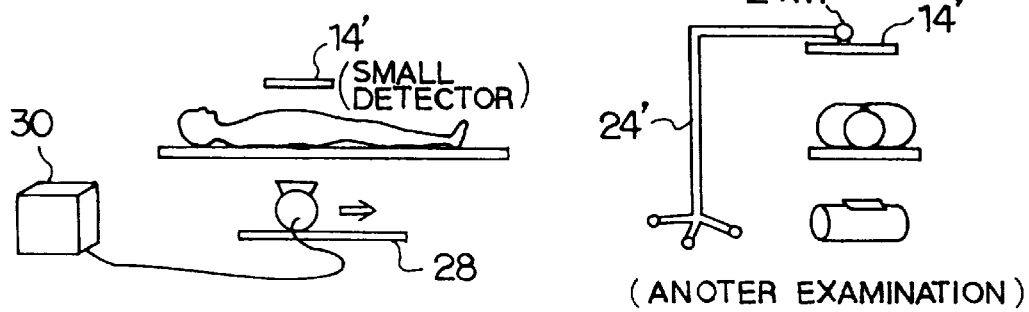
Figure 9C:
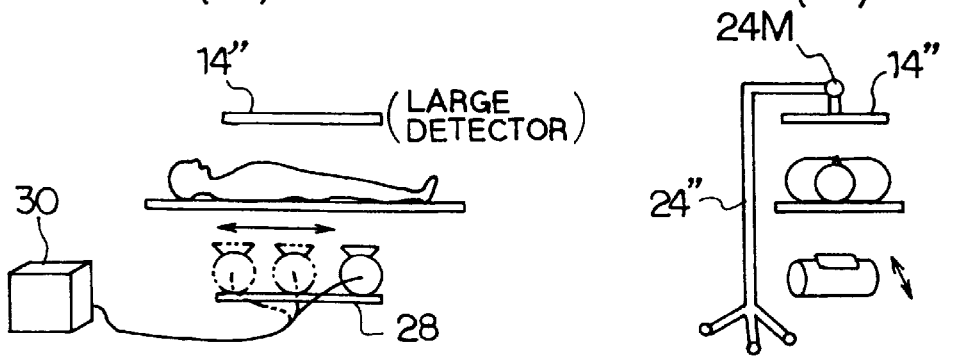

Still another feature of the system design relates to, as shown in FIGS. 9A to 9C, the detachment or refuge of the tube and/or detector. Under the tabletop 10a, a moving mechanism 28, which includes rails, motors and others, is installed to move the tube 12. By the moving mechanism 28, the tube 12 can be moved, for example, linearly along the Z-axis direction. The tube 12 is connected to a high-voltage generator 30. The moving mechanism 28 or the X-ray tube 12 is constructed to be detached or attached according to imaging types. Above a patient P laid on the tabletop 10a, the X-ray detector 14 can be set to take refuge in other appropriate positions by, for example, the foregoing portable apparatus 24. This system can responds to a plurality of imaging modes exchanged.

Additionally, the planar-type X-ray detector 14 is also detachably arranged. For example, in FIGS. 9B and 9C, a mechanical detachable unit 24M is arranged to detachably hold the detector 14. In the case of the configuration in FIG. 1, another mechanical detachable unit 16M is arranged to detachably hold the detector 14.

1.5.1. Imaging Mode Exchange (Part 1)

One of exchanging imaging modes is typically a mode of exchanges between a plain radiography mode and a tomography mode. When starting the plain radiography, the tube 12 is attached to the moving mechanism 28 (refer to FIG. 9A(a), (a')). An X-ray detector 14' attached to a portable apparatus 24' is then carried to the couch side, and the detector 14' is set at a given position above a patient P (refer to FIG. 9B(b),(b'). In this plain radiography, a detector having a higher spatial resolution is normally selected as the detector 14'. Under this installation, the plain radiography is carried out where acquisition parameters are, by way of example, a spatial resolution=0.05 mm, acquisition size= 17", and a stationary image. In a console, parameters such as a dynamic range are controlled according to the plain radiography.

After having finished the plain radiography, tomographic mode imaging will follow. In preparation, the detector 14' is taken off (or moved away) by moving the portable apparatus 24', and an X-ray detector 14' for tomography is carried to the couch side by moving a portable apparatus 24" and installed (refer to FIG. 9C(c), (c')). In this tomographic mode, the detector 14" having a large acquisition range (fast acquisition) is preferable. The tomography is carried out under acquisition parameters of, for example, a spatial resolution=0.2 mm, acquisition size=10", and acquisition range=30 frame/sec.

When returning from the tomography to the plain radiography, the opposite procedure to the above is performed.

1.5.2. Imaging Mode Exchange (Part 2)

Another typical one is a mode of exchanges carried out between an angiography mode and a tomography mode. In this exchange, fluoroscopic angiography is performed in the imaging step illustrated in FIG. 9B.

This easy detachment or refuge construction for the tube and/or detector allows other examinations to be carried out readily at the same one place before or after the tomography, providing an excellent versatility to the system.

2. Mechanism

A variety of features classified into the category of "mechanisms" of the X-ray tomosynthesis system will now be explained with reference to the drawings.

2.1. Synchronous Movement of Tube and Detector

In the present invention, by way of example, the X-ray tube 12 and X-ray detector 14 are both moved for scanning, or only the tube 12 is moved for scanning while the detector 14 is positionally fixed. When employing the former technique, it is preferred to synchronously move them. To simplify post processing of projection data of X-rays needs to know "which position" X-rays are irradiated and "which position" their transmitted data are detected. Concerning the synchronous movement of the tube and the detector, the following two examples are provided.

2.1.1. Electrical Synchronization

Figure 10:
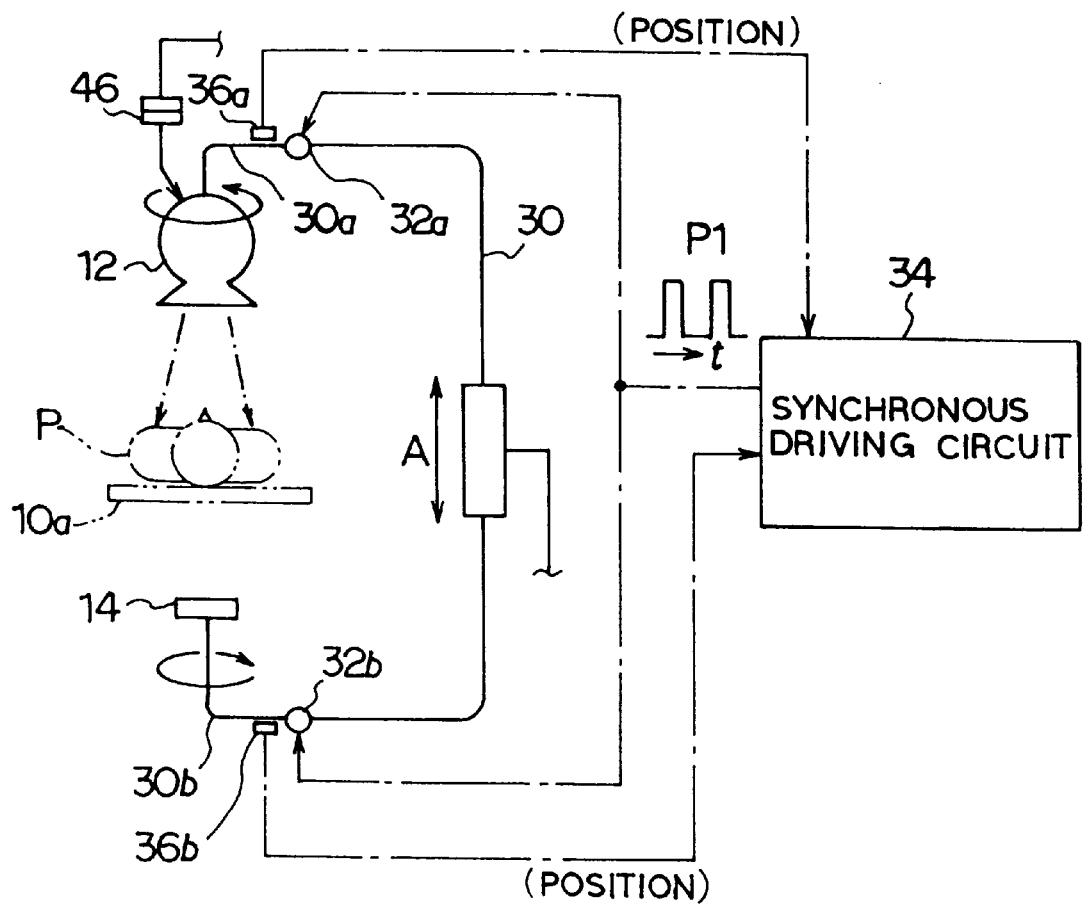
FIG. 10 represents a mechanism for electrically synchronous movement of the tube and the detector.

An embodiment provides an electrical synchronization movement technique for the tube 12 and the detector 14. As illustrated in FIG. 10, there is provided a supporting arm 30, formed by, for example, a U-shaped arm, which has moving subarms 30a and 30b at both the ends. The tube 12 and the detector 14 are attached to the moving subarms 30a and 30b, respectively. Moving mechanisms 32a and 32b intervene between the tube 12 and the detector 14 and the supporting arm 30, respectively, to perform movement of the tube and the detector. The moving mechanisms 32a and 32b have servo mechanisms, for example, to which the same driving signal P1 is supplied from a synchronous driving circuit 34. Thus, in response to the same driving signal P1, the moving mechanisms 32a and 32b synchronously move the tube 12 and the detector 14. The moving mechanisms 32a and 32b include position sensors 36a and 36b such as encoders, respectively. The position sensors 36a and 36b detect actual positions of the tube 12 and the detector 14, respectively. The detected position signals are sent to the synchronous driving circuit 34, which can determine the actual positions of the tube 12 and the detector 14 in real time.

2.1.2. Mechanical Synchronization

Figure 11:
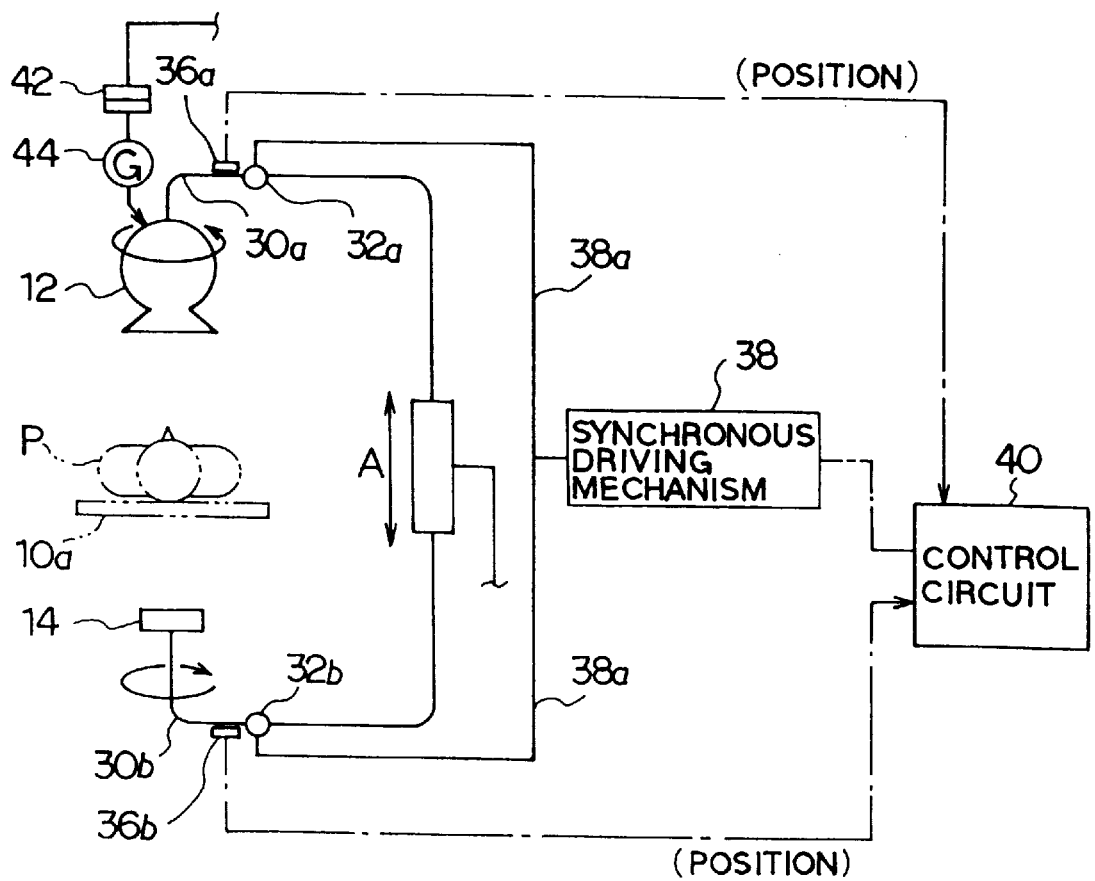
FIG. 11 also represents a mechanism for mechanically synchronous movement of the tube and the detector.

Another example is pictorially shown in FIG. 11, which provides an embodiment of mechanical synchronization. The tube 12 and the detector 14 are movably supported by a supporting arm 30 (U-shaped arm) constructed similarly to that in FIG. 10. With the moving mechanisms 32a and 32b at both the ends of the supporting arm 30, drive transferring means (axis, arm, etc.) 38a of a synchronous driving mechanism 38 are mechanically coupled. The synchronous driving mechanism 38 has such elements as motors and gears and drives respondingly to instruction signals form a control circuit 40. Hence the tube 12 and the detector 14 are mechanically driven by the synchronous driving mechanism 38, enabling their synchronous movement.

2.2. Slip-ring

Another feature of the mechanism category is use of a slip-ring. As described before, since the present invention adopts scanning during which at least the tube 12 is moved, it is desired that slip-rings be used to avoid tangles of power and signal lines. Particularly, for moving the tube 12 two- or three-dimensionally in complex orbits, it is strongly desirable.

2.2.1. Low-voltage Slip-ring

By way of example, a low-voltage slip-ring is used. As conceptually shown in FIG. 11, a low-voltage slip-ring 42 is inserted in a power line to the tube 12. Power on 100V AC is provided via the slip-ring 42 to the tube side where a generator 44 is attached to the supporting arm 30a. The generator 44 generates high-voltage power based on the low-voltage power, providing it to the tube 12.

2.2.2. High-voltage Slip-ring

A high-voltage slip-ring is another feature in the slip-ring category. In FIG. 10, a high-voltage slip-ring 46 is conceptually shown, which is inserted in a power line connected to the tube 12. High-voltage power on 120 kV DC, for example, is supplied to the tube 12 via the slip-ring 46.

Additionally, the slip-ring can be used for a C-shaped arm later described, not limited to the U-shaped arm.

2.3. Non slip-ring Structure

Figure 12:
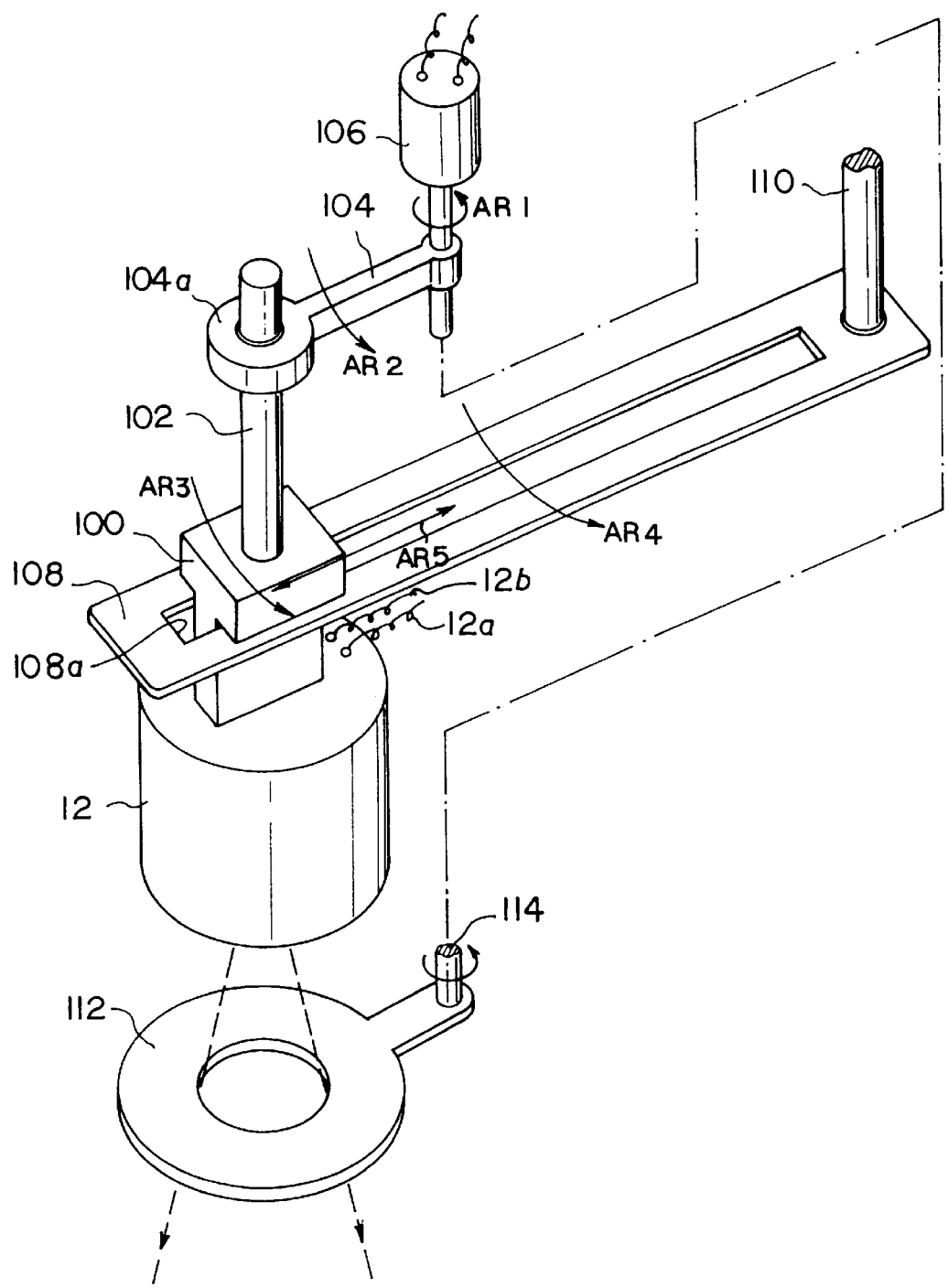
FIG. 12 is a view representing a moving mechanism with no slip-ring for the tube.

As another feature, there is provided a moving mechanism of the tube which needs not to use the foregoing slip-ring. Such an example is shown in FIGS. 12 and 13.

The moving mechanism shown in the figures is constructed such that the X-ray tube 12 (i.e., its leads 12a and 12b) permits only its reciprocating circular arch-like motions and reciprocating linear motions, without performing its rotational motions. Specifically, the tube 12 is fixedly supported by a slide member 100 having lug portions at the upper end, the member 100 being fixedly supported by a supporting rod 102. The supporting rod 102 rotatably passes through a ring 164a formed at one end of an arm 104. The other end of the arm 104 is coupled with an output axis of a motor 106. Thus the rotation of the motor 106 in one direction shown an arrow AR1 permits the arm 104 to rotate in an arrow AR2 direction, driving the supporting rod 102 into the rotation in the arrow AR2 direction.

The slide member 100 is also slidably held through its lug portions with a longitudinal slit 108a formed in a strip-like supporting plate 108, of which one end is rotatably coupled with a fixing axis 110, as shown therein. The rotation of the motor 106 in the direction indicated by an arrow AR1 causes the slide member 100 to try rotation in the same direction (refer to an arrow AR 3). The arm 104 frees from the supporting rod 102, namely the slide member 100, while the supporting plate 108 can freely rotate about the supporting axis 110. As a result, the travel (rotation) of the slide member 100 allows the supporting plate 108 to rotate in an arrow AR4 direction, being transformed into a linear motion traveling along the slit 108 (refer to a straight arrow AR5). In other words, the slide member 100 only travels straight along the slot 108.

Figure 13:
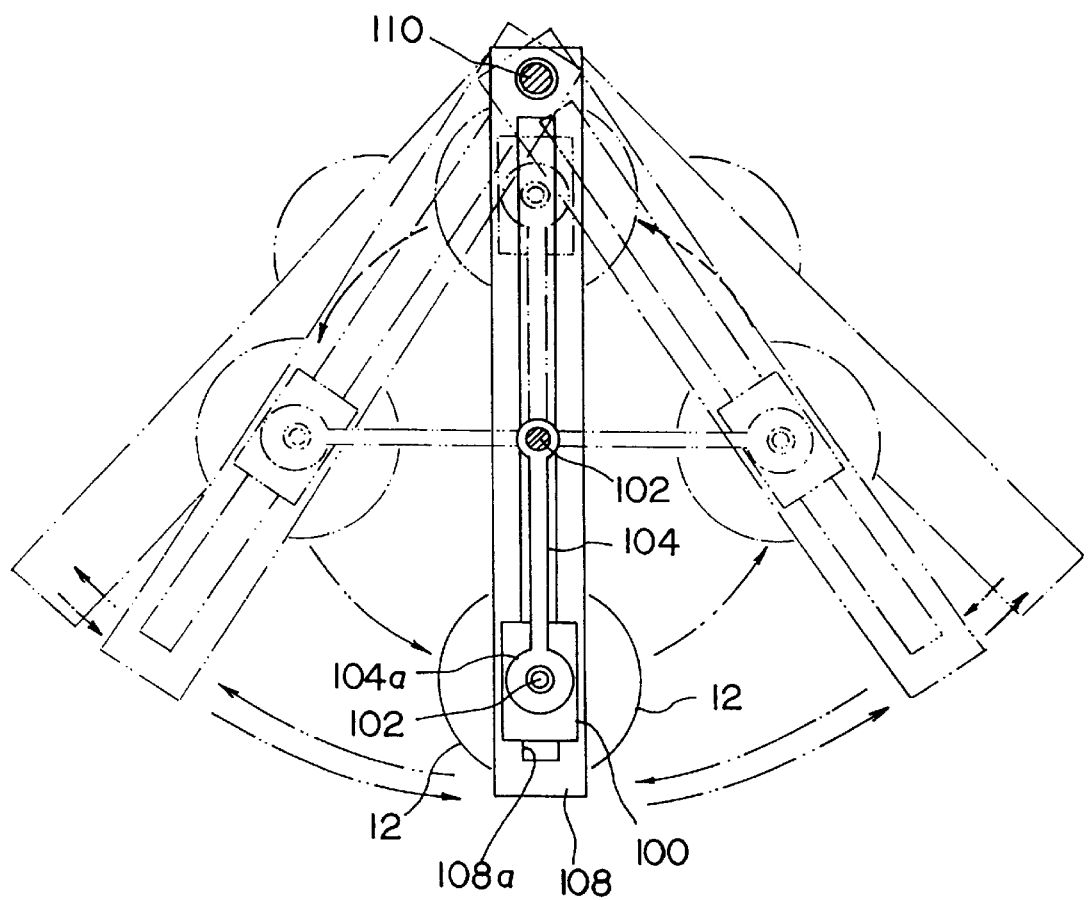
FIG. 13 is a plan view explaining the operation of the moving mechanism shown in FIG. 12.
Figure 14:
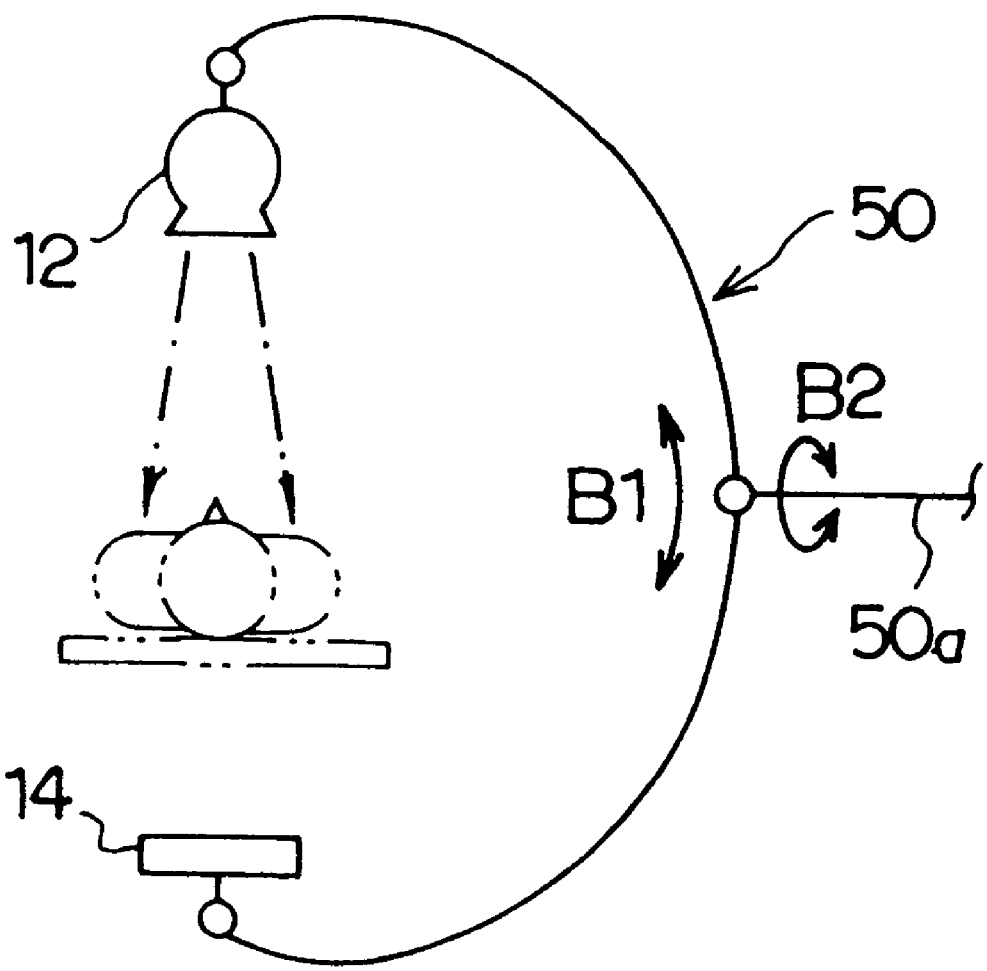
FIG. 14 illustrates the attachment of the tube and the detector to a C-shaped arm.

Thus when the motor 106 rotates continuously, the slide member 100 changes its position and orientation (corresponding to the position and orientation of the tube 12), as shown in FIG. 13. Although the tube 12 itself continuously circulates 360 degrees in association with the rotation of the motor 106, the orientation of the tube 12 changes only by an angular amount corresponding to a circular arch-like opening produced by the supporting plate 108. The circular arch-like moved distance can be absorbed by factors such as the flexibility of the leads 12a and 12b, which eliminates the need for using in the leads 12a and 12b.

Under the X-ray tube 12, set is an X-ray collimator 112 having a supporting rod 114 mechanically coupled with the output shaft of the motor 106 by way of a not-shown C-shaped arm, for example. This coupling allows the tube 12 and collimator 112 to move synchronously with each other, so that X-ray beams irradiated from the tube 12 can always be adequately collimated by the collimator 112.

2.4. U-shaped Arm

Another feature of the mechanism category is use of a U-shaped arm. As shown in FIGS. 10 and 11 described before, the U-shaped arm has a length-adjustable arm pillar (refer to an arrow A in the figures). Controlling the length of the arm pillar enables a free control of enlargement ratios of images within a given range.

2.5. C-shaped Arm

Still another feature classified into the mechanism category is use of a C-shaped arm.

2.5.1. Direct Attachment to C-shaped Arm

As one embodiment of the C-shaped arm, there is provided a construction conceptually shown in 14. To both ends of a conventionally known C-shaped arm 50, the tube 12 and the detector 14 are each attached. The C-shaped arm 50 can be slided along a curved direction made by its arm body, as shown by an arrow B1, and revolved around its supporting shaft 50a, as shown by an arrow B2, which also permit the tube 12 and the detector 14 to be moved.

2.5.2. Subsidiary Arm Extended from C-shaped Arm

Figure 15:
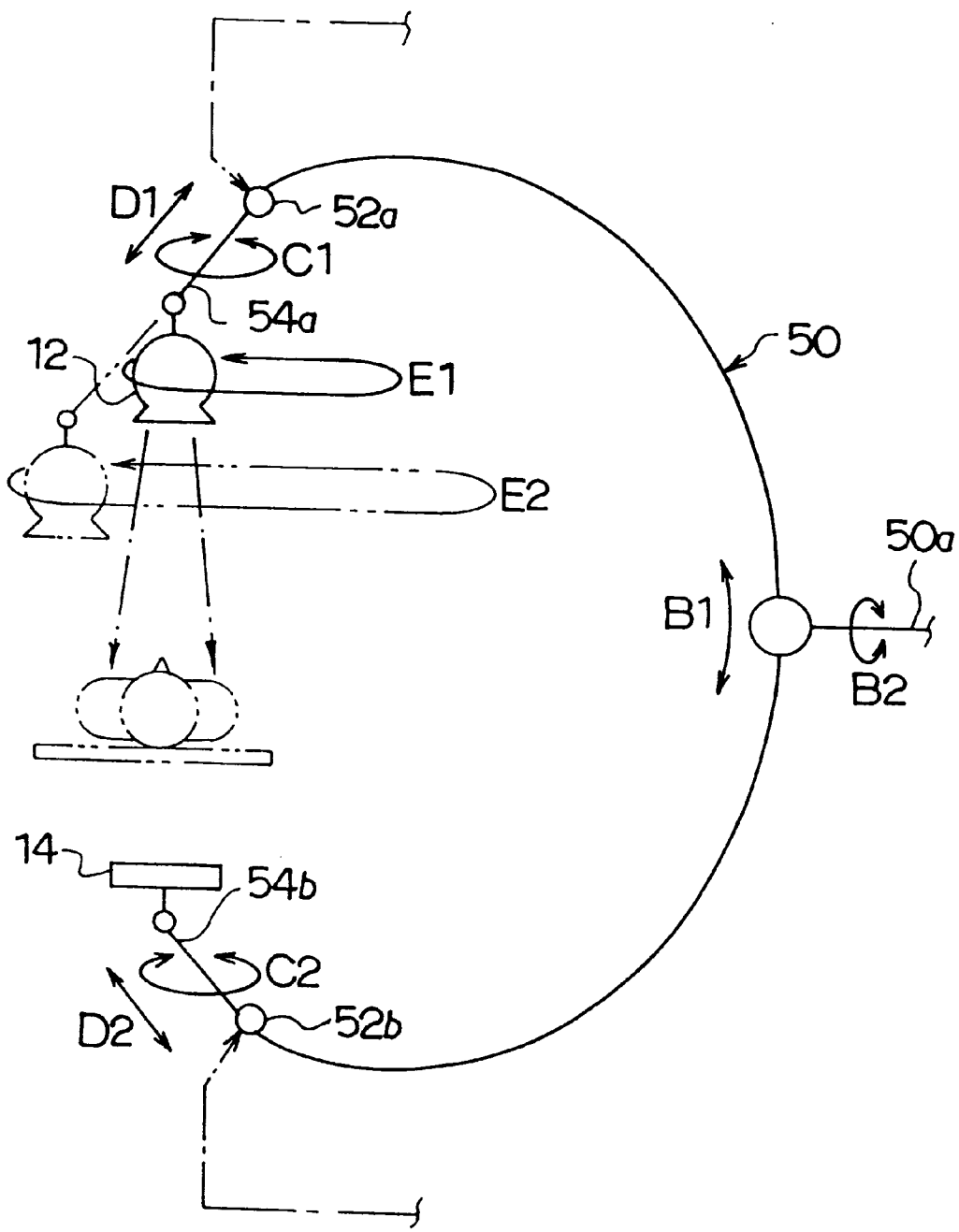
FIG. 15 illustrates the attachment of the tube and the detector using a subsidiary arm extending from the C-shaped arm.

Another example about the C-shaped arm is pictorially shown in FIG. 15, in which there is provided a C-shaped arm having moving/rotating mechanisms 52a and 52b attached to the ends, respectively. Attached individually to the moving/rotating mechanisms 52a and 52b are subsidiary arms 54a and 54b to which the tube 12 and the detector 14 are each installed. The moving/rotating mechanisms 52a and 52b receives a signal instructing of movement and/or rotation from a not-shown control circuit for a separate or synchronous drive of the tube and the detector.

Figure 16:
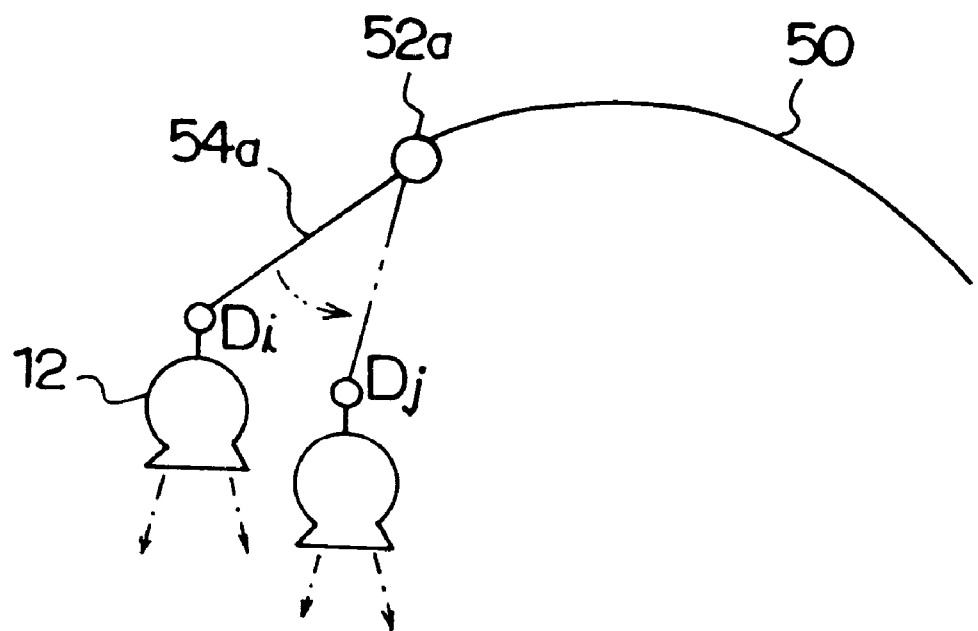
FIG. 16 explains the operation of the subsidiary arm.

Therefore, when the C-shaped arm is positionally fixed, the tube 12 and the detector 14 can be moved, like arrows C1 and C2, by moving and/or rotating the subsidiary arms 54a and 54b through the instruction to the moving/rotating mechanisms 52a and 52b. Additionally, with the movement of the subsidiary arms 54a and 54b, the movement in the curved direction of the arm body of the C-shaped arm and the revolution around the arm supporting shaft thereof (refer to the arrows B1 and B2) may be combined, raising degrees of freedom for imaging movement of the tube 12 and the detector 14. FIG. 16 exemplifies a situation; when the subsidiary arm 54a is solely changed in supporting angles from a solid line position Di to a two-dotted line position Dj, the tube 12 is changed in its traveling range, which enables control of imaging ranges, regardless of movement of the C-shaped arm itself.

In order to simplify the control of movement, the detector 14 may be fixedly supported, during which time only the tube 12 may be moved for tomography.

Further, in the supporting construction shown in FIG. 15, the detector 14 may directly be attached to the C-shaped arm, without the moving/rotating mechanism.

2.5.2.1. Adjustable Length of Subsidiary Arm

As an alternative embodiment for the subsidiary arm system, a length adjustable mechanism can be provided. For example, in FIG. 15, at least one of the moving/rotating mechanism 52a and 52b, which resides at the tube side, has an arm-length adjustable mechanism of, at least, the subsidiary arm 54a (and/or 54b) (refer to arrows P1 and P2 in FIG. 15). By this construction, the rotation radius for a rotational movement of, for example, the subsidiary arm 54a can be controlled. Thus the adjustment in only the length of the subsidiary arms leads to an easy control of imaging ranges (refer to arrows E1 and E2 in FIG. 15).

In the U-shaped and C-shaped arms thus-described, the supporting mechanisms of the tube and the detector are solely provided. Unlike the conventional analog type X-ray tomosynthesis system with which an X-ray tube is hung from the ceiling and moved along a rail thereon, such complicated and large-size installation is unnecessary.

2.6. Drive Mechanism

Drive sources of drive mechanisms driving various supporting mechanisms uses a servo-motor converting electrical control amounts to their corresponding mechanical moving amounts. However, the drive source is not limited to the servo-motor, any source can be used.

3. Detector and Tube

A category of "detector and tube" will exemplify X-ray detectors and X-ray tubes adaptable to the X-ray tomosynthesis system of the invention.

3.1. Fluorescent Plate and Read-out Means

As one example of the x-ray detectors, a detector can be used which is comprised of having a fluorescent plate converting X-rays to light and read-out means such as a sensitive camera reading out light.

3.2. I.I.

Another example of the X-ray detectors is use of I.I. (Image Intensifier).

3.3. Planar-type Detector

A planar-type detector can be used as still another example of the X-ray detector. Either of direct conversion or indirect conversion types of planar type detector may be used.

Preferably, it is recommended that the foregoing various detectors be formed into two dimensional detectors each having a large-sized, two-dimension X-ray incidence surface. When the incidence surface(plane) is large, it is possible for a positionally fixed detector to receive X-rays irradiating from all focus positions to which the tube has been moved.

It is desirable that the foregoing various detectors have built-in or added-on A/D converters, and output read X-ray transmittance data in digital quantities.

3.4. Fixed Anode Type of X-ray Tube

A fixed anode type of X-ray tube can be used as the tube. For this tube, a low-voltage slip-ring is enough when employing the slip-ring structure. In addition, this tube is small in its focus size, increasing resolution.

3.5. Rotational Anode Type of X-ray Tube

A rotational anode type of X-ray tube is also used as another example. This tube needs a high-voltage slip-ring in the case of employing a slip-ring structure.

4. Scan Orbit

Performing tomography generally requires to move both the tube and the detector, or the tube solely, during which time scanning is carried out. In the scanning, a scan orbit is referred to as an orbit along which both the tube and the detector, or the tube are moved. Though tomography may be realized by moving only the tube, both the tube and the detector are frequently moved together in order to produce larger tomography views.

The scan orbit is normally preset. In imaging operation, the movement of both the tube and the detector, or the tube are controlled based on the preset scan orbit. The scan orbit is one of the most important factors that decisive in the scan time and image quality.

4.1. Example of Scan Orbit

Figure 17A:
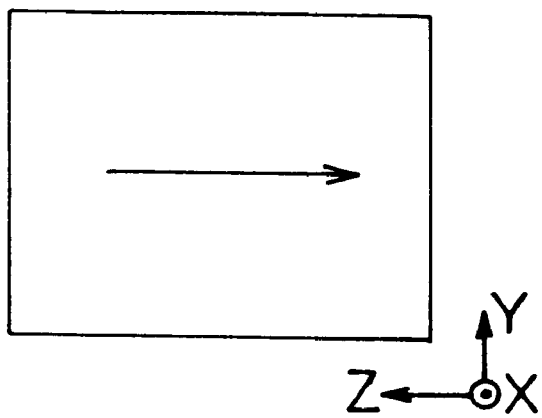
FIGS. 17A to 17C show various one dimensional orbit scans.
Figure 17B:
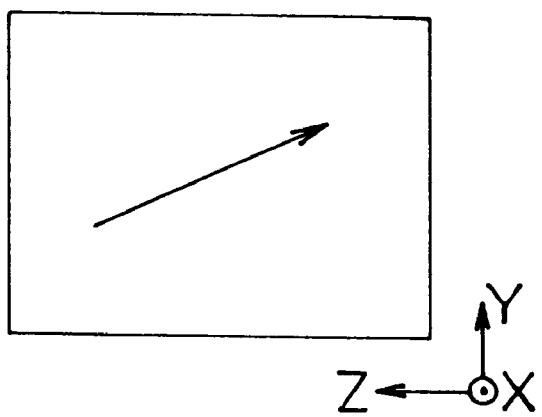
Figure 17C:
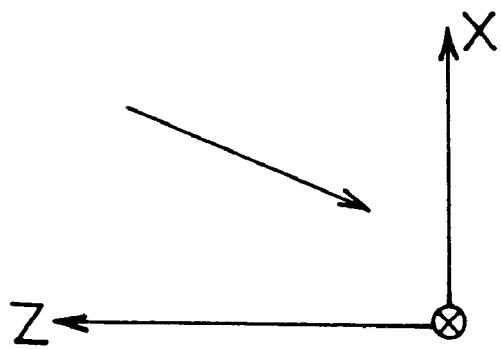
Figure 18A:
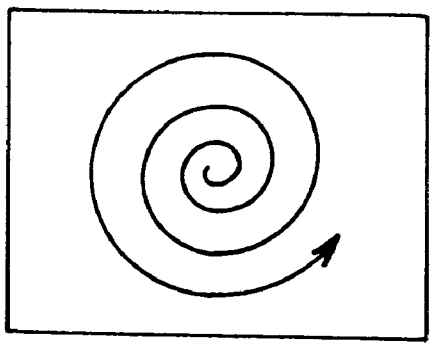
FIGS. 18A to 18C show various two dimensional orbit scans.
Figure 18B:
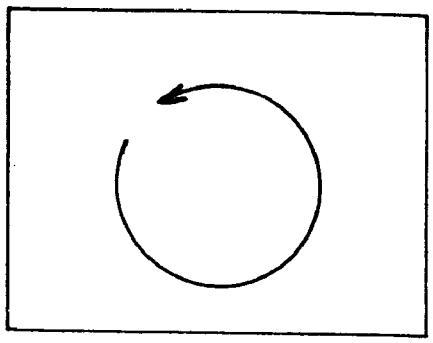
Figure 18C:
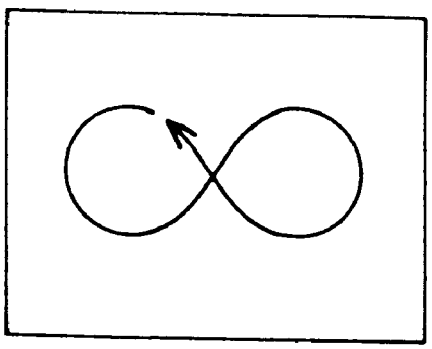
Figure 18C:
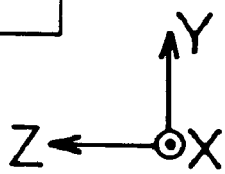
Figure 19:
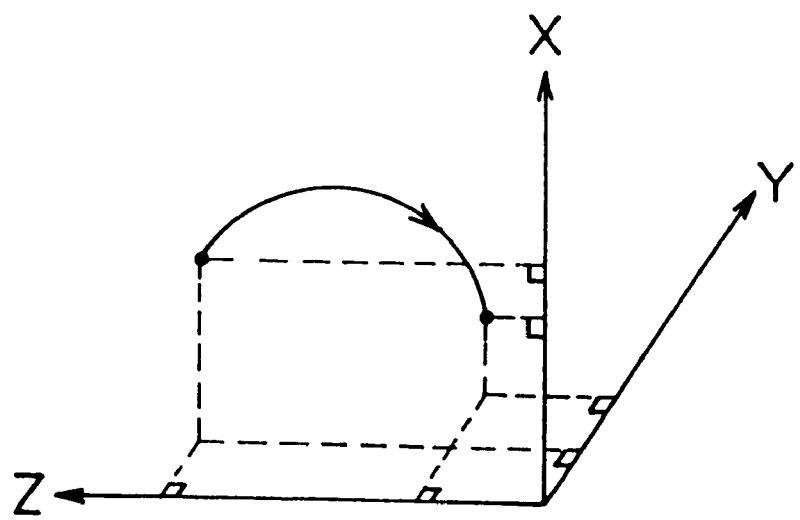
FIG. 19 shows a three dimensional scan orbit.

The scan orbit of both the tube and the detector, or that of the tube may be linear as shown in FIGS. 17A to 17C, two-dimensionally curved in the same plane as shown in FIGS. 18A to 18C, or three-dimensionally curved as shown in FIG. 19. In other words, any orbit is available.

4.2. Scan Orbit of Detector

In the case of moving the detector, it may be parallel (two or one dimensionally) moved in a coordinate, or moved three dimensionally, like circular arches. A rotational movement is available. Shortly, any orbit is acceptable for the detector.

4.3. Perpendicular Orientation of Detector to Tube

Figure 20:
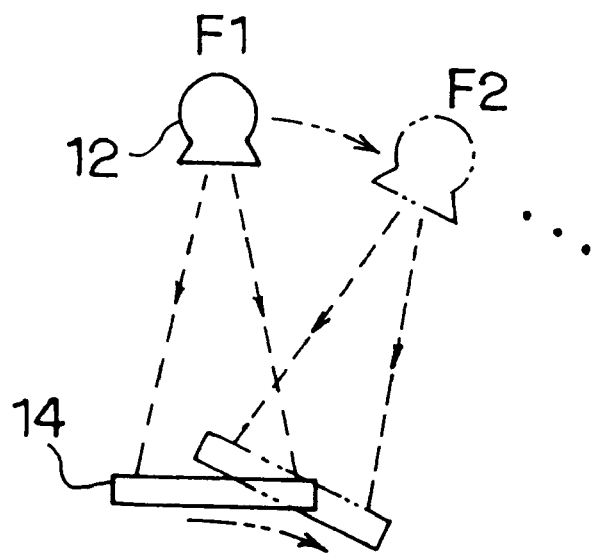
FIG. 20 represents the perpendicular orientation of the detector to the tube.

One example with regard to the scan orbit is to control the movement of the detector so that it always perpendicularly oriented to the tube (i.e., its detection surface is perpendicular to the central irradiation direction of irradiated X-rays). As shown in FIG. 20, assume that the tube 12 is moved along a circular arch-like orbit from the solid line position F1 to the two-dotted line position F2. Corresponding to this movement, the detector 14 is also moved along a circular arch-like orbit from the solid line position (in this state, the X-ray incidence surface of the detector is perpendicularly oriented to the tube) to the two-dotted line position, again providing the detector 14 the perpendicular orientation to the tube 12.

Even if the tube 12 moves, for example, along a three-dimension curve orbit, the foregoing orientation control can always sustain the perpendicular orientation relation between the X-ray incidence surface of the detector 14 and the tube 12. Unlike the conventional X-ray tomosynthesis system, a maximum view of the X-ray detector can always be utilized.

4.4. Closed-curve Scan Orbit

A closed-curve scan orbit is provided as another example of the scan orbit. For example, the scan orbits shown in FIGS. 16B and 16C are closed-curves whose start points and ends points coincide with other, respectively. Employing this kind of orbit enables a plurality of times of continuous scan, because the scan end position becomes the scan start position with no any other scan control.

Further, this closed-curve scan orbit is available for use in an intermittent scan method. By way of example, after completion of one time of scan, the scan is subject to a certain time of rest before the next scan. This scan method is preferable to a dynamic acquisition technique with contrast medium injected into blood vessels of a subject, the spread of the contrast medium being imaged.

4.5. Open-curve Scan Orbit

Another example of the scan orbit is an open-curve scan orbit, for example, as shown in FIG. 18A, where the start and end points are separated from each other. However, returning the scan position from the end point of a preset orbit to its start point every time when each scan has been completed enables the intermittent scan method, which is preferable to the dynamic acquisition scan.

4.6. Epicycle Scan Orbit

Figure 21A:
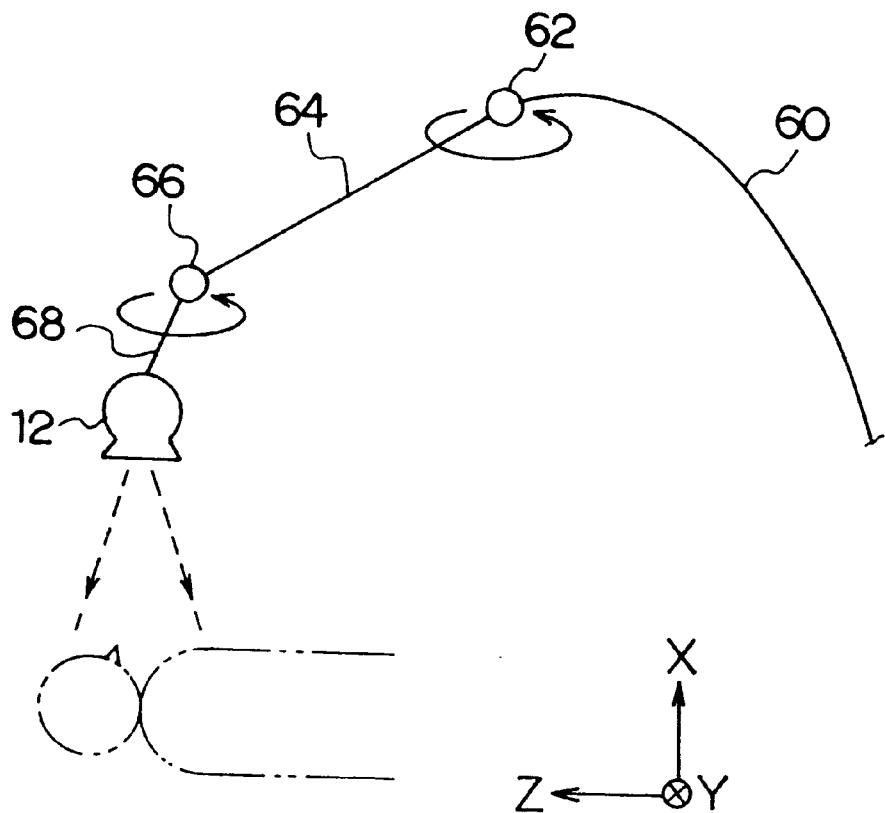
FIGS. 21A and 21B illustrate a scan orbit based on epicycle movement.

Another example of the scan orbit is provided as an epicycle scan orbit. This scan orbit resemble satellite orbits around the sun. One example to realize the epicycle scan orbit is shown in FIG. 21A, where the X-ray tube 12 is supported by two rotatable axes. A subsidiary arm 64 is supported rotatably in the Y-Z plane by a supporting arm 60 via a rotation supporting mechanism 62. A sub-subsidiary arm 68 is also supported rotatably in the Y-Z plane by the subsidiary arm 64 through another rotation supporting mechanism 66.

Figure 21B:
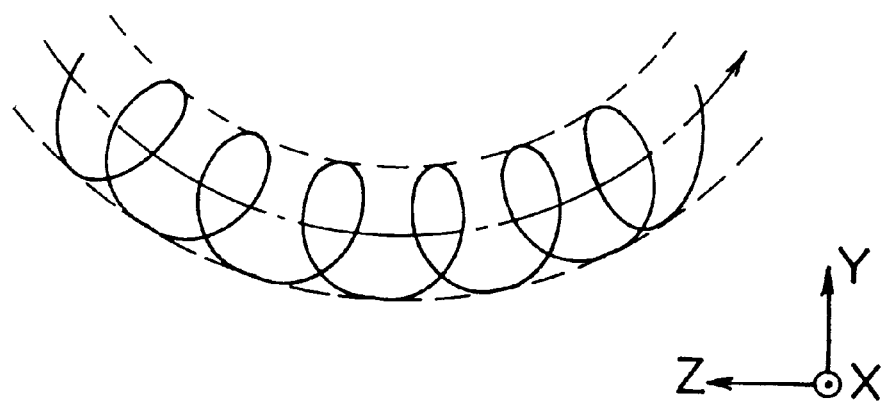

Rotating the sub-subsidiary arm 68 as making the subsidiary arm 64 rotate leads to a scan orbit based on a motion, as shown in FIG. 21B. To realize this scan orbit only requires to preset information including rotation speeds of the subsidiary and sub-subsidiary arms 64 and 68. The scan orbit based on the epicycle motion provides greater imaging regions even when the tube is moved within a limited range of smaller movement amounts, or the detector has a relatively smaller X-ray incidence surface.

4.7. Scan Orbit Shifting Imaging Views

Another example concerning the scan orbit is provided as one that gradually shifts imaging views for a plurality of scans. This scan orbit is exemplified as in FIG. 22, where the tube and the detector synchronously trace each circular orbit in the Y-Z plane, and after the completion of the circular orbits, the tube and the detector are shifted in the Z-axis direction to repeat the synchronous circular traces at another position shifted. In the same way, this circular tracing and shifting is repeated by predetermined times. To accomplish this scan orbit, it is provided, for example, in foregoing FIG. 21, only that the sub-subsidiary arm 68 be rotated, during which time the supporting arm 60 is linearly moved in an intermittent manner.

This scan method produces a plurality of circular scan orbits aligned in, for example, the Z-axis direction, which gradually shifts the imaging views along the direction. The imaging views may be shifted along any direction. Each scan may trace an orbit of any shape, such as an ellipsoidal shape, and is not limited to a circular one. It is advantageous to use this scan method when the focus orbit and the detector size are both relatively small, a plurality of scans providing a wider imaging region as a whole.

Figure 22:
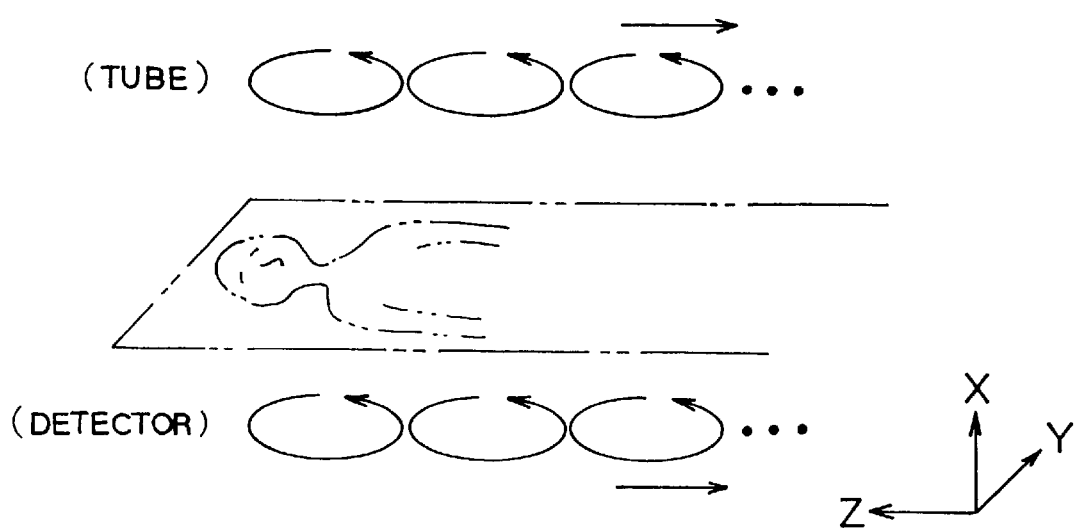
FIG. 22 illustrates scan orbits moving the imaging view.

Additionally, in FIG. 22, with the tube and the detector both rotated, they may be linearly-moved continuously. This manner provides a linear succession of circular loci.

4.8. Scan Orbit Mutually-changing Periods of Movement of Tube and Detector

Figure 23:
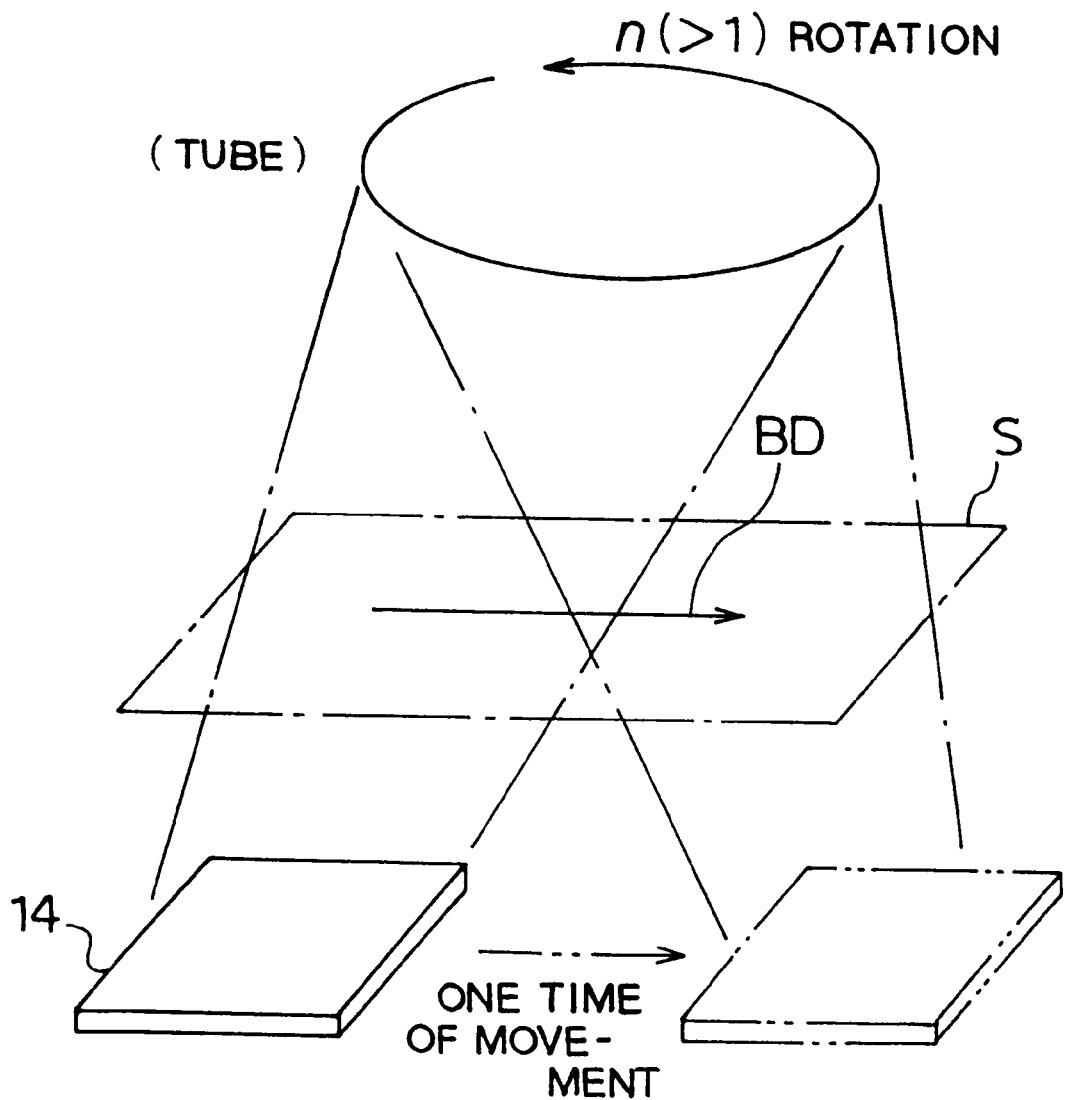
FIG. 23 exemplifies scan orbits where the moving cycles of the tube and the detector are mutually differentiated.

Still another example of the scan orbit is a scan that makes periods of movement of the tube and the detector different from each other. Such scan orbit is exemplified in FIG. 23.

In this example, the tube is consecutively rotated n-times (n>1, for example, n=10 times and each rotation period=1 sec) for providing its focus circular scan orbits, during which time the detector is linearly moved from "position a" to "position b", in the figure without rests or with rests (every specified time for example, every one sec.

This scan method causes the periods (times) of movement of the tube and the detector to be changed from each other in the same desired slice S, depending on their positions. Thus, this scan is preferable to observation of a vessel BD flowing along the slice S, making it blurred images of slices other than a objective slice.

In this scan technique, the tube may be moved to produce a scan orbit tracing an epicycle motion, and is not limited to the circular one. On the other hand the detector may trace any other scan orbit.

4.9. Scan Orbit Combining Two-axes Motion of Tube and One-axis Motion of Detector Still another example is a scan orbit formed by moving not only the tube in the two-axes 64 and 68 but also the detector in one-axis, as shown in FIG. 21A. Depending on how both the axes at the tube and sides are moved, various scan orbits are provided; for example, there is provided a scan orbit where an epicycle motion of the tube and a linear motion of the detector are combined.

4.10. Selection of Scan Orbit and Orbit Radius

As to the scan orbit, still another example relates to selection of types of scan orbits and/or their orbit radii. In conventional X-ray tomosynthesis system, types (shapes) and/or radii of scan orbits were predetermined. In contrast, as described before, the system itself according to this embodiment provides the U-shaped or C-shaped arm which supports the tube and the detector in multiple degrees of freedom, without support from the ceiling. Thus it can easily be designed that a control apparatus driving the arm previously stores data instructing of a plurality of types of scan orbits and orbit radii, and an operator selects a desired scan orbit and radius. Such a construction can provide a steady and quick scan instruction in conformity with imaging views and imaging regions.

4.11. Combination of Mechanisms of a Plurality of Scan Orbits

Another example is to arbitrarily combine mechanisms which can realize a plurality of scan orbits. For example, a supporting mechanism of a scan orbit tracing any one of the epicycle motion, circular motion and linear motion is adopted to the tube side, whereas another supporting mechanism of a scan orbit tracing the linear motion is adopted to the detector side.

4.12. Numerically Arbitrary Scan Orbit

Another example is concerned with a technique that traces a scan orbit according to an arbitrary value provided. Since the system itself has inherent tube/detector supporting mechanisms having various supporting axes for obtaining scan orbits, as explained, motions of the supporting axes can be controlled numerically to obtain a scan orbit tracing a sine wave, for example.

5. Data Acquisition

Features falling into the category of "data acquisition" of the X-ray tomosynthesis system will now be explained.

In the system, at least the tube is continuously or intermittently moved, during which time X-rays which have been irradiated by the tube are focused and transmitted through a subject and are detected by the detector, thereby X-ray projection data being acquired frame by frame for each view of irradiation. One time of scan is accomplished by repeating such process of irradiation and detection a plurality of times. As will be described later, based on the projection data having a plurality of frames obtained through one time or more of scans, an image of an arbitrary slice is recombined to provide its tomogram. If required, the scan is repeated a plurality of times.

The features about the category of "data acquisition" express a variety of inherent characteristics of scans, which will be detailed every feature.

5.1. Adjustable Resolution of I.I.

One of the features is to use an image intensifier (I.I.) as the detector. This I.I. provides adjustable resolutions through an electrical enlargement method, which permits an easy control of resolution.

5.2. Data Acquisition Matched to Scan Orbits

Figure 24A:
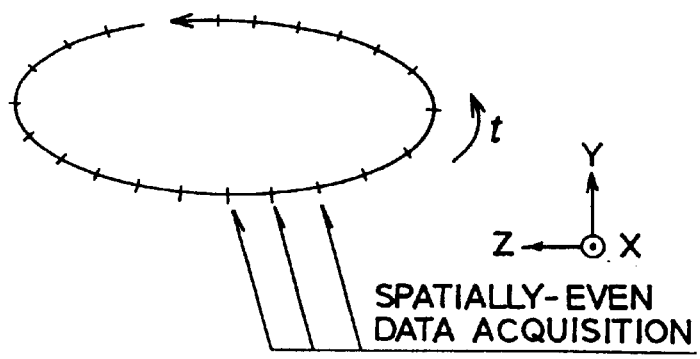
FIGS. 24A to 24C illustrated data acquisition timing control methods according to scan orbits.
Figure 24B:
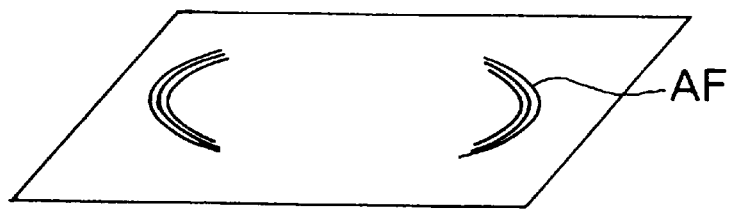

Another example is matching timing of data acquisition to shapes of scan orbits. For example, as shown in FIG. 24A, assume that both the tube and the detector employ elliptic scan orbits. In such shape of scan orbits, moving speeds on its circular arc portions having smaller curvatures tend to become slower than the remaining orbit portion. In such a case, if projection data acquisition by the detector is executed in temporally-even timing, as shown in FIG. 24A, the smaller-curvature circular arc portions are higher in spatial acquisition densities than the remaining portions. Hence, as shown in FIG. 24B, there may appear in recombined images artifacts AF resembling the shapes of the smaller-curvature circular arcs.

Figure 24C:
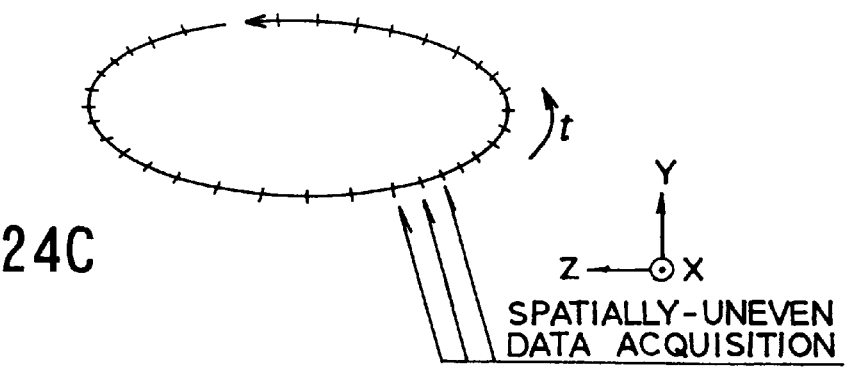

To avoid this artifacts, as shown in FIG. 24C, timing of projection data acquisition in the small-curvature circular arcs is made coarse in comparison with the remaining orbit portions. Namely the data acquisition on one orbit is carried out based on a coarse and fine timing mode matched to the shapes of scan orbits. The timing control is performed such that a control apparatus recognize the present positions of the tube and the detector on a scan orbit and adjust the acquisition timing based on the recognition results. As a result, there are provided data on spatially-even period by performing the acquisition in the temporary uneven manner.

The data acquisition timing control can also be applied to irradiation timing control for the tube, provided the tube irradiates pulsed X-rays, not limited to only the detection timing control by means of the detector.

As an alternative example, instead of controlling the data acquisition timing, moving speeds on a scan orbit can be controlled such that, for example, the larger (or smaller) the curvature, the slower (or faster) the moving speed.

5.3. Utilization of Pulsed X-rays

Another example is to set X-rays irradiated from the tube into pulsed X-rays. In this case, the detector controls the pulsed X-rays based on data detection timing.

5.4. Control of Dynamic Range Based on Projection Data

Still another example is to control the dynamic range of the detector using projection data (frame data) consisting of transmitted X-rays detected by the detector. This example includes the following two modes.

5.4.1. Control of Dynamic Range Based on Output Adjustment of Detector

By way of example, the pixel values of projection data are determined to feedback the determination results to the tube. When the pixel values overflow a dynamic range, the tube output is automatically reduced to another level to avoid the overflow.

5.4.2. Control of Dynamic Range Based on Gain Adjustment of Detector

Another example is a gain adjustment of the detector. Since the X-ray detector has an A/D converter, as explained before, the gain (sensitivity) of an integrator incorporated in the A/D converter is adjusted in accordance with the determined pixel values of projection data. For example, if the pixel values overflows the dynamic range, the gain is automatically lowered to avoid the overflow.

5.5. Utilization of Continuous X-rays

As another feature, there is provided a method of operating the tube in a continuous X-ray mode.

5.5.1. Definition of Data Acquisition Timing by Points

In a continuous X-ray mode, the tube operates to irradiates X-rays from its focus continuously in the time domain. Therefore, the detector is constructed such that it charges (integrates) transmitted X-ray energy (electric charges) during each acquisition period for frame data, and detects the charged energy at each appropriate timing point residing in each frame period. Setting the points (timing positions) is given by the following two methods.

5.5.1.1. Center-of-gravity of Acquisition Time

Figure 25:
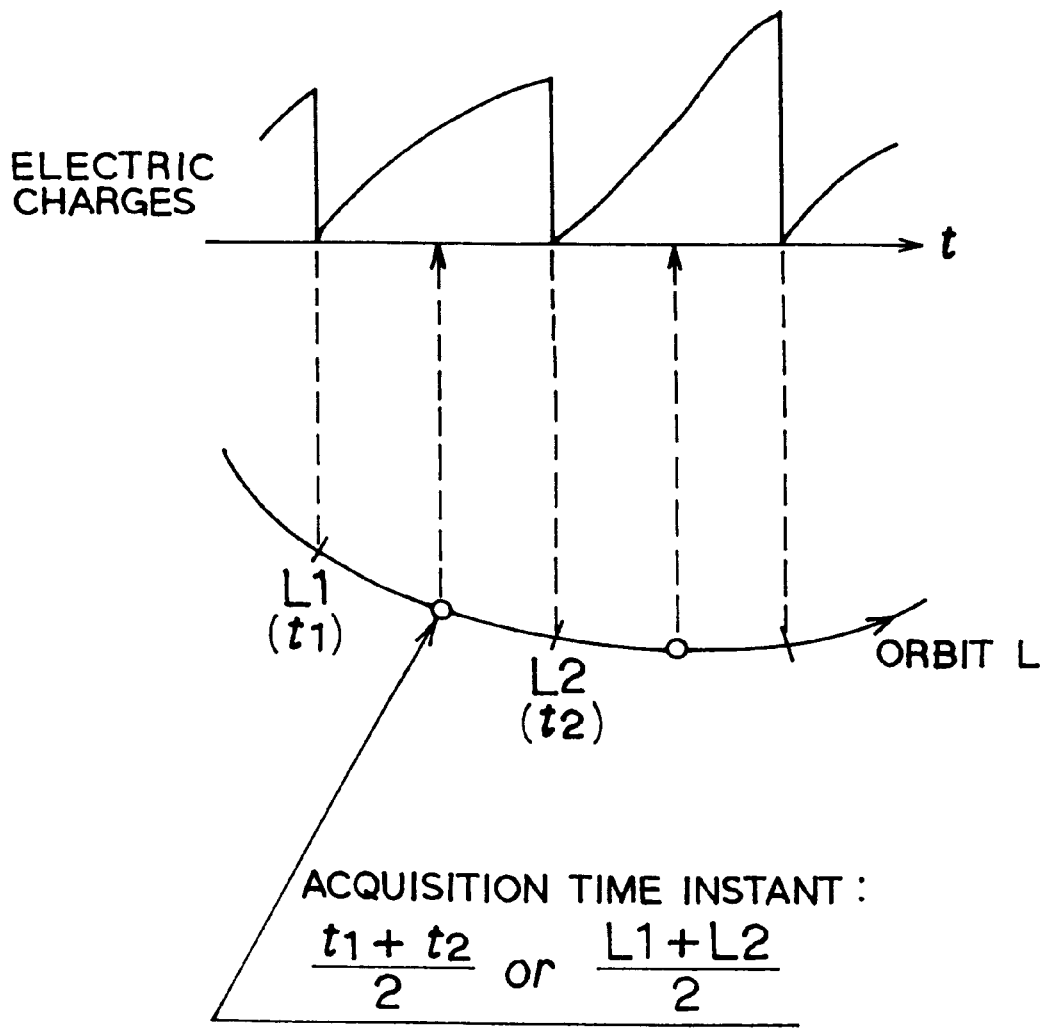
FIG. 25 illustrates a setting method of data acquisition timing for continuous X-rays.

Assume that, as shown in FIG. 25, an acquisition period for a certain frame data ranges from t1 to t2 (corresponding to positions L1 to L2 on a scan orbit L). In this case, the center-of-gravity of the acquisition time, i.e., the position of a central time, is decided; for example, the acquisition time for the frame is (t1+t2)/2.

In this method, it is proper that the acquisition time is previously calculated on the basis of the predetermined acquisition time instants t1, t2, t3, . . . of the frame data, and using their calculated times, the acquisition instructions are given to the detector to perform scans.

5.5.1.2. Center-of-gravity of Scan Orbits

According to this example, the center-of-gravity (distance) of scan orbits for each frame is pre-calculated. At a time instant when the scan point reaches the center-of-gravity position, instructions for acquisition are given to the detector. In the case of FIG. 25, the acquisition time becomes (L1+L2)/2 for a certain frame.

Only when a uniform moving speed is held on a linear scan orbit, the acquisition time based on the center-of-gravity of acquisition times and that based on the center-of-gravity of scan orbits become equal to each other.

5.6. DSA Based on a Plurality of Scans

Still another feature is that the same region of a patient is scanned a plurality of times for DSA (Digital Subtraction Angiography). Angiography preferably enables the detection of movements (changes) of contrast medium injected into the blood vessels and diagnosis for changes of a patient's interested region before and after the surgery.

5.6.1. Differences of Projection Data

One example for this category is calculation of differences between projection data. Projection data acquired in each view during a first scan are preserved as masking data. For each scan following the first scan, at every view, differences are calculated between the masking data and acquired projection data. In a recombination process of images, a plurality of frames of difference data are pixel-added to form a tomogram.

5.6.2. Differences of Tomogram Data or Volume Data

Another example is to calculate differences in either a state that two dimensional tomogram data of a slice have been obtained by recombination or a state that three dimensional volume data have been obtained by recombining each of a plurality of slices. In this case, for example, tomogram data or volume data obtained the first scan are assigned to masking data, and tomogram data or volume data obtained by scans following the first scan are subject to pixel by pixel a difference calculation from the masking data. This provides diagnosis for time-sequential changes of images.

5.6.3. Acquisition Timing of Masking Image Data

The timing for acquiring the masking image is not necessarily confined to the first scan, and can be set at any timing of scan, such as an intermediate scan or the last scan, depending on natures or conditions of observed physical values.

5.6.4. Non-linear Process After Difference Calculation

As one example of the process carried out after the difference calculation, there are provided non-linear processes.

5.6.4.1. Threshold Process as Non-linear Process

A practical non-linear process is a threshold distinguishing process. Data produced by the difference calculation are distinguished by a given threshold, in which all the differences less than the threshold are automatically set to zero. By this technique, the background contrast is compressed and the entire data amounts can be reduced.

5.7. Installation of Compensating Mechanism

As another feature, such mechanisms as a water bed or a wedge filter which have been practiced in X-ray CT scanners may be installed, which permits the dynamic range to be enlarged.

5.8. Strobe Imaging

Still another feature is provided by strobe imaging using pulsed contrast imaging.

5.9. ECG-gating Scan

Still another feature is provided by an ECG-gating scan. Instead of cycles in pulsed contrast imaging, cardiac cycles are employed.

6. Data Selection

Next, features and examples classified into the category "data selection" for the X-ray tomosynthesis system of the invention will now be described.

Image recombination in the system is carried out by selecting data from projection data of each frame, and adding the selected data pixel by pixel to the voxels of a slice. The "data selection" process becomes the most simplest form in cases where the tube and the detector are moved in parallel with each other.

Specifically, the spatial positions of the focus (tube) and the detector are detected to calculate the shifted amounts of projection data of each frame necessary for the image recombination, and the shifted amounts are then adequately corrected. In other words, the shifted amounts are not preset, and instead, it is allowed to calculate the shifted amounts after having completing scanning under a proper combined movement of the focus and the detector, or, a proper movement of the focus solely. Such free postcalculation of the shifted amounts leads to an easier setting process of scan conditions, such that selections of movement patterns of the focus and the detector are widened.

6.1. Use of Position Detecting Means

One feature is a method of detecting the positions of the focus and the detector, or only the focus using position detecting means. In this case, position information detected in detecting projection data for each view is memorized, and then the projection data of pixels matching to the position information are selected every frame.

6.1.1. Internally-mounted Position Detecting Means

As examples of the position detecting means, such means as an encoder or potentiometor mounted in the moving mechanism 16, are provided. This position detecting means is made up of, for example, the position sensor 36a or 36b shown in FIGS. 10 and 11.

6.1.2. Externally-mounted Position Detecting Means

Another example is the position detecting means mounted outside the moving mechanism 16. For example, an infrared ray detector detecting focus positions from the heat caused by the X-ray focus can be provided. One construction is provided such that this detector is fixedly oriented toward a certain spatial range of the detector within which the focus moves.

6.2. Utilization of Markers

As another feature about the position detection, there is provided a technique that uses markers different in X-ray transmittance ratios than a patient body, which enables the markers to be duplicated into each frame of projection data. Calculating the positions of the markers in each of a plurality of frames of projection data provides position information in each frame of projection data, which is necessary in data selection for image recombining.

Figure 26:
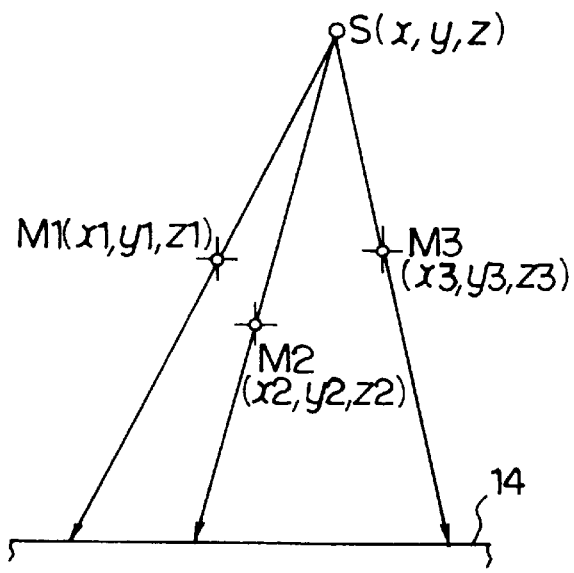
FIG. 26 illustrates utilization of markers.

FIG. 26 illustrates a practical example, where markers M1 (x1, y1, z1), M2 (x2, y2, z2) and M3 (x3, y3, z3) are provided between the focus S (x, y, z) and the detector 14. Solving nine simultaneous equations for the coordinates of the markers M1, M2 and M3 using projection data provides the position of the focus S, thus providing a relative movement amount of the focus. Specifically, in the case of FIG.

26, since the markers are three in number, six variables as for the detector 14 can be solved, providing the positions of the detector 14 and focus S. Additionally, one marker is enough, provided the position of the detector 14 is known (i.e., three variables).

6.2.1. Attaching Markers to Patient

Markers may be attached, by way of example, to a patient body.

6.2.2. Attaching Markers to Couch

Also markers may be attached to the couch (tabletop).

6.3. Correction of Constant Position Shifts Utilizing Markers

Figure 27:
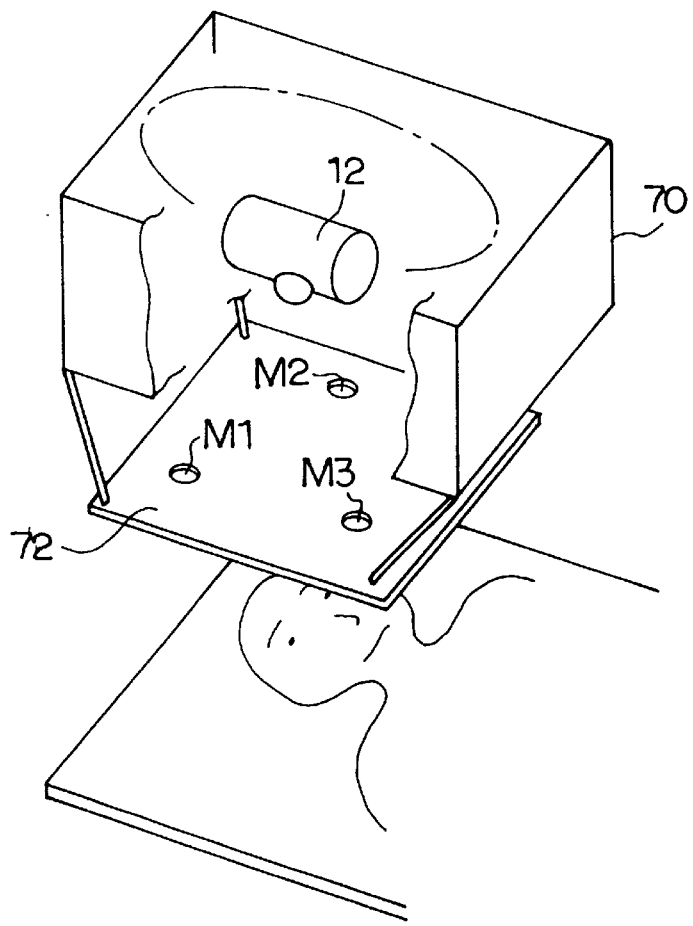
FIG. 27 illustrates correction of constant position shifts utilizing markers.

As another feature as concerning the data selection, there can be provided a process by which constant position shifts are corrected utilizing markers. For example, as illustrated in FIG. 27, a plate member 62 is placed in front of the tube 12 movable within a covering member 70. Pin-holes M1 to M3 serving as markers are formed through the plate member 62. In advance of scanning, position correction data are acquired using the pin-holes M1 to M3. Projection data acquired in the scanning are corrected based on the position correction data. By this method, constant position shifts, such as mechanical backlashes, can be corrected.

The markers M1 to M3 may also be attached to the couch.

7. Data Processing Prior to Image Recombination

Embodiments (features) classified into the category of "data processing prior to image recombination" of the X-ray tomosynthesis system according to the invention are provided. Though the data processes of this category are, in principle, not absolute necessities, it is preferable that, to increase image quality of later-recombined tomograms, one process or a plurality of processes properly selected from the following examples are solely or combinedly performed.

7.1. Correction of Scattered X-rays

One feature is correction of scattered x-rays. In principle, any technique or mechanism serves as correction of scattered X-rays. It is preferable to directly remove X-rays scattered by a patient or couch, or indirectly remove them through the correction.

7.1.1. Physical Removal by Such Physical Members as Grids

A practical example of the scattered-rays correction is provided by FIG. 28, where a barrier member 76 such a grid (hereinafter, referred to as "grid") is placed in front of the X-ray incidence surface of the detector 14. The grid 76 serves as a physical barrier to scattered X-rays.

7.1.1.1. Fixed Grid

A preferable grid allocation is to positionally fix a grid. Though projection data detected include those representing the shade of the grid, positions of data selected from each frame of projection data change for each view (i.e., frame by frame). Therefore, the shadows of the grid almost disappear automatically from a recombined tomogram.

7.1.1.2. Moving Grid

Figure 28:
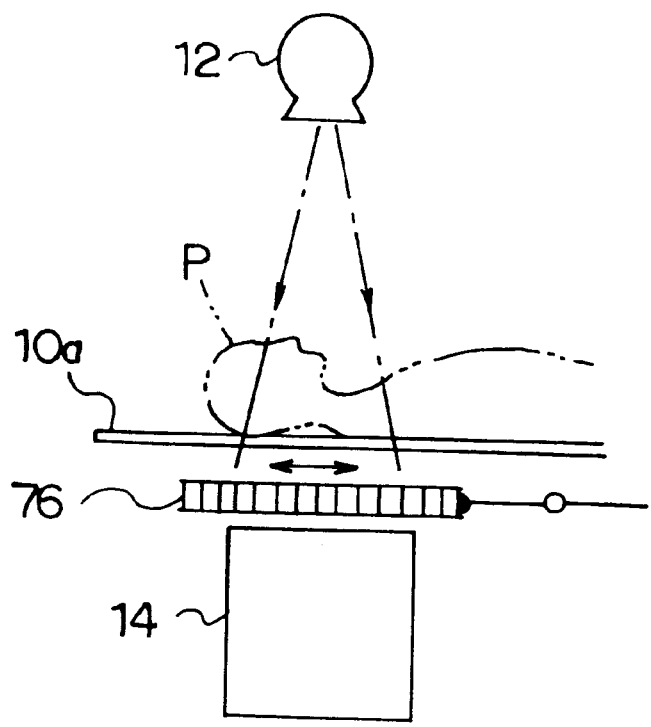
FIG. 28 shows the arrangement of a grid.

Another example concerning the grid allocation is that the entire grid 76 is moved during scanning (refer to FIG. 28).

In this case, it is also preferred that the grid is moved to erase the shades itself.

7.1.1.2.1. Practical Orbit

Practical orbits to move the grid 76 includes, for example, a circular orbit, figure eight-shaped orbit, and reciprocating orbit.

7.1.1.3. Example of Grid Shape

Figure 29:
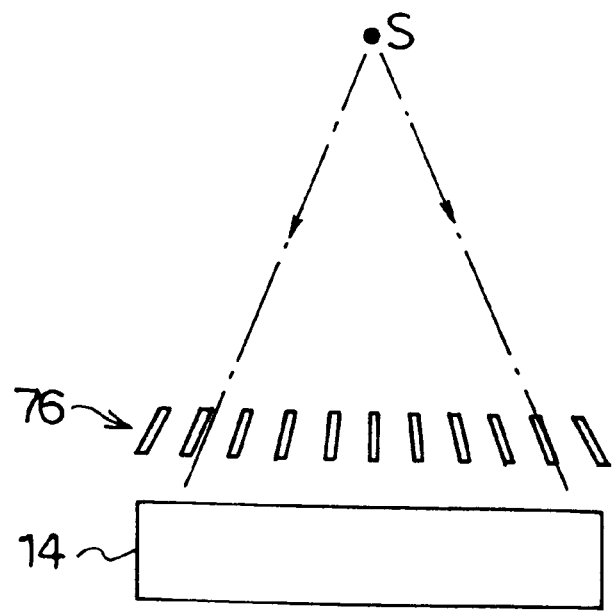
FIG. 29 shows the directions of grid blades.

Another grid may be designed so, as shown in FIG. 29, that a plurality of blades compose a grid 76 are placed to form a cone-like shape as a whole, and oriented to the focus S (tube). This placement allows transmitted X-rays to effectively impinge onto the tube with scatted X-rays barricaded sufficiently.

7.1.1.4. Movable Grid

Figure 30A:
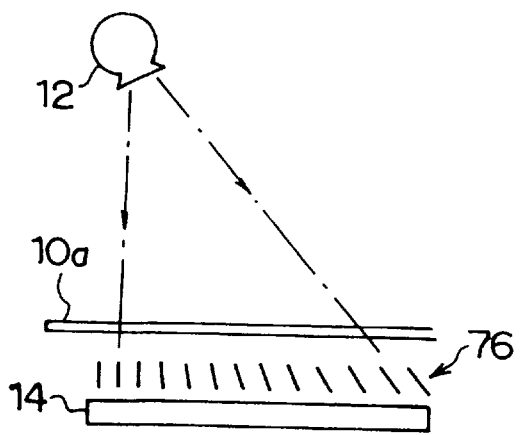
FIGS. 30A to 30B show a directional control of blades a movable grid.
Figure 30B:
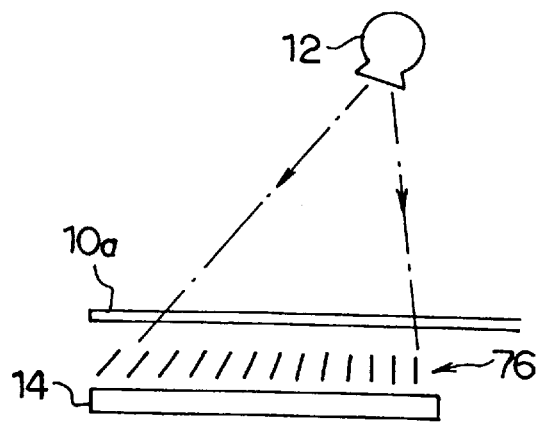

Still another example of the grid is shown in FIGS. 30A and 30B, where explained is a movable grid 76 structure which has a plurality of solely movable blades. Each blade is always controlled to be oriented to the focus S during scanning.

7.1.2. Mathematical Removal of Scattered X-rays

Another example according to the invention is provided by a mathematical removal method, of course, which can suitably be applied to the system. This mathematical removal may be used together with the foregoing physical removal using the grid, or may solely be used.

One practical method of the mathematical removal is known by ""A technique of scatter-glare correction using a digital filtration" Michitaka Honda et al., Med. Phys. 20(1), Jan/Feb 1993 pp. 59–70". Thus, prior to the image recombination process, projection data acquired are subject to an appropriate mathematical removal operation (such as PSF) by, for example, a computer incorporated in the control/processing apparatus 18.

7.1.3. Calculation of Amounts of Scattered X-rays

Another example is concerned with a construction which calculates amounts of scattered X-rays and corrects acquired data on the basis of the calculated amounts. Those amounts are figured out based on scan parameters etc. The parameters include an amount of X-ray beam energy, patient thickness, view size, distance between a patient and the detector, and others. One calculation example is shown in, for example, the following paper ""Method for estimating the intensity of scattered radiation using a scatter generation model" Michitaka Honda et al., Med. Phys. 18(2), Mar/Apr 1991 pp. 219–226".

7.2. Non-linear Process

Another feature is to perform non-linear processes on each pixel value of each frame projection data acquired.

7.2.1. Gamma Transform

One practical non-linear process is a non-linear gamma transform, which can be processed with, for example, a lookup table.

7.2.2. Filtering Process

Another non-linear process is provided by a filtering process properly-selected, such as a threshold process or median filter.

7.3. Logarithm Process

Still another feature is provided by a logarithm operation performed on each pixel value of each frame of projection data acquired. This can compress a value range into which all the pixel values fall, and provide recombining image data on which linear absorption coefficients directly reflect.

7.4. Beam Spread/correction of Detector Tilting Angle

As still another feature, there is provided a process by which the spread of X-ray beams and/or tilting angles of the detector are corrected based on a well-known "cos term".

7.4.1. Example of "cos term"

Figure 31:
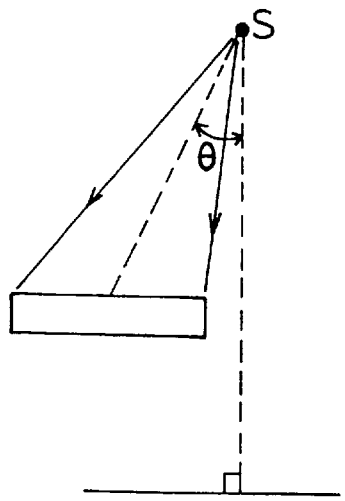
FIG. 31 explains correction of projection data with the "cos term"

A practical example is shown in FIG. 31, where the "cos term" method is adopted to correct X-ray paths along the thickness direction of a patient slice. When θ is an angle of a pencil-beam X-ray (a tilting angle θ to the vertical line passing the focus S) toward a certain voxel, each pixel value of each frame of projection data is multiplied by "$\cos^3 \theta$".

7.5. Filtering Process Prior to Recombination

Still another feature is a wide range of filtering processes performed prior to the recombination of images. These filtering processes are executed, for example, by the control/processing apparatus 18 through its software programs.

7.5.1. Isotropic Filtering Process

One example of the filtering process is a filtering process whose processing direction is isotropic.

7.5.2. Anisotropic Filtering Process

A further example is a filtering process whose processing directions are anisotropic.

7.5.2.1. Example of Anisotropic Filtering Process

The processing direction in the anisotropic filtering process is, as a preferable example, set in agreement with a moved direction of the focus. This removes artifacts that might appear along the focus-moved direction.

7.6. Removal of Movement Components (Other Slice Components)

This feature is concerned with removal of movement components from a plurality of frames of projection data acquired for the same slice. The calculation of this removal is performed by, for instance, a computer incorporated in the foregoing control/processing apparatus 18.

Figure 32:
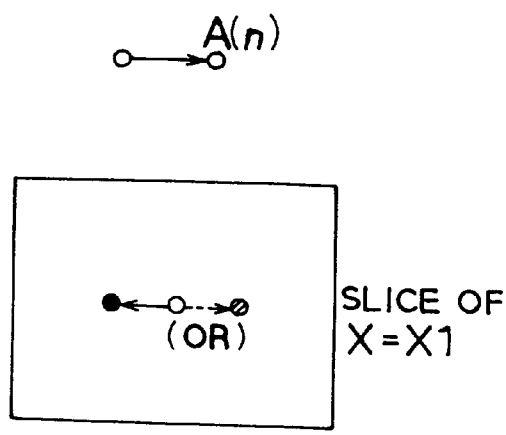
FIG. 32 explains movement components.

The "movement" referred herein, in addition to photon noises, is a state which projected positions of structures of other slices other than an objective slice change depending on a direction corresponding to a moving direction of the focus and distance corresponding to its moved distance. For example, as shown in FIG. 32. The movement M of structures of X=X2 in a slice at X=X1 can be expressed by $$M(X1, X2) = B(X2, A(n)) - B(X1, A(n)) \quad (1)$$

where A(n) represents the movement of the focus. When A(n) is two dimensional quantities, the movement M of structures also becomes two dimensional quantities. But, for detecting the movement frame by frame using pulsed X-rays, the movement M is linear.

By way of example, in the case that 100 frames of projection data are pixel-added (i.e., recombined), data of an objective slice are added to the same pixel positions 100 times, whereas data of structures of other slices added to the same pixel positions only one time. This addition process causes signal intensities of the structures of other slices to be less than those of the objective slice, producing the image of objective slice (i.e., the image is recombined). This process expresses an imaging principle itself of the system. In contrast, the reversed point of view is that the signals of structures of other slices are necessarily added to 100 positions anywhere in the objective slice. This is destiny on the imaging principle of the system, although it may decrease contrast resolution.

Components of other slices added to an objective slice, referred to as "movement components" herein, will now be removed by the following various ways.

7.6.1. Movement Detection with Data Differences

Figure 33:
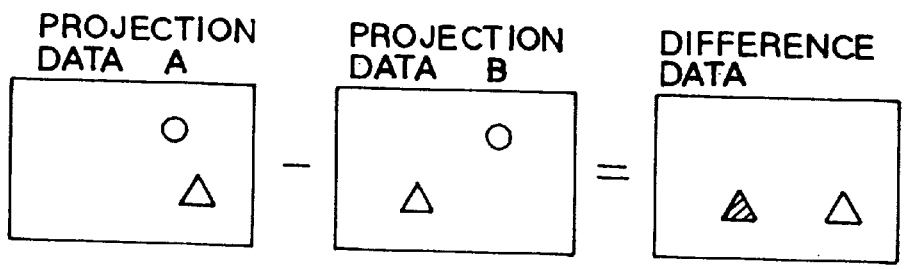
FIG. 33 shows one example for detecting movement components.

One example as concerning the removal process of movement components is based on detection of those through calculating data differences between frames. For example, as shown in FIG. 33, for two frames of projection data A and B, differences "A−B" are calculated at every mutually-corresponding pixels of those frames. A frame of those difference data serves as movement components.

Then, their absolute values |A−B| are calculated, before "A+B−|A−B|" for the first frame of projection data A, for example, is calculated, by which the movement components are removed from the projection data A. Repeating such removal calculation, for example, between temporal-adjoining frames permits movement components to be suitably removed from each frame. Therefore, the later-described recombination can be performed using only higher-quality projection data from which other slice components have been almost excluded.

7.6.2. Detection of Movement Components with Threshold

Figure 34:
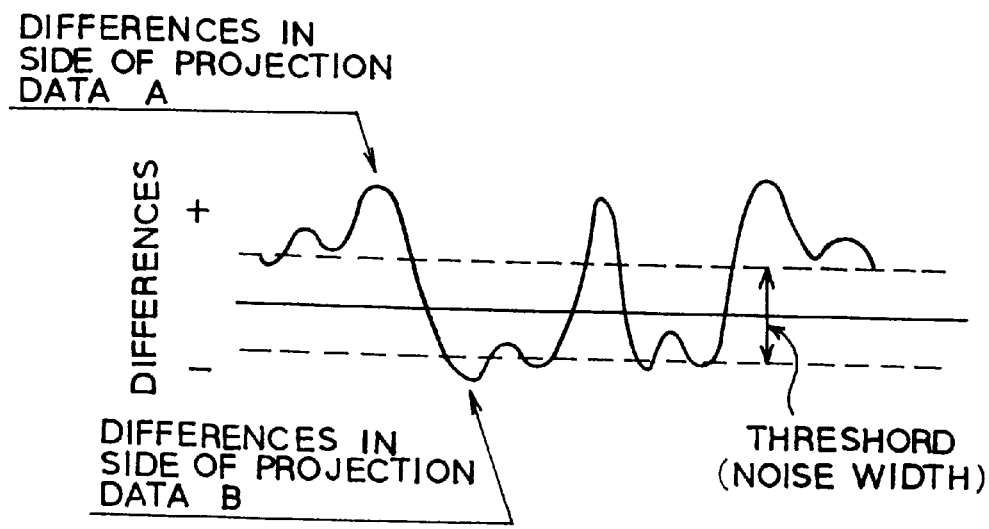
FIG. 34 shows an example for detecting movement components with thresholds.

Another detection example is given by a way to use a threshold discrimination process combined with the foregoing difference calculation. Namely, in FIG. 33, after having calculated the differences "A−B", those difference results are further subject to a discrimination process based on a given threshold. (Refer to an example showing fluctuations of difference data in FIG. 34.) By setting this threshold capable of removing noise components, the movement detection and removal of noise components can simultaneously be achieved by one process.

7.6.3. Detection of Movement Components Between non-adjoining Frame Data

Further another example is to apply the foregoing detection method to detection of movement components between non-adjoining two frames of projection data, such as between the first frame and the eleventh frame. In other words, every one or more frames, the detection can be performed, which provides an additional advantage that finer movement components which cannot be detected by detection between two adjoining frames are also detected and removed.

7.6.4. Detection of Movement Components with Restricted Detection Direction It is known that the movement components (i.e., other slice components) move along the direction opposite to a moving direction of the focus, not along the remaining directions. Therefore, as another example, a method by which the detection direction of movement components is restricted to one or more specified directions is provided, which simplifies the detection process.

7.6.4.1. Direction Dependent on Moving Direction of Focus

Practically, it is preferred that the detection direction is restricted to only the two directions mutually-opposite along a moving direction of the focus. In order to achieve this detection, a process is added which traces a moving direction of the focus frame by frame, then the detection of movement components is performed in only the two mutually-opposite directions along the traced moving direction.

7.6.5. Stopping Detection Process of Movement Components

This example relates to a method by which the detection is selectively stopped. For example, in the case of DSA, the movement itself of contrast medium is an observed object, which is injected and traced every frame. In such imaging, the detection of movement components is forcibly stopped by the control/processing apparatus 18 to which an operator sends necessary instructions.

7.6.6. Detection of Movement Components After Addition of a Plurality of Frames A still further example relates to the variations in the number of frames for detection. Though the foregoing detection examples have been described on the assumption that each one frame is subject to the detection, a plurality of frames can be synthesized, and the synthesized results can be subject to the same or similar detection. For example, the first to third frames of projection data are mutually added, the fourth to sixth frames of those are mutually added, and the two frames thus-added are subject to the foregoing difference calculation, difference calculation with thresholds, difference calculation with restricted detection directions, and others.

Handling such added frames increases S/N.

7.6.6.1. Variable Thresholds

When performing the difference calculation with thresholds, the thresholds can be changed in agreement with the number of added frames.

7.6.7. Another Method of Detecting Movement Components

Another method of this detection is such that, when assuming that two frames of projection data A and B are acquired, calculated pixel by pixel are differences considering weighting (including thresholds) based on $$A+B-\omega|A-B|$$

where ω is a weighting coefficient.

7.7. Correction of Distortion Detector Side

Another example in this category is associated with correcting distortion occurred in the inside of the detector. Herein, "the inside of the detector" is composed of the entire path routing from the X-ray incidence plane, such as I.I., to the D/A converter placed within the detector. If distortion occurs in the path, there appear an unfavorable phenomenon such that, even though X-rays indicative of a linear line come in, signals indicative of a curved line are output. A resultant tomogram include distortions.

Figure 35:
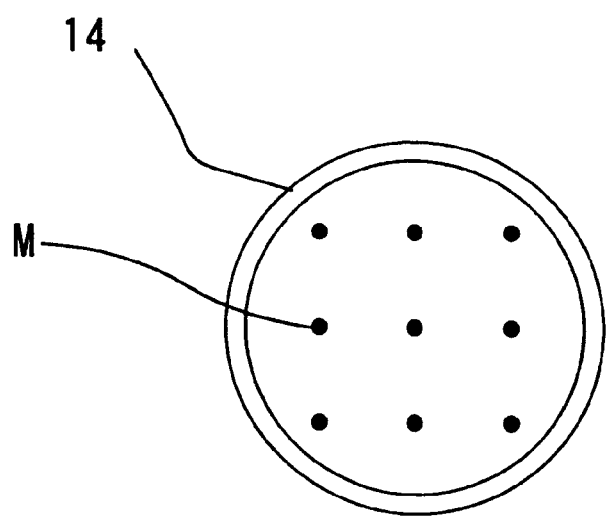
FIG. 35 shows an example of markers put on the front surface of the detector for correcting distortions caused due to detector's inside circuits.
Figure 36:
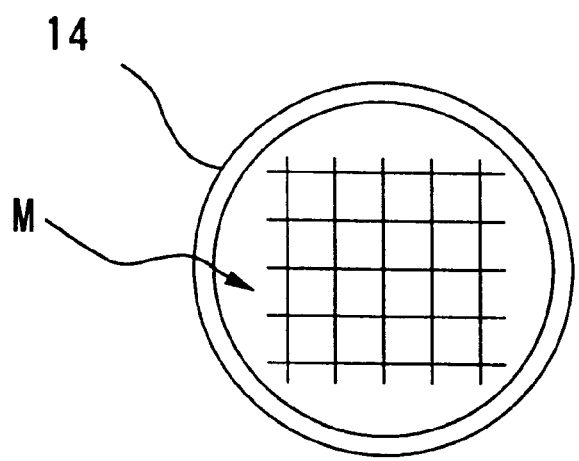
FIG. 36 further shows another example of markers put on the front surface of the detector for correcting distortions caused due to detector's inside circuits.

One counter measure is that markers different in X-ray transmittance ratios are put on the X-ray incidence surface of the detector, correction data are acquired with the markers, and the distortion in the detector inside is corrected based on the acquired correction data. This correction can be performed by the control/processing apparatus 18. FIGS. 35 and 36 exemplifies the markers put on the surface.

7.7.1. Concurrent Correction with Scanning

As one example of the distortion correction, as shown in FIG. 35, for example, a plurality of spot-like markers M can two-dimensionally be mapped on the incidence surface of the X-ray detector 14. In the spot-like markers, though their shade data are taken in as part of actual projection data, they have almost no influence on actually recombined images. Hence, by acquiring correction data concurrently with scanning, a dynamic correction calculation can be performed.

7.7.2. Acquisition of Correction Data Prior to Scanning

An alternative example, as shown in FIG. 36, a grid-like marker M can be placed on the incidence surface of the X-ray detector 14. For this marker configuration, because it is difficult to acquire correction data concurrently with scanning, they should be acquired and calculated before scanning, and stored in a memory. For scanning, the stored correction data are read out, and used for correcting acquired projection data.

7.7.2.1. Matching With Scan Orbit

Where the correction data are acquired in advance of scanning, it is preferable that the acquisition be matched in the shapes of scan orbits with acquisition for projection data.

7.8. Removal of Structures of Other Slices

Another feature is provided by a process by which data representing structures of other slices are calculated from reproduction data and removed.

8. Image Recombination

Next, features, embodiments, and variations classified into the category of "image recombination" of the X-ray tomosynthesis system of the invention will be explained. This image recombination is a process by which a plurality of frames of projection data acquired in a plurality of views are added pixel by pixel to form a tomogram at any slice. In detail, in agreement with a geometry among the tube focus, slice, and detector in each view, data each corresponding to voxels composing a desired slice are selected from each of a plurality of frames of projection data, and added to each other. Thus to perform the image recombination, for a desired slice, data selecting information representing which data should be selected from each frame of projection data is required.

The data selecting information is expressed as shift amounts along a linear direction when both the tube and the detector are linearly moved in parallel with each other. One fundamental feature of the present invention is that, including a situation where the tube and the detector are moved one-dimensionally, their arbitrary movement up to three dimensional ones is covered, and the image recombination can be performed regardless of the dimension of movement.

8.1. General Expression of Image Recombination

As described before, in the invention, it is enough that at least the tube focus is relatively moved against a subject and/or the detector, during which time a plurality of views are projected (scanned). Thus, the modes of movement of constituents involved in scanning consists of: movement of only the tube, movement of both the tube and the detector, a combination between movement of those two elements and movement of the tabletop (subject), and movement of only the tabletop. Movement of the tube and the detector ranges up to any three-dimension orbit.

First, the image recombination process performed in the invention will be expanded up to the third dimension, and a generalized expression of image recombination, which is independent on how the tube focus and/or detector are moved, will be shown. In the present invention, the image recombination described in this item is always practiced for any tomosynthesis imaging. The process of image recombination is designed to be executed by the control/processing apparatus 18.

Figure 37:
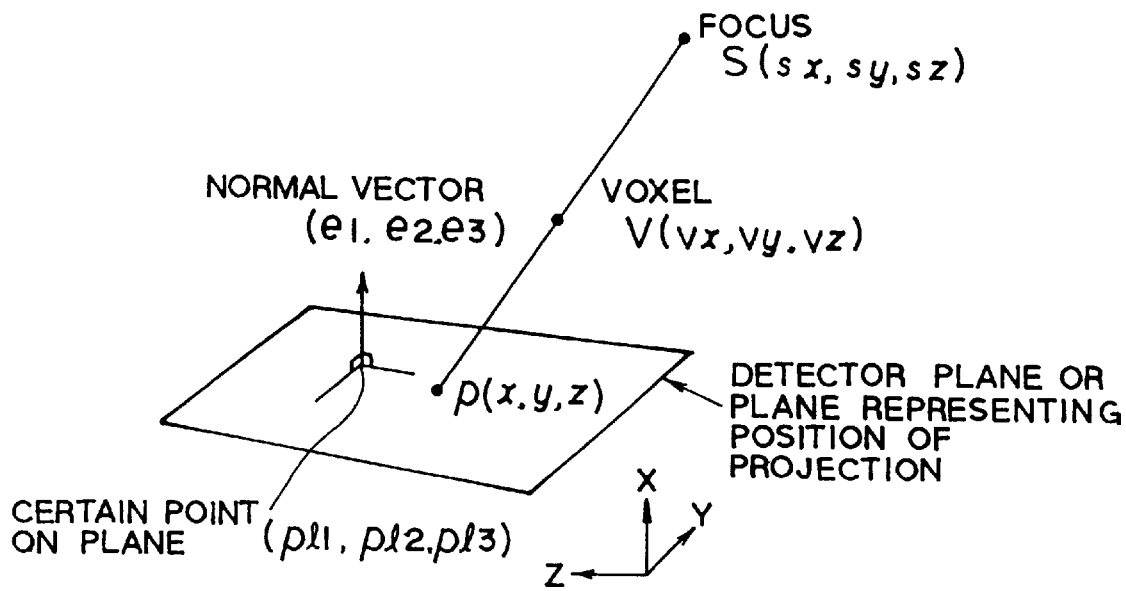
FIG. 37 is an illustration used for explaining a generalized expression of an image recombination process.
Figure 38:
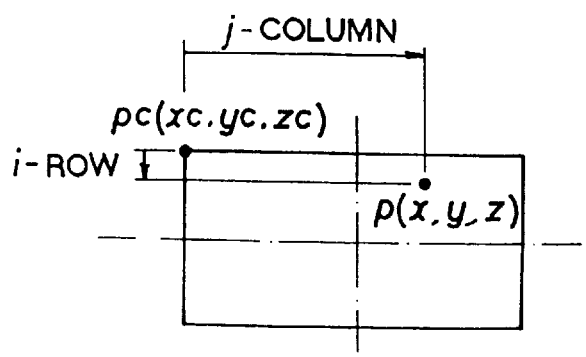
FIG. 38 is another illustration for explaining the conversion of the generalized expression from the absolute coordinate system to a relative coordinate system.

As pictorially shown in FIG. 37, assume that:

the coordinate of the tube focus:

$$S(sx, sy, sz)$$

the coordinate of voxels in a desired slice:

$$V(vx, vy, vz)$$

the components of a normal vector to a plane indicative of positions of projection data or the plane of the detector:

$$(e1, e2, e3)$$

the coordinate of a certain point in a plane indicative of positions of projection data or the plane of the detector:

$$(pl1, pl2, pl3).$$

The equation of a linear line connecting the tube to the voxels is expressed by $$\frac{sx-x}{sx-vx} = \frac{sy-y}{sy-vy} = \frac{sz-z}{sz-vz}(=k)$$

and then changed into $$x=sx-k(sx-vx)$$
$$y=sy-k(sy-vy)$$
$$z=sz-k(sz-vz) \quad (2)$$

Data used for recombining the voxels V (vx, vy, vz) should exist at the intersections between the linear line equation (2) and the detector, thus, in general, enough is to calculate the intersections between the linear line and the plane (surface) of the detector or a plane (planar or curved one) indicative of positions of projection data. When the plane of the detector or a plane indicative of projection data is planar (if such plane is curved, it is reformed into a planar plane by using a resampling technique, thus the assumption that the plane is planar being acceptable), an equation is provided as follows.

$$e1(x-pl1)+e2(y-pl2)+e3(z-pl3)=0 \quad (3)$$

The coordinates (x, y, z) satisfying the equation (3) should reside in a planar plane including the coordinates (pl1, pl2, pl3) when a normal line is provided by the vector (e1, e2, e3). The intersections can be obtained by solving the simultaneous equations of the expressions (2) and (3). Practically, substituting the expression (2) into the expression (3) produces $$k = \frac{[e1 \cdot sx + e2 \cdot sy + e3 \cdot sz] - [e1 \cdot pl1 + e2 \cdot pl2 + e3 \cdot pl3]}{e1(sx-vx) + e2(sy-vy) + e3(sz-vz)} \quad (4)$$

so substituting the expression (4) into the expression (2) provides the coordinates P (x, y, z) of the intersections. Finally, the coordinates P (x, y, z) thus-obtained correspond in the absolute coordinate system to positional coordinates of projection data which should be selected for image recombination.

In the recombination process, projection data at pixel positions corresponding to the absolute coordinates P are selected from each of a plurality of frames of projection data positionally moved frame by frame, and added to the voxels V. Information indicating relative movement of a geometry among the tube focus, subject (couch) and detector is used for the selection of projection data. The addition is carried out over the entire voxels.

On one hand, because the coordinates (x, y, z) of the foregoing points P are expressed in the absolute coordinate system, the specification of elements of the detector (i.e., data selection) becomes more easier if they are converted into a relative coordinate system P(i, j) based on a certain point pc (xc, yc, zc) on the detector. To realize this, calculation is performed on the basis of:

$P(i, j)$=projection data at i-row and j-column detected in a certain view by the detector, $$i=F[P(x, y, z)-pc(xc, yc, zc)],$$

and $$j=G[P(x, y, z)-pc(xc, yc, zc)],$$

where $F, G$: conversion functions  (5)

Since it is enough that the projection data p(i, j) of the intersections P(x, y, z) are successively added to each other, the final generalized expression is given by plural views $$\text{Image}(vx, vy, vz)=\Sigma p(i, j) \quad (6)$$

For this addition over a plurality of views, a weighting process may additionally be employed such that weighting coefficients for a certain one or more views are set to larger (or smaller) values.

In such cases where a calculated position p(i, j) does not correspond to an exact detector's detecting element, a projection data detected by a detecting element nearest to the calculated position P may be employed, or projection data detected by a plurality of detecting elements existing in the vicinity of the calculated position P may be interpolated and used.

Figure 39A:
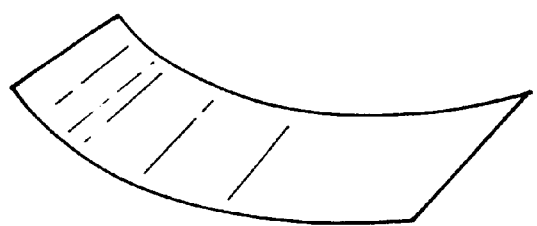
FIGS. 39A and 39B show variations of the detector surface (plane)
Figure 39B:

Yet it is not always necessary that the incidence plane of the detector is shaped into the planar plane. FIGS. 39A to 39C show some examples of the shape, where any shape may be available, like the shape of a circular arc in FIG. 39A, and the shape of a convex-expanded curve in FIG. 39B. The detector's incidence plane may freely be rotated in its level. On one hand, because the recombination calculation is performed for each voxel of a slice, the slice is not limited in shape to a planar plane; arbitrary curved planes may be available. Additionally, the slice may be an oblique planer plane of any angle (this corresponds to the direct production of MPR images in 9.1. item later-described).

8.1.1 Example of Orbit for Image Recombination (Part 1)

As orbits of movement of the tube (focus) for image recombination, various orbits such as two dimensional ones including rotation orbits and three dimensional ones may be used, not limited to a one dimensional orbit which is linear along a slice plane parallel to the floor (regarded as the horizontal plane). Moreover, orbits having no preset routes may be applied.

8.1.2. Example of Orbit for Image Recombination (Part 2)

As to orbits of movement of the detector for image recombination, one or two dimensional orbits parallel with the floor, or three dimensional orbits, including rotational ones, can be employed.

8.1.3. Example of Processing for Image Recombination

This example relates to examples of processing to recombine tomograms from a plurality of frames of acquired projection data. The X-ray tomosynthesis system in FIG. 1 has means for image processing to recombine tomograms, which is accomplished by the control/processing apparatus 18 performing a process based on the foregoing generalized expression. One such software processing example is shown in FIG. 67, which will be described below.

8.1.3.1. Processing Example (Part 1)

The control/processing apparatus 18 sets, for example, in response to input information through the input apparatus 19, a planar plane (displayed plane) as a slice including at least part of a subject (Step S31). The oblique angle of the planar plane to the subject is adjustable and can be set to a desired angle. Hence, an arbitrarily oblique slicing planar plane, which includes at least part of a subject, can be set. Then the apparatus 18 determines each coordinate included within the set plane (Step S32). Then, from projection data in each view, the apparatus selects projection data which should be added, based on a relative geometry between the focus and the detector (Step S33). This selection is carried out in agreement with the foregoing principle (8.1. item). The apparatus adds the selected projection data to the determined coordinates (Step S34). Those selection and addition processes are repeated for each coordinate in the set planar plane and for each view (Step S35).

Figure 67:
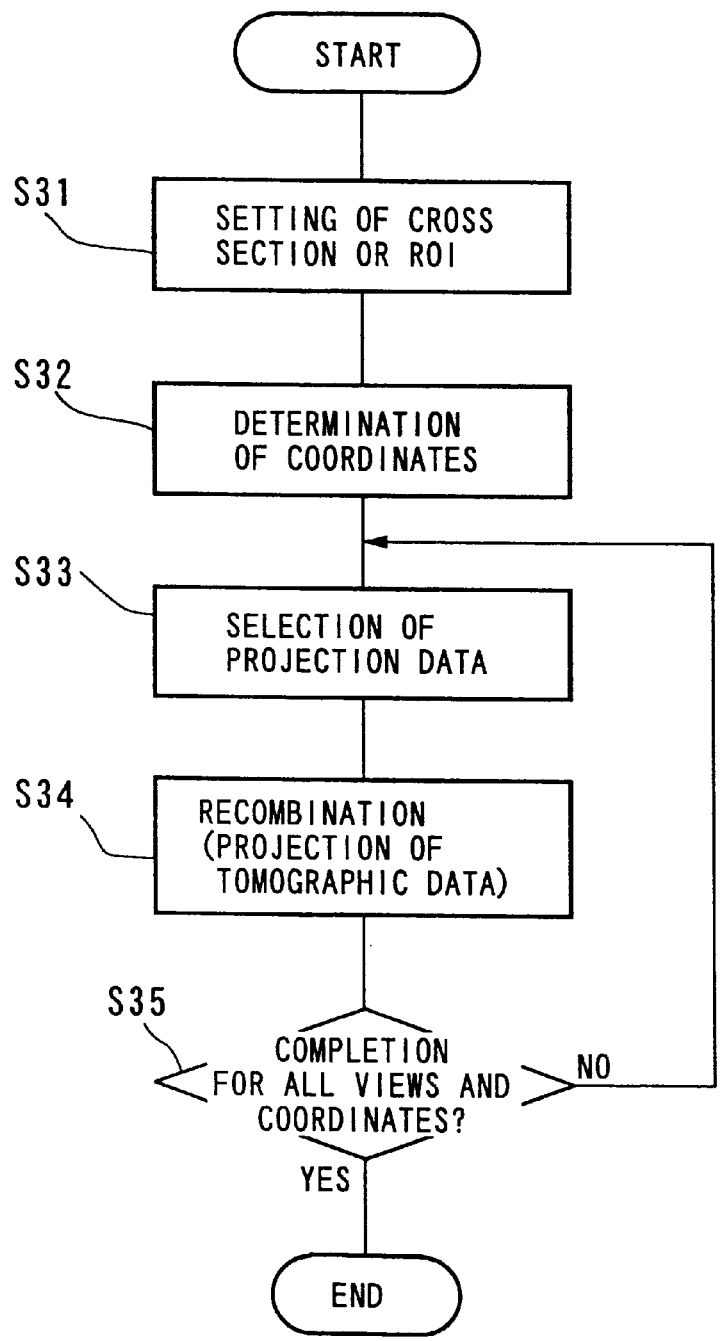
FIG. 67 is a conceptual flowchart showing an image recombination process in the embodiment.

In FIG. 67, Step S31 process constitutes setting means, Step S32 process does coordinate determining means, and Steps S33 to S35 do tomographic data producing means, respectively.

8.1.3.2. Processing Example (Part 2)

The control/processing apparatus 18 sets, for example, in response to input information through the input apparatus 19, a curved plane (displayed region) as a slice including at least part of a subject (step S31). Hence, an arbitrarily slicing curved plane, which includes at least part of a subject, can be set. Then the apparatus 18 determines each coordinate included within the set curved plane (Step S32). Then from projection data in each view, the apparatus selects projection data which should be added, based on a relative geometry between the focus and the detector (Step S33). This selection is carried out in agreement with the foregoing principle (8.1. item). The apparatus adds the selected projection data to the determined coordinates (Step S34). Those selection and addition processes are repeated for each coordinate of the set curved plane and for each view (Step S35).

8.1.3.3. Processing Example (Part 3)

The control/processing apparatus 18 sets, for example, in response to input information through the input apparatus 19, a ROI having an arbitrary three dimensional shape including at least part of a subject (Step S31). Then the apparatus 18 determines each coordinate included within the set ROI (Step S32). Then, from projection data of each view, the apparatus selects projection data which should be added, based on a relative geometry between the focus and the detector (Step S33). This selection is carried out in agreement with the foregoing principle (8.1. item). The apparatus adds the selected projection data to the determined coordinates (Step S34). Those selection and addition processes are repeated for each coordinate of the set planar plane and for each view (Step S35).

Executing any of the item 8.1.3.1. to 8.1.3.3. processes leads to a situation that the calculation is just confined to only each coordinate contained either a cross section set by an operator, i.e., a slicing plane, or in a three dimensional ROI. This provides a quick calculation time as well as requires less storage capacities of the apparatus 18.

8.1.4. Image Recombination of Plural Slices

This embodiment shows a method of obtaining a plurality of tomograms from projection data of a plurality of frames acquired at one time of scanning. Using this method eliminates the need for repeating scanning plural times. Only one time of scanning is enough, and a plurality of slicing positions are specified during the step of recombination, providing their tomograms.

Figure 40:
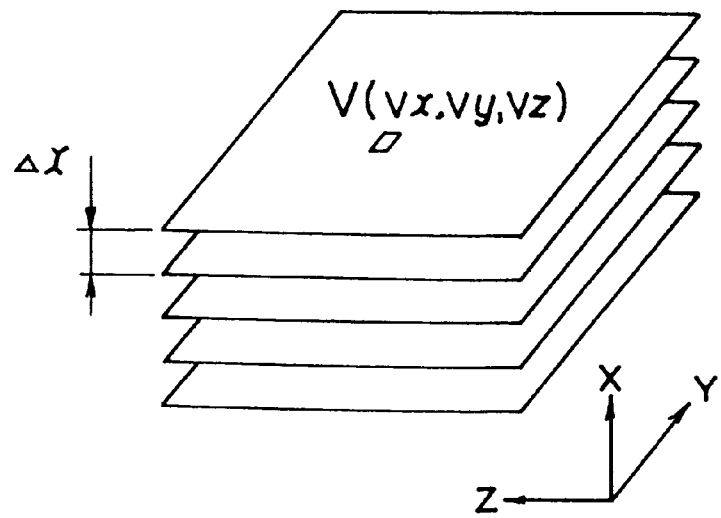
FIG. 40 shows a conceptual view explaining an image recombination process of a plurality of slices.

Practically, assume that in the above-described expressions (2) to (4) or (2) to (6), a slice of (i): vx=specified value, vy, vz=variables is recombined. At the next step, (ii): vx=vx+$\Delta$x(=distance between slices; refer to FIG. 40), vy, vz=variables are set for another slice which is then recombined. The process (ii) is then repeated for a plurality of desired slices, respectively.

This can produce tomograms of a plurality of slices which exist at arbitrary positions from projection data acquired by one time of scanning.

8.1.5. Data Selection Method of Projection Data for Each View

An alternative embodiment is selection of data from projection data acquired for each view.

Figure 41A:
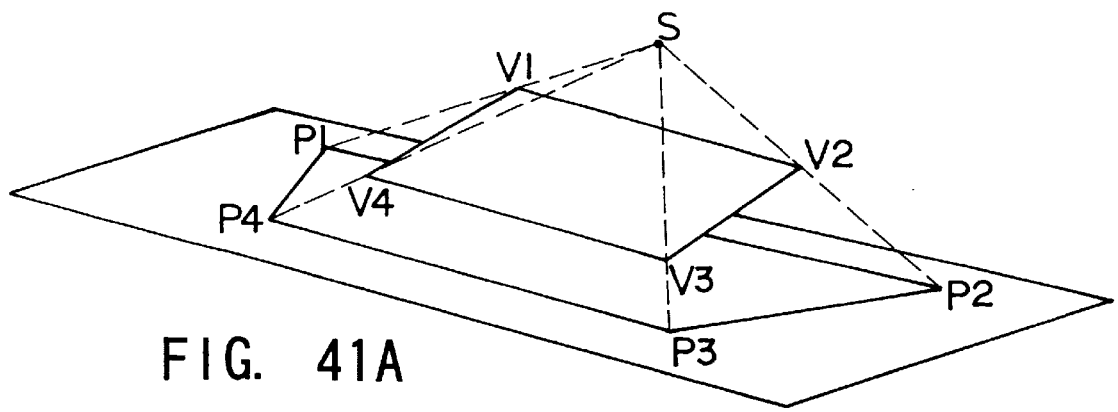
FIGS. 41A to 41C show one example of selecting data from projection data in each view.
Figure 41B:
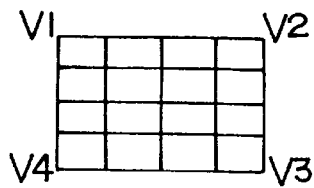
Figure 41C:
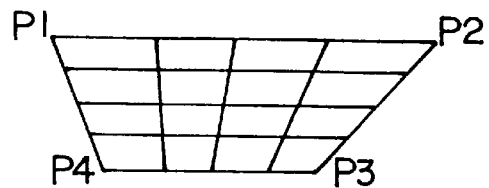

In this embodiment, as shown in FIG. 41A, a region lying in a planar slice, which is specified by four voxels V1 to V4, is specified. Specifically, for each of the voxels V1 to V4, the recombination process described in the item 8.1. is repeated, four times as a whole, to calculate their corresponding positions P1 to P4 in the detector's plane or in a plane representing positions of projection data. Then, arbitrarily positioned voxels in the slice are uniquely expressed using the four voxels V1 to V4. By way of example, as shown in FIG. 41B, the position of an arbitrary voxel can be expressed by the grid points interior-dividing the region defined by the voxels V1 to V4. Then, the positions of the projection data for the arbitrary voxel are expressed using the positions P1 to P4. By way of example, as shown in FIG. 41C, those positions of the projection data are readily obtained as the grid points whose grid interior-dividing the region determined by the positions p1 to P4.

Specifying projection data utilizing the positions of pre-given four voxels V1 to V4 can avoid a huge amounts of calculation for solving the foregoing simultaneous equations for all the voxels, thereby enabling a speedy processing.

Though the above embodiment is for a region connected by the four points, any shape of region and coordinates can be combined, such as an ellipse having a center position and major and minor diameters.

8.1.6. Image Recombination in Combination With Resampling

Still, an alternative embodiment is concerned with a method of image recombination combined with a resampling technique.

In the recombination of a planar slice plane, when the detector's plane or a plane representing projection data is non-planar, the projection of linear lines results in non-linear ones. Hence, in such a case, it is extremely difficult to specify projection data added and calculate the points P, requiring a large quantities of complicated calculation, it seems that practical applications are difficult. In particular, it is considered that such tendency be enhanced when recombination for a plurality of slices is performed. In contrast, this situation is also true even when the detector's plane is planar and a slice plane is non-planar, having the same shortcoming.

Thus, an object of this embodiment is to not only recombine an image as if linear lines are projected as their linear lines but also provide a higher speed tomography by performing the complicated calculation at a time.

Figure 42:
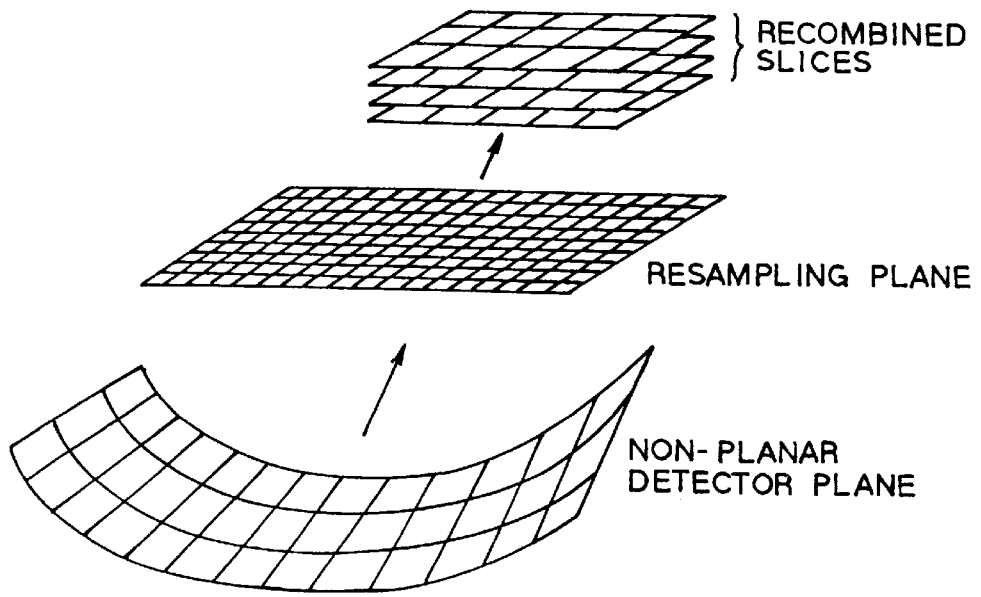
FIG. 42 shows one example of an image recombination process involving resampling.

In this embodiment, as shown in FIG. 42, if the detector's plane is non-planar and slices plane are planar, a resampling planar plane is prepared which is a virtually set plane in a memory. For all the views during scanning, the distance between the resampling plane and the tube focus is held constant and in parallel with slice planes recombined. Further, it is preferred that the voxel lines of the slice planes and the resampling lines of the resampling plane are parallel with each other. The resampling plane is matched in the shape with the slice planes, and, for example, as shown in FIG. 42, the slice planes are planar, the resampling plane is set to be planar. Like FIG. 43, if the slices are curved-panoramic, the resampling plane is also set to the same shape. Furthermore, as shown in FIG. 42A, the foregoing non-planar detector plane (or detecting plane) includes a polygon-mirror type plane consisting of a plurality of planar planes and substantially forming a curved plane.

Figure 42A:
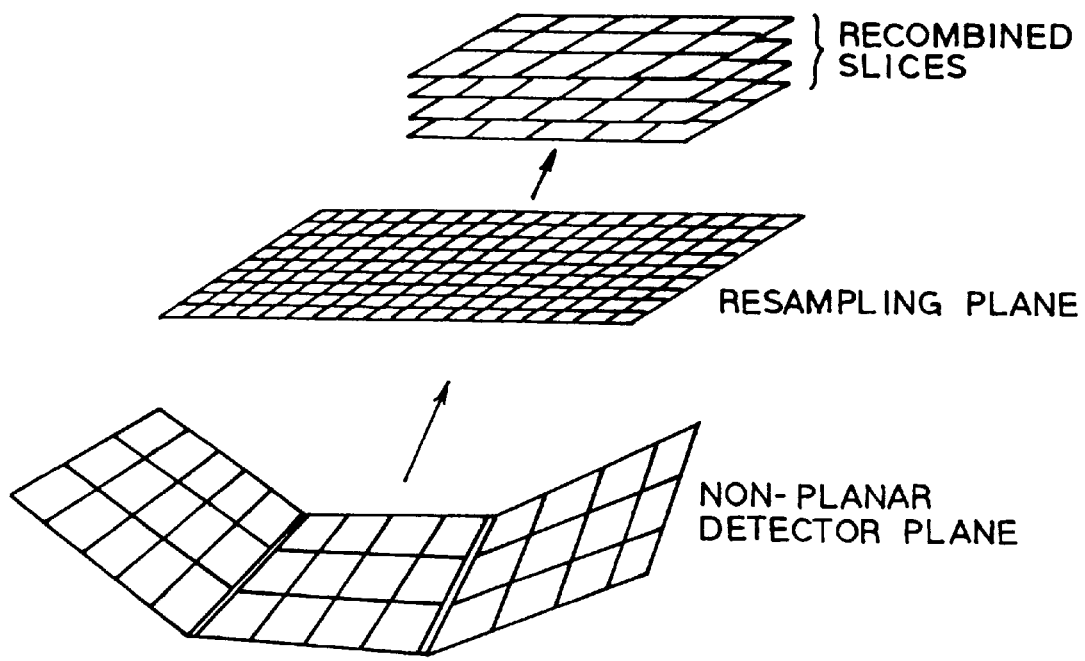
FIG. 42A shows another example of an image recombination process involving resampling.
Figure 43:
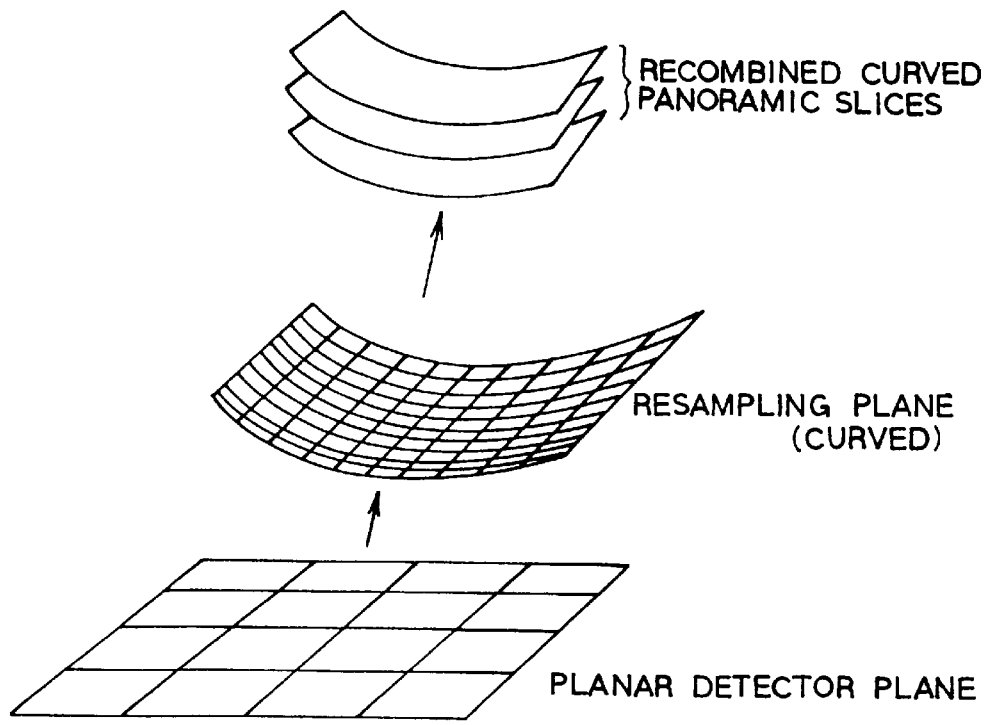
FIG. 43 is another example of an image recombination process involving resampling.

In the case of FIGS. 42 and 42A, projection data acquired by the non-planar detector are temporarily resampled onto the planar resampling plane. Then, from the resampled projection data on the resampling plane, data are selected (sampled) for image recombination, and those selected projection data are added to each other. The sampling pitch for sampling projection data on the resampling plane is set to be smaller than an original data sampling pitch on the detector's plane. This setting suppresses errors in interpolation.

The resampling process enables a faster recombination of tomograms of a plurality of slices, independently on the shape of the detector and/or the movement direction.

Figure 44:
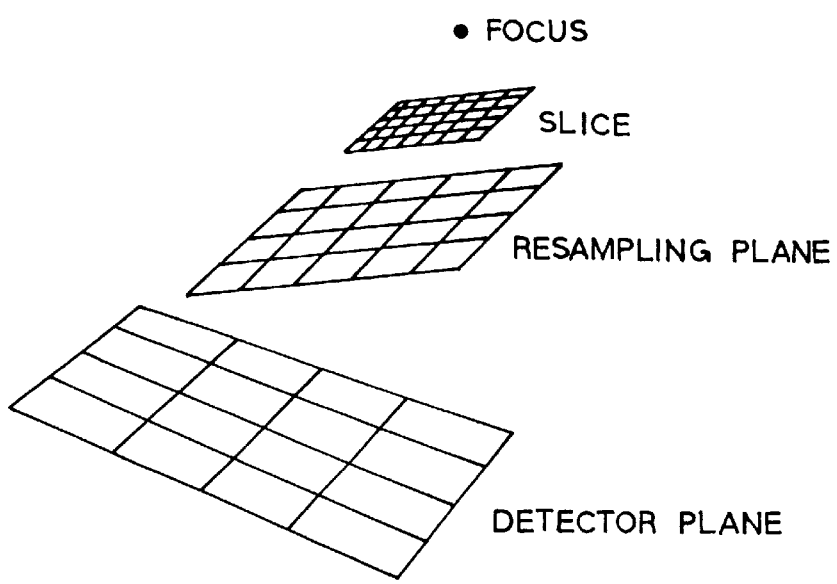
FIG. 44 is still another example of an image recombination process involving resampling.

In FIG. 44, there are shown a planar slice plane and the detector plane, both of which are planar but different in slopes from each other. For this case, a resampling plane is adopted on the foregoing principle.

8.1.7. Data Selection and Image Recombination for Parallel Movement of Detector and Three Dimensional Movement of Focus In this embodiment concerning image recombination, there is provided a typical mode of movement of detecting-system components, in which the detector is moved in parallel with the floor (i.e., horizontal plane in the system's coordinate system) and the tube focus is moved three-dimensionally. Explanation will now be given to this mode.

Figure 45A:
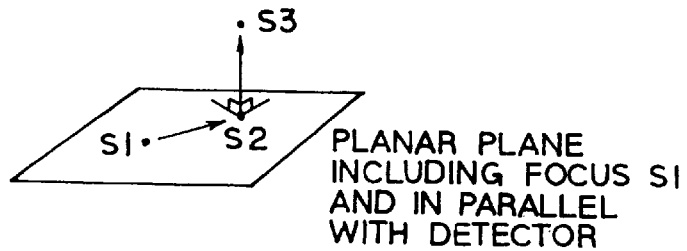
FIGS. 45A to 45C are another illustrations explaining data selection and image recombination processes.
Figure 45B:
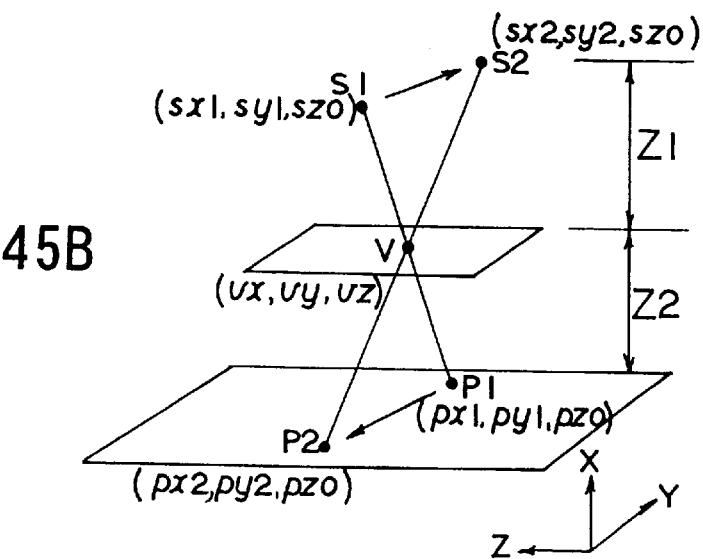
Figure 45C:
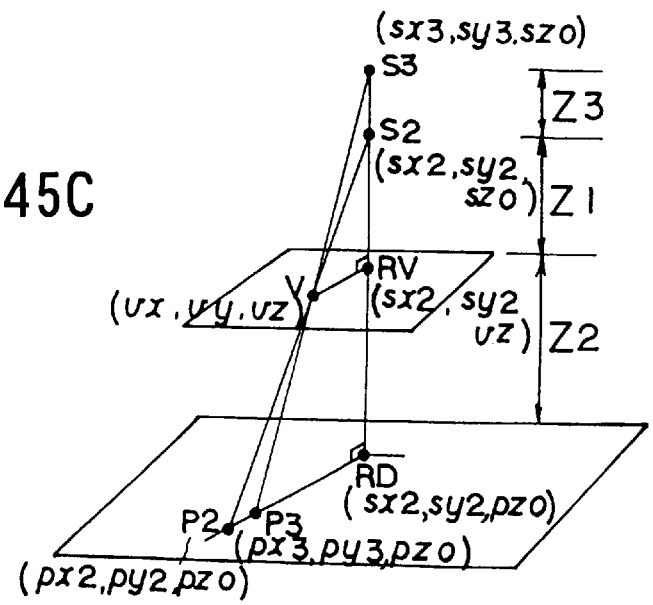

As illustrated in FIG. 45A, assume that the focus S is moved three-dimensionally from S1 to S3 via S2. The moved amounts of the focus S is divided into a parallel-direction movement component and a vertical-direction movement component. That is, it is considered that the focus S is parallel-moved from S1 to S2, and vertical-moved from S2 to S3.

(i) First, as to be parallel-direction movement component, for an arbitrary voxel in a slice plane, a position P2(px2, py2, pz0) shifted from the focus position S2 is calculated on the following expression (7):

$$[(px2, py2, pz0)-(px1, py1, pz0)]/Z1=[(sx2, sy2, sz0)-(sx1, sy1, sz0)]/Z2 \therefore (px2, py2, pz0)=(px1, py1, pz0)+[(sx2, sy2, sz0)-(sx1, sy1, sz0)]\cdot(Z2/Z1) \quad (7)$$

The right-hand second term expresses the shifted amount (in this case, vector quantities).

Though an arbitrary voxel V is an objective in the above, like FIGS. 41A to 41C, plural reference voxels V1 to Vn (in FIGS. 41A to 41C, V1 to V4) for defining a region in a slice plane can be applied to the expression (7) to obtain their shifted amounts, respectively.

(ii) A shifted amount of the focus as to the vertical direction movement component from S2 to S3 is then obtained. On the basis of intersections RV(sx2, sy2, vz) and RD(sx2, sy2, pz0) of normal lines extending from the focus position S2 and S3 to the slice and the detector planes, respectively, a shifted position S3(px3, py3, pz0) is obtained by the following expression (8) for data selecting for the obtained position.

$$(|V-RV|)/(|P3-RD|)=(Z1+Z3)/(Z1+Z2+Z3)$$

$$(|V-RV|)/(P2-RD|)=(Z1)/(Z1+Z2)$$

$$\therefore (px3,py3,pz0)=C(px2,py2,pz0)+[1-C](sx2,sy2,pz0)$$

$$C=\{Z1(Z1+Z2+Z3)\}/(Z1+Z2)^2 \quad (8)$$

Even for the second time of calculation of shifted position, like the first one, plural reference voxels v1 to Vn (in FIGS. 41A to 41C, V1 to V4) determining a region in a slice are each subject to the calculation under the expression (8) in order to obtain scaled-up or -down shifted positions, and for the remaining voxels, the calculation is made using the reference voxel positions.

8.1.8. Data Selection for Parallel Movement of Both Tube and Detector (Scaling-up or -down is Necessary)

Image recombination requires, in some form, to select of data added to objective volume constituting a slice from each frame of projection data. A mode of movement which makes it into the simplest form calculation of positions for the data selection is to move both the tube and the detector in parallel with the floor.

In the case of scanning with the tube and the detector parallel-moved, image recombination is performed such that projection data in each view are given shift amounts changed for each desired slice in the parallel movement direction and are added to each other.

Figure 46:
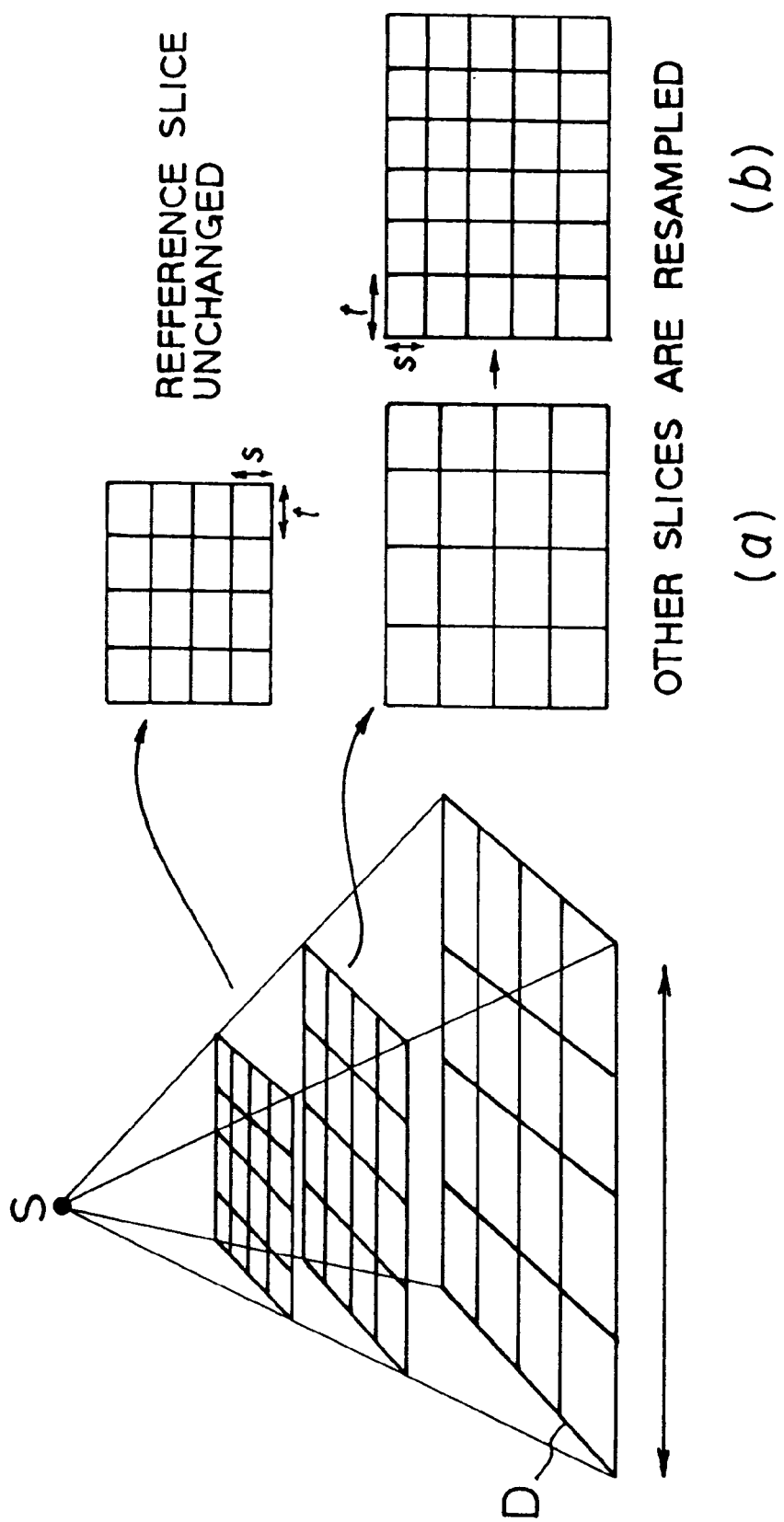
FIG. 46 is another illustration explaining data selection and image recombination processes.

However, the number of sampling pitches in projection data (for example, the pitches of 400 pixels×400 pixels) is equal over all the slices. Therefore, if as-shifted projection data are added to each other, the spatial sampling pitches in slices become different from each other due to geometries between a plurality of slices and the tube focus S and the detector plane D, as shown in FIG. 46. Namely, recombined (added) slice images are mutually equal in sampling pitches in the memory, but different in spatial sampling pitches (i.e., scaling-up ratios), as shown in FIG. 46. When a plurality of slice images each having different sampling pitches are subject to three-dimensional processes or animation display, there occurs distortions in their positions, shapes, etc.

In contrast, in the present embodiment, a plurality of recombined slice images are resampled in spatially-even-distance pitches in each slice plane, so that both the sampling pitches (corresponding to the scaling-up or -down process) are equal to each other. One such even-distance pitch is set to a pitch of an arbitrary one selected from plural slices. This adjustment of the sampling pitch can avoid the drawback described above.

In advance of image recombination, it is possible that projection data for each view are resampled, and their resampling pitches are adjusted to equalize the spatial sampling pitches in the memory.

8.1.9. Data Selection for Parallel Movement of Both Tube and Detector (Scaling-up or -down is Unnecessary)

This embodiment relates to an alternative technique of selecting data when both the tube and the detector are parallel-moved.

(i) using the projection data in the first view, each of a plurality of slices undergoes the process described in item 8.1.4. (refer to FIG. 40). This allows projection data used for the recombination to be specified voxel by voxel in each slice. (It is also acceptable that all the voxels are specified by performing the process in item 8.1.)

(ii) As to the next view and subsequent views to it, a shifted amount for each slice is calculated from the expression (6). Position data shifted by an amount obtained from data used in the recombination for an immediately prior view are employed for recombining each voxel in the present view to be calculated. (Alternatively, a shift amount for an objective slice may be obtained from the shift amount of a certain slice, based on the geometry.

Thus, setting equally the pitches (distances) of voxels in all of a plurality of slices enables data selection and recombination, independently on the issues of scaling-up or -down ratios.

8.2. Processing of Scaling-up and -down

An alternative feature concerning the image recombination category is provided a process by which slice images are scaled up or down to make them equal. Slice images (i.e., voxel images) sided to the focus are larger in enlargement (scaling-up or -down) ratios than those sided to the detector.

In other words, because the enlargement ratios of slice images change owing to the height X of slices, the ratios needs to be equal. A process for the equalization is carried out by the following expression.

$$S2(X, Y0, Z0)=S1(X, aY, bZ)$$

coefficient $a=a(X)$, coefficient $b=b(X)$ \hfill (9)

In cases where image recombination is performed on the generalized expression in item 8.1., this kind of process for adjusting the enlargement ratios is unnecessary.

8.2.1. One Time of Processing of Both Image Recombination and Enlargement Ratio Adjustment For pixel-adding (recombining) projection data, data which should be added are specified (selected), in which time, when a pixel of which position corresponds to the specified position does not exist, the pixel would be interpolated with, for example, neighboring four points. This increases an actual pixel size. If the interpolated data are additionally subject to the adjustment of enlargement ratios, the spatial resolution of the data decreases (becomes blurred). To avoid such situation, using the following expression, it is preferable to obtain at a time a plurality of slice images whose enlargement ratios are equal.

$$S3(X, Y, Z)=\Sigma(P\Delta n, aY, b(Z+B[X, A(n)])/N \hfill (10)$$

This approach provide one time of correction calculation without deterioration of the spatial resolution.

8.3. Cutting Out Slice Image at Arbitrary Angle From Volume Data

Furthermore, an alternative feature is provided by a process of cutting out a slice image at arbitrary angles from a set of volume data. This process is executed by, for example, the control/processing apparatus 18, under an interactive mode with an operator. Changing slice positions and recombining a plurality of slice images provides a three dimensional volume data. Then, performing an MPR (Multi Planar Reconstruction) on the volume data to which a desired angle has been specified provides a slice image along the angle. By using this method, any oblique, axial, and sagittal image can be produced from a coronal volume data, for example.

In the invention, to obtain slice images along desired angles directions, it is not always necessary to perform the cutting out technique using the MPR. Owing to the fact that the image recombination process generalized up to the three dimension is performed to add data voxel by voxel, specifying an oblique plane at an arbitrary angle when recombining data results in that projection data are individually added to voxels forming the oblique slice spatially inclined. This means that an oblique image of any inclined slice can be directly produced from projection data.

8.4. Simultaneous Image Recombination With Acquisition

Although the above-explained constructions has been based on the assumption that a situation where image recombination is executed after acquisition of projection data, timing to perform image recombination is not necessarily limited to it. Alternatively, it is available to concurrently perform acquisition of projection data and image recombination, which constitutes another feature. This can be realized by the control and processing by and in the control/processing apparatus 18, of which practical example will be below.

8.4.1. Practical Example of Simultaneous Recombination

Figure 47:
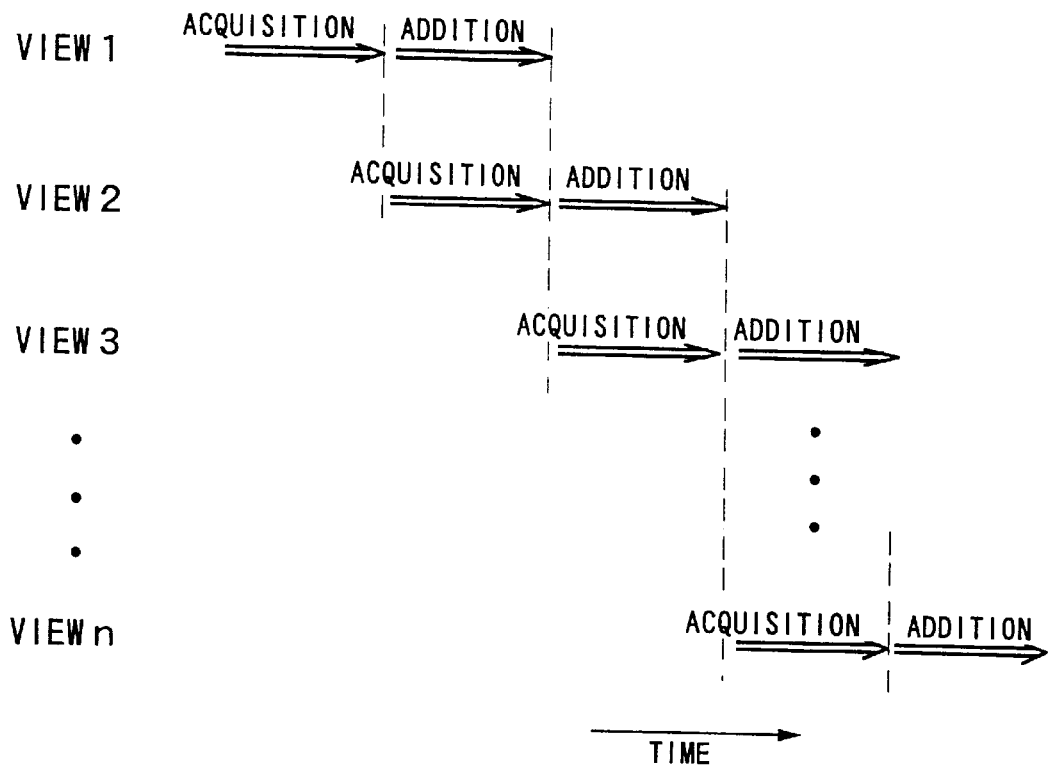
FIG. 47 is an illustration showing a procedure of image recombination executed concurrently with projection data acquisition.

To perform the simultaneous recombination, scan orbits and times when projection data are acquired are set beforehand. In other words, in the production of recombined images, previously determined is information about data selection notifying which pixel value in each frame of projection data should be added to which pixel position in a desired slice. Therefore, as pictorially shown in FIG. 47, immediately after the projection data for a certain view have been acquired, the projection data are each added to the voxels of a slice, during which period the projection data for another view are acquired. This series of processes are repeated for each of the views, which leads to a concurrent process of projection data acquisition and image recombination, quickly providing tomograms of slices.

8.5. Weighting Addition Process

As an alternative feature, there is provided a method of performing weighting addition dependently on acquisition positions of projection data (i.e., scan orbits). This addition is also selectively practiced in the image recombination process executed by the control/processing apparatus 18.

For example, as shown in FIG. 24A, consider that the tube is moved along an eliptic orbit in the two dimensional YZ plane. In this case, projection data acquired for views at orbit positions whose curvature radii are smaller are multiplied less weighting factors and added, as compared to those acquired for views at orbit positions whose curvature radii are larger. Smoothly changing the weighting coefficients in agreement with the magnitudes of the curvature radii it makes it possible to suppress or prevent generation of artifacts. Further, it is advantageous to exclude the need for a complex control required for adjustment of timing of acquisition and movement speeds on the orbits according to the orbit shapes, which have been introduced in item 5.2.

8.6. Large View Imaging (Part 1)

Tomograms absolutely require to include a region of really medical interest therein, on the other hand, it is frequently more helpful that peripheral regions around such region of interest are also widely imaged. Namely, larger views are convenient.

Figure 48A:
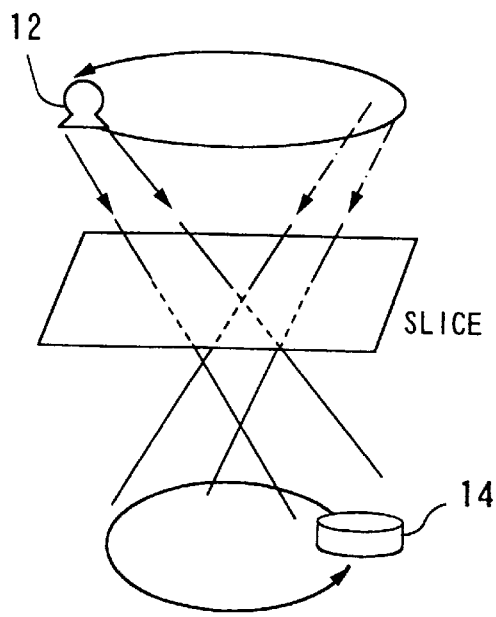
FIGS. 48A and 48B are illustrations of one example for a large view imaging technique.

For this reason, an alternative feature is provided by large view imaging obtaining tomograms larger in size than the detector size. The large view imaging can be achieved by the control/processing apparatus 18 in the stage of image recombination. By way of example, as shown in FIG. 48A, the tube 12 and the detector 14 are both moved along a circular scan orbit, during which time data acquisition is carried out. In this situation, even a spatial edge region through which an X-ray path has passed only one time is counted in and specified as a sliced plane region. The entire sliced plane undergoes image recombination process. It is preferred, however, that the recombination process employs an averaging technique, thus excluding or suppressing unevenness in density of images resulting from mere adding.

Figure 48B:
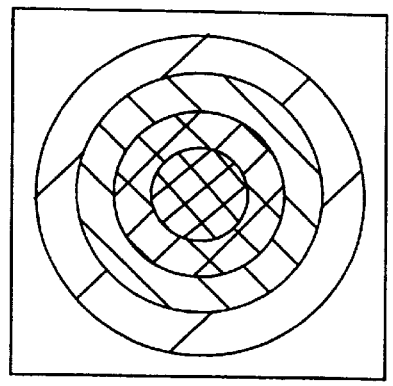

As a result, there is provided a recombined tomogram of a large view slice plane larger in view size than the detector size. This tomogram include, as shown in FIG. 48B, not only a central part where the number of adding is larger and which has higher accuracy, fineness and resolution but also peripheral parts, which are positioned around the central part, where the number of adding is smaller and which have lower accuracy, fineness and resolution. A region of really interest in terms of diagnosis is generally set to be imaged in the central part. This technique can provide tomograms having as widened views including regions of interest as is possible.

8.7. Large View Imaging (Part 2)

An alternative aspect for this imaging will be explained. This large view imaging is to perform a plurality of times of scans as an imaging view is moved, and overlap the recombined images obtained from the plurality of scans one on another with the positions of those image matched. A process required for this imaging technique can be achieved as post processing by the control/processing apparatus 18, using the image data recombined based on data acquired through a plurality of times of scans.

Figure 49A:
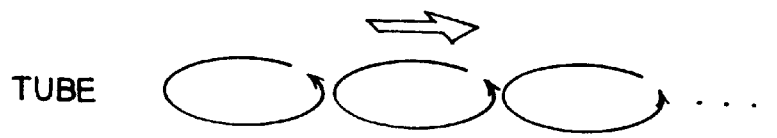
FIGS. 49A to 49D are illustrations of another example for a large view imaging technique.
Figure 49B:
Figure 49C:
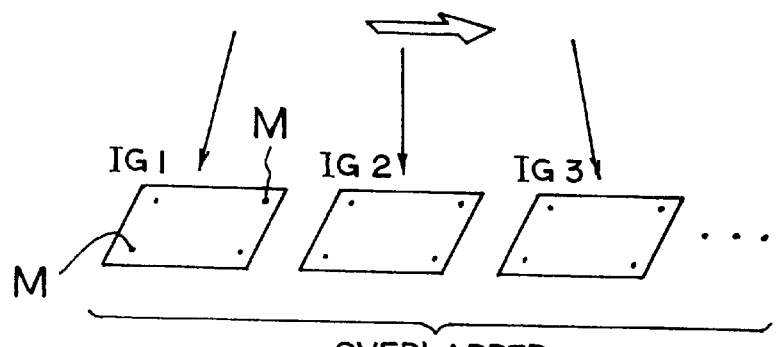

As an example, as shown in FIG. 49A, X-ray paths are scanned a plurality of times along the body axis direction of a patient P as both the tube and the detector are moved along circular scan orbits. On the tabletop of the couch, markers M are put. The position in each time of scan is set to always include markers which have been duplicated during its neighboring scan. Hence, as shown in FIG. 49B, recombined images IG1, IG2, . . . are produced according to the scans, and those images are then synthesized in a partly overlapped manner so as to have the marker positions coincide with each other between the adjoining frames. In consequence, as shown in FIG. 49C, a larger sized view of tomogram is produced along the body axis direction, which enables an easy interpretation of running of blood vessels, for example.

Marking means used for synthesizing through overlapping not necessarily restricted to ones put on the tabletop;

Alternatively, objectives themselves, such as blood vessels, are traced and used for positioning for the foregoing synthesizing technique.

Figure 49D:
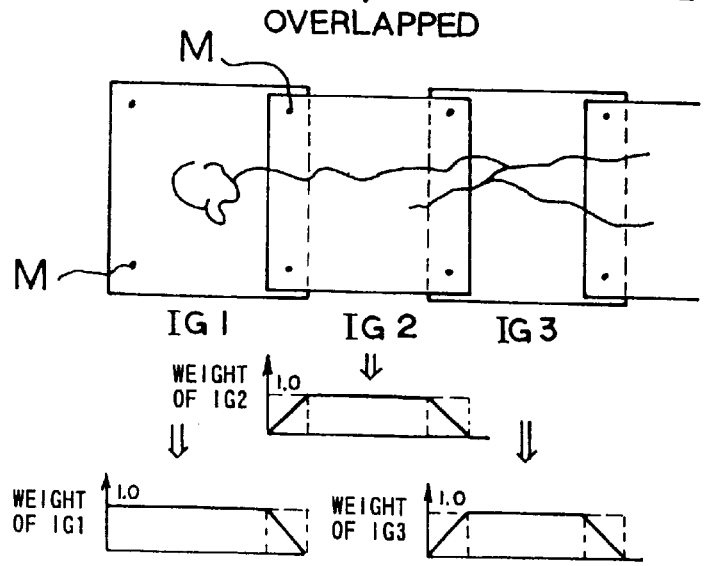

Additionally, in the foregoing large view imaging, it is also possible that an overlapped part between two images is weighted and added, in which time its weighting coefficients are smoothly changed, as shown in FIG. 49D, suppressing disturbances in the conjunctions of images.

8.8. Employing Averaging Process

Provided as an alternative feature in image recombination is an averaging process. Instead of a simple adding process, using the averaging process provides suppression of unevenness in pixel densities occurring owing to differences in the number of times of addition.

8.9. Image Recombination With Selected (Limited) Range

Still an alternative feature is to select or limit the range of objective projection data for image recombination. This feature comes from a fact that projection data of a plurality of frames each different in X-ray path angle passing each voxel in a desired slice are enough for the image recombination. This feature is also effective in a dynamic imaging method. This feature is realized, for example, during the image recombination process executed by the control/processing apparatus 18.

8.9.1. Use of Part of Acquired Data

Figure 50A:
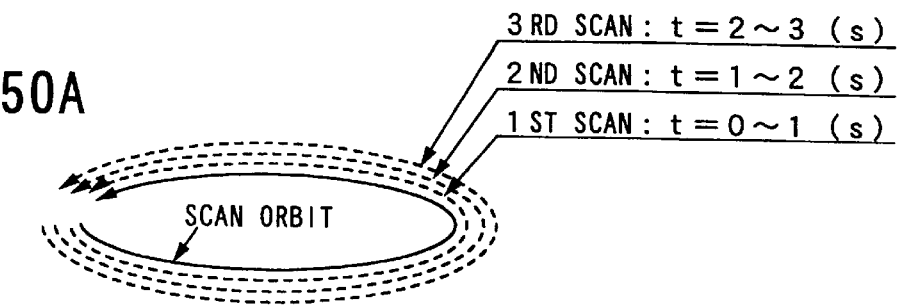
FIGS. 50A to 50D explain one example of an image recombination process with selected (limited) ranges.

Examples of this image recombination with a selected (limited) range are shown in FIGS. 50A to 50D. For example, it is assumed that, as shown in FIG. 50A, the tube and the detector are both moved along eliptic orbits, which are the same in size, so that one time of scan is executed as they revolve along the orbits a plurality of time. And assume that it takes one second for one time of revolving, for instance.

Figure 50B:
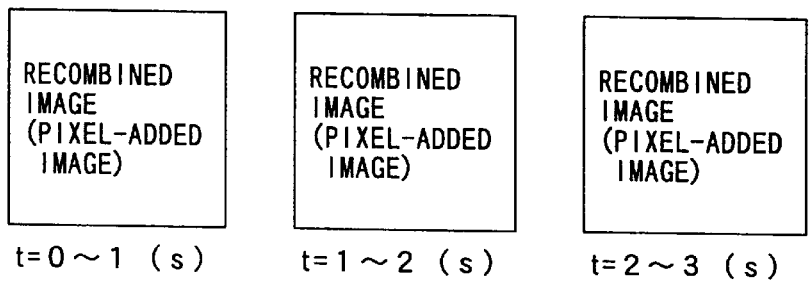

As shown in FIG. 50B, one image is recombined from a plurality of frames of projection data acquired by scanning carried out during each revolving movement. For example, each tomogram is obtained during the first revolving movement (time t=0 to 1 sec.), the second revolving movement (t=1 to 2 sec.), the third revolving movement (t=2 to 3 sec.), etc.

Figure 50C:
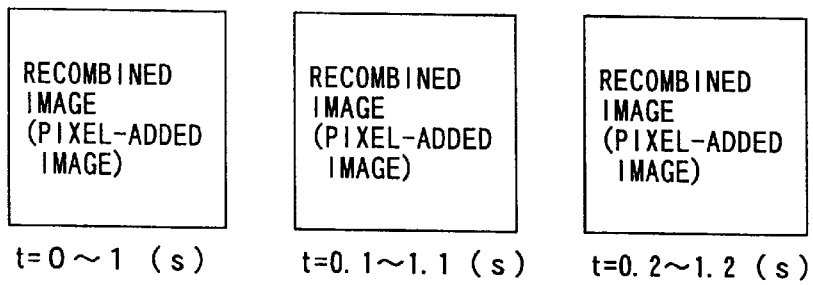

Alternatively, as shown in FIG. 50C, the similar image recombination may be applied to another time pitch between tomograms. Practically, scanning during the first revolving movement (time t=0 to 1 sec.) leads to one recombined tomogram, which is then followed by a changed time pitch t=0.1 to 1.1 sec. which leads to the next one recombined tomogram. Further, the time pitch is altered to t=0.2 to 1.2 sec., during which scanning produces projection data which lead to the next recombined tomogram. Altering the time pitch between images in this way can change temporal resolution among images.

Figure 50D:
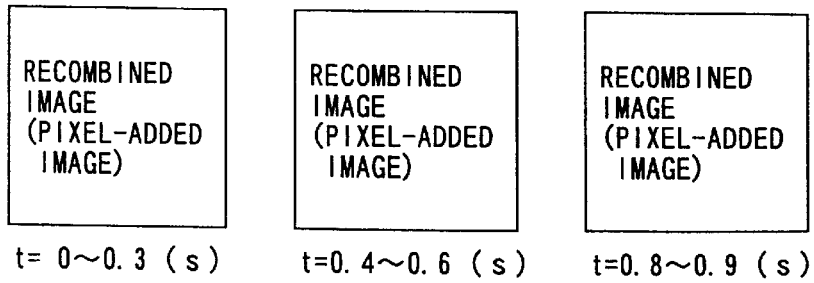

Further, as shown in FIG. 50D, the similar image recombination can be applied to a technique that alters the time pitch for each image. For instance, the first tomogram is recombined from a plurality of frames of projection data acquired during an interval t=0 to 0.3 sec., then the second one from those data acquired during another interval t=0.4 to 0.6 sec., and the third one from those data acquired during still another interval t=0.8 to 0.9 sec., and the like. Altering the time pitch in this manner can change temporal resolution of each image. This time pitch is arbitrarily selectable.

8.9.1.1. Use of Partial View

Figure 51:
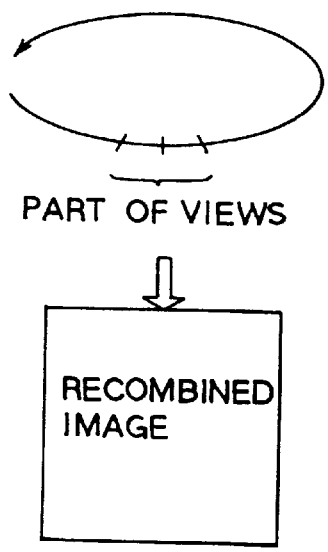
FIG. 51 explains another example of an image recombination process with selected (limited) ranges.

The above example shown in FIG. 50D can be interpreted such that a plurality of frames of projection data acquired in only partial views of the entire ones accomplished during one time of revolving movement. This state can conceptually be illustrated by FIG. 51.

8.9.1.2. Use of Partial Projection Data

Figure 52:
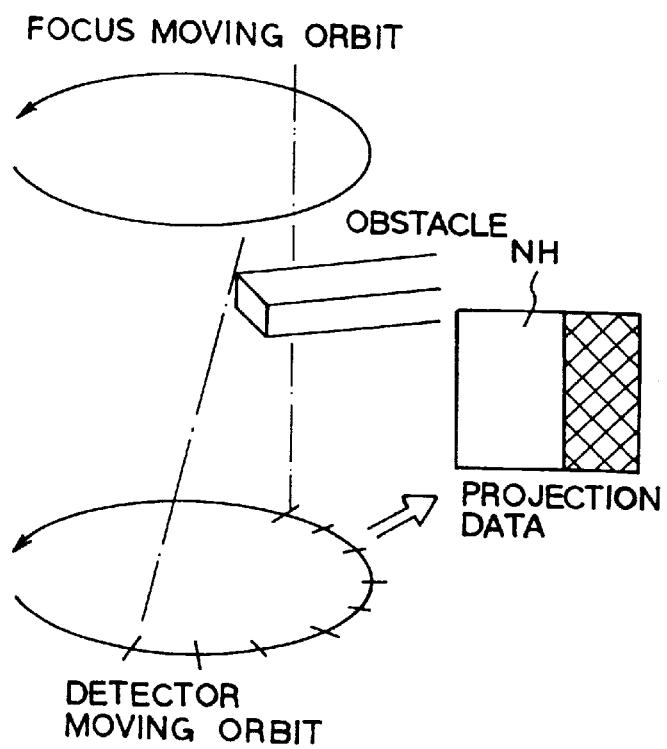
FIG. 52 explains still another example of an image recombination process with selected (limited) ranges.

Still an alternative example is exemplified by FIG. 52, which shows a situation where the tube and the detector move along given scan orbits, during which scanning obstacles (such as arm edges of supporting mechanisms for the tube and/or detector, structures including the patient's bones, or the like) come into the view. In such a case, partial projection data acquired in a particular region on the detector orbit surely include the data of projected obstacles, while there exist are remaining projection data which do not include those data of obstacles. (Refer to a non-hatching part NH in FIG. 52.) Thus recombining only partial projection data NH permits tomograms to be produced freely from obstacles.

8.9.6. Changes According to Slice Position

Another example is provided by a technique that the range selected (limited) in the above recombination may be changed according to slice positions.

8.9.3. Gradually-shifted recombination

An alternative example is constructed such that temporal regions acquiring projection data are shifted on the time axis little by little, during which time the same slice is recombined or a volume region consisting of a plurality of slices is recombined (refer to FIG. 50C.).

8.9.3.1. Adjustable Temporal Resolution

In the above gradually-shifted recombination, the method of adjusting temporal resolution between images or images may be available (refer to FIGS. 50C and 50D.).

8.10. Replicate Convergence Method

An alternative feature in respect to the image recombination process is are replicate convergence method. This method is performed such that either a series of reprojection processes based on differentials, recombination, and to calculation of differences for each voxel (i.e., artifacts), or, a series of reprojection processes based on differences, calculation of differences for each voxel, and to recombination are repeated until when each differential converges to a given value or less, at which time the recombined image is treated as a true and desired image.

8.11. Subtraction with Correction for Movement

This feature is concerned with a subtraction method preferable to compare sliced tomograms to each other before and after the operation, for example. While the foregoing slices are set to be specified in the absolute coordinate system, the subtraction method with correction for movement introduces a system where a slice of a subject is considered to be the center thereof. Thus, on the basis of moving amounts and/or twisted amounts is positionally detected along the body axis direction of a subject, or, on the basis of landmarks made up of markers put on a subject or characteristic positions such as patient's bones, specified slices are moved by values corresponding to movement to recombine projection data of the slices. The two slice images thus-recombined are subjected to mutual differential operation pixel by pixel, providing a ready technique which requires changes between two images acquired, for example, before or after the operation.

9. Image Processing, Image Cutting-out, and Post Correction

Features and examples falling into the category of "image processing, image cutting-out, and post correction" will now be described. Those features and examples can be realized by the control/processing apparatus 18.

9.1. Cutting-out From Volume Data at Arbitrary Angle

This feature is to cut out two dimensional tomograms from volume data at arbitrary angles at which tomograms are sliced. As has been described, a three dimensional set of volume data are made by specifying a plurality of slices such as coronal planes and recombining each of the slices. Performing a multi-planar reconstruction (MPR) on the volume data at a specified angle provides images at any cross section such as an oblique image. If an angle along which a cross section is specified properly, axial and sigittal images can also be obtained.

9.2. Panoramic Development

This feature relates to a panoramic cross section, not planar plane. In specifying an arbitrary cross section within the volume data obtained in item 9.1., specifying information including a curvature, a center of curvature, and an angle of circular arc leads to specification of a panoramic curved cross section. When performing a multi-planar reconstruction process on the curved cross section, a panoramic curved tomogram can be produced (i.e., panoramic development). This imaging is useful for treatment of gingiva in dental clinics, for example.

The processes described in the above items 9.1. and 9.2. are not only limited to be used as postprocessing. When a plurality of frames of projection data are recombined, those processes can be applied to direct production of images along arbitrarily-angled cross sections or along panoramic curved cross sections.

9.3. Tracing and Cutting-out Objective

This feature is to cut out images along a free plane tracing an object, such as blood vessels in the lungs. Setting such a free plane within a set of volume data produced by recombination of each of a plurality of slices and performing a multi-planar reconstruction provide two dimensional tomogram along such plane.

9.4. On-demand Processing/plan Processing

This feature is concerned with an MPR-based image cutting-out process executed on demand from an operator or an a predetermined plan. On-demand processing is executed such that as observing an image cut out from volume data through MPR, when an operator sends out instruction demanding "adjacent plane", an image is produced by MPR at its adjacent slice parallel-moved by a minute distance in a predetermined direction, or when sending out instructions demanding "rotate by specified degrees", an image is produced in the same way at a slice rotationally-moved by a minute angle in a predetermined direction. The same procedures as the above may be done on planned processing

9.5. Removal of DC Blur Components

An alternative feature is removal of a kind of noise called DC blur components, of which intensities are usually low and vague, and entirely superposed on recombined images.

Since the production process of tomograms employed herein is based on addition of projection data, as described before, it is unavoidable that an objective slice data absolutely includes other slice components as DC blur components. The DC blur components reduces the contrast of an objective image. Hence, DC blur components are to be removed as much as possible.

One example is that a reference slice whose constituents are known, such as a slice in the air above or under a patient or a slice in the couch, is specified, and the image of the reference slice is recombined. Slices set in the air are set by one or more, as shown by N1 to N5 and M1 to M5 in FIG. 53A.

Using data of a distribution of X-ray intensities at specified one or more positions in recombined images of the reference slices, DC blur components of an objective slice area presumed and their correction values are calculated. For example, it is supposed that a distribution of X-ray intensities in the one dimensional X-axis direction at a specified two dimensional position (Y, Z), which are presumed from a plurality of reference slices set in the air is expressed as in FIG. 53B. In this case, an intensity $I=I1$ corresponding to a position $X=X1$ in an objective slice become DC blur components thereof. This kind of X-ray intensity distribution may previously be memorized, or may be calculated each time when the removal calculation is performed. Alternatively, without using the X-ray intensity distribution, DC blur components may directly be obtained by correcting calculation using recombined image data of slices.

Figure 54:
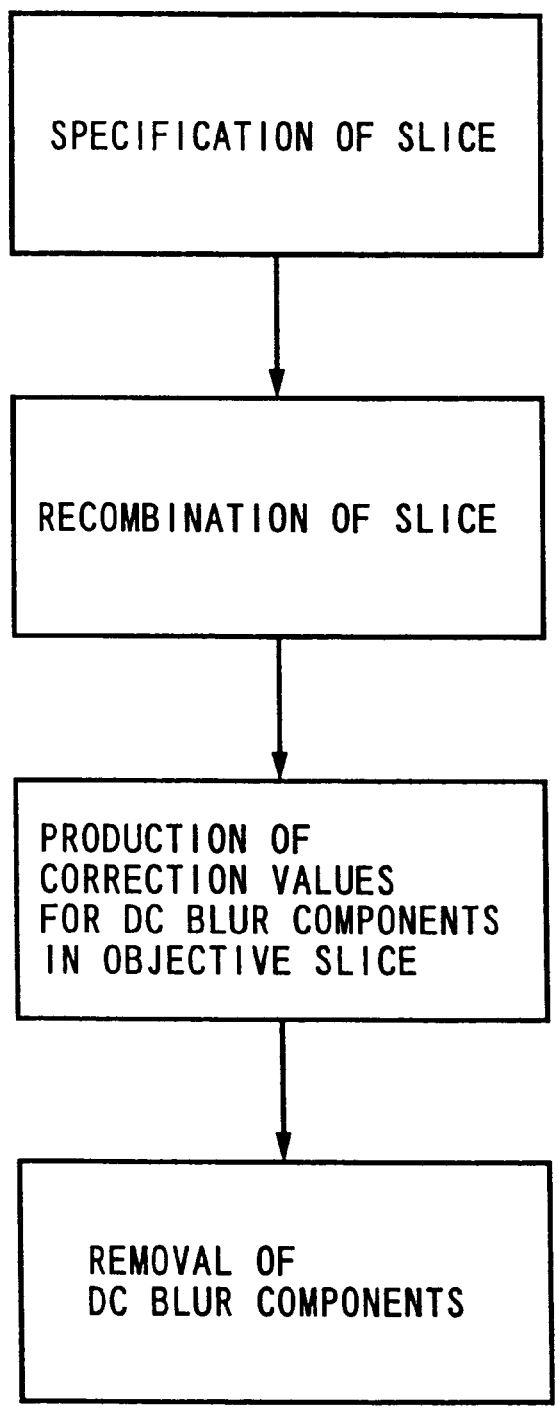
FIG. 54 is a flowchart showing a conceptual procedure of removal of DC blurry components.

The correction values are deducted from each pixel value of an objective slice for removal of DC blur components. A schematic concept for this removal process is shown in FIG. 54, which is executed by the control/processing apparatus 18 as a postprocess which follows projection data acquisition and image recombination processes.

The correction values may be produced for each pixel of an objective slice to perform the removal calculation for each pixel. Alternatively, one correction value can be obtained for each frame image.

9.5.1. Utilization of a Plurality of Reference Slices

As a practical example, it is preferred to obtain DC blur components utilizing recombined images of a plurality of reference slices. This example can increase reliability for the correction.

9.5.1.1. Utilization of Non-linear Correction

When recombined images of a plurality of reference slices are utilized, those image data may be non-linear corrected to obtain correction values.

9.5.2. Utilization of Two Reference Slices

Figure 53A:
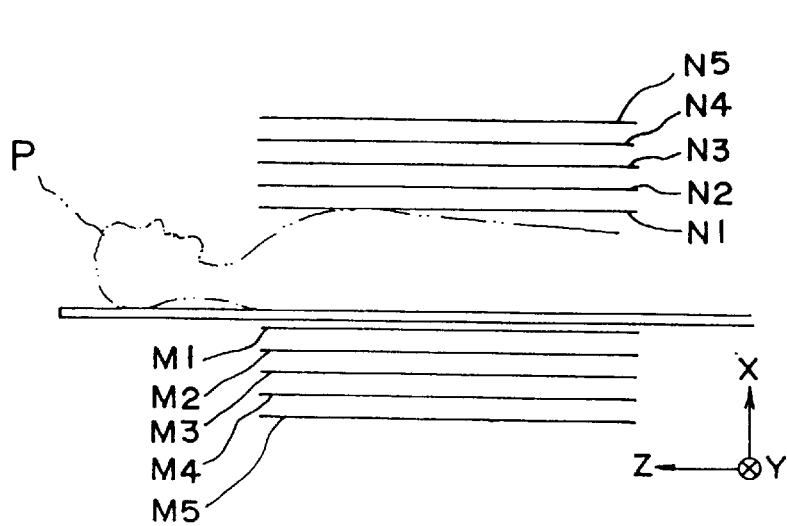
FIGS. 53A to 53B are illustrations for explaining DC blurry components.
Figure 53B:
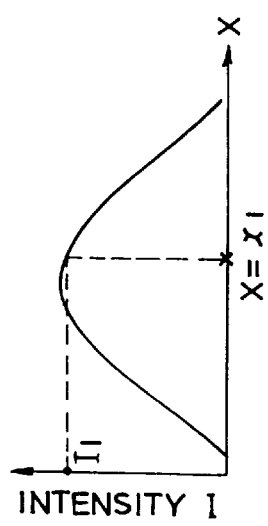

Another preferable example is that two reference slices positioning in front and back of a laid patient, for example, N1 and M1 (or N2 and M2, or N1 and M2) in FIG. 53A, are utilized for the correction.

9.5.2.1. Linear Correction

When utilizing two reference slices as above, their recombined data can be linear-corrected, which enables an each presumptive calculation of the X-ray intensity distribution in the X-axis direction (including correction values of DC blur components for an objective slice), or correction values of DC blur components for an objective slice.

9.5.2.2. Multiplication of Coefficient

It is also preferable that final correction values are obtained by multiplying the linearly-corrected X-ray intensity distribution(profile) in the X-axis direction, or correction values of DC blur components of a objective slice by coefficients taking account of the position of an objective slice and imaging conditions.

9.5.3. Utilization of One Reference Slice

Further, there is provided a technique which can simplify correcting calculation procedures. That is to utilize only one reference slice, which locates in front or back of a laid patient. For example, in FIG. 53A, it is a front-side one slice N1 (N2, N3, etc.) or a back-side one slice M1 (M2, M3, etc.).

9.5.3.1. Utilization of Reference Slice Data

A practical example is that recombined image data themselves of one reference slice are employed as correction values. In this case, the correction values can be calculated for each pixel, or one correction value can be calculated for the entire image.

9.5.3.2. Multiplication of Coefficient

Another practical example is to obtain final correction values by multiplying recombined image data of one reference slice by coefficients considering the position of an objective slice and imaging conditions. In this case, the correction values can be calculated for each pixel, or one correction value can be calculated for the entire image.

9.6. Three Dimensional Filtering Process

Although the above features have been for DC blur components, a feature which will be stated in this item is to remove the entire blur components by using three dimensional filters.

9.6.1. Enhancing Filter (Blur-recovering Filter)

Figure 55:
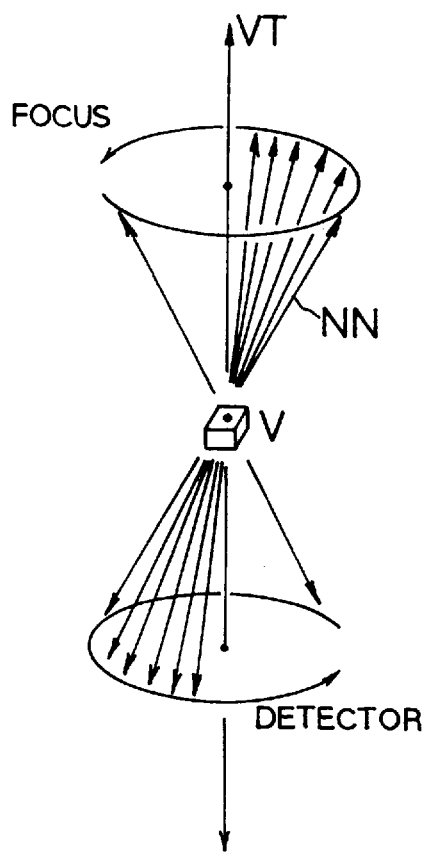
FIG. 55 explains directions of filtering executed for recovery of blurry components.

The principle of this imaging can also be interpreted into another way that each voxel component in a slice is pressed out along the directions of X-ray paths, which causes blurring in the X-ray path directions. For instance, as shown in FIG. 55, when the focus and the detector both trace circular scan orbits, a certain voxel V in a slice is made blurred along the oblique directions NN shown in FIG. 55. Hence filters correcting this blurring, which consists of enhancing three dimensional filters (referred to as blur-recovering filters), are used.

9.6.2. Isotropic Filter

As this enhancing three dimensional filter, an isotropic filter can be used.

9.6.3. Anisotropic filter

Also anisotropic filters, which have characteristics operating filtering in only a specified direction, are used as the enhancing three dimensional filter.

9.6.3.1. One Way Filtering

As the specified direction, for example, the vertical direction VT in FIG. 55 can be regarded as a representative for all the X-ray paths. The filtering direction is therefore set in agreement with the vertical direction, resulting in a favorable blur removal.

9.6.3.2. Filtering Along X-ray Paths

An alternative example of the specified direction is each oblique X-ray path direction NN shown in FIG. 55, for example. Filtering is performed along each X-ray path, making sure of a highly accurate removal of blurs.

9.7. Three Dimensional Process

For image processing, a wide variety of three dimensional image processes and displays, including volume rendering, MIP (Maximum Intensity Projection), surface rendering, and reprojection, are available.

10. Multiple Modalities

Features and examples classified into the category of "multiple modalities" will now be described. The "multiple modalities" referred herein means that an X-ray tomosynthesis system according to the invention is combined with other modalities, such as an X-ray CT scanner and MRI (Magnetic Resonance Imaging) system. In a multiple modality system, it is an object that each modality makes the best use of its characteristics and compensates for each other, thus satisfactorily meeting the demands in clinical fields.

10.1. Positioning of Coordinate System With Other Modalities

One feature of the X-ray tomosynthesis system is that positioning is very simplified. Markers different in X-ray transmittances from a subject are put on a subject before scanning. Because the markers are duplicated into a recombined image, positioning with other modality's coordinates can be done using the marker positions in the image. One specific example is to rotate and/or move the recombined image so that the markers in the image not only uniquely determines the coordinate system of the subject but also positionally coincide with other markers in images acquired by other modalities. Thus, images acquired by different types of modalities can be located to each other in the same coordinate system.

10.1.1. Number of Markers

As one specific example is provided such that the markers are equal I the number to unknown variables. Normally, three markers are used.

10.1.2. Position of Markers

An alternative example relates to the positions of markers. When putting markers on a subject, their marker positions are determined to be duplicated only on edges of a reconstructed image. In general, the center portion of an image is clinically important. According to this example, the markers are not duplicated in the center portion, achieving recombination with less views in the number.

10.1.3. Utilization of Positioning

The above positioning is utilized in operation planning, radiotherapy planning, and perioperative navigation.

10.1.4. Positioning of Coordinate Input Apparatus

Particularly, positioning with a pointer (such as a pen) of a coordinate input apparatus used in the perioperative navigation can be performed. A region of a subject including a portion to have an operation is previously imaged by the X-ray tomosynthesis system to obtain a set of recombined image data or volume data. In operation, a marked portion of the subject is once pointed by the pointer, and the marked position (absolute position) is memorized. In this state, the pointer is used for pointing desired spatial positions within the subject. Based on this pointing, distances and directions between the pointed positions and absolute position are calculated. The calculated values are used to superpose the pointed positions on pixels included in the recombined image or volume data. The superposed positions are displayed together with an image. For example, under the operation drilling the patient head with, for example, a scalpel, when the surgeon observes the displayed image, he or she can visually recognize a presently-operated position (a position pointed by the pointer). This provides positional information helpful in operation, such as whether the scalpel should be advanced or not.

11. System Entire Operation

Features and examples falling into the category of "system entire operation" will now be explained.

11.1. Strobe Imaging Based on Pulsed Injection of Contrast Medium

A first feature is a technique that X-ray contrast medium is pulsedly injected, during which injection strobe imaging is performed. As a result, displayed images represent slowly running flows of blood as strobe photographes.

Figure 56:
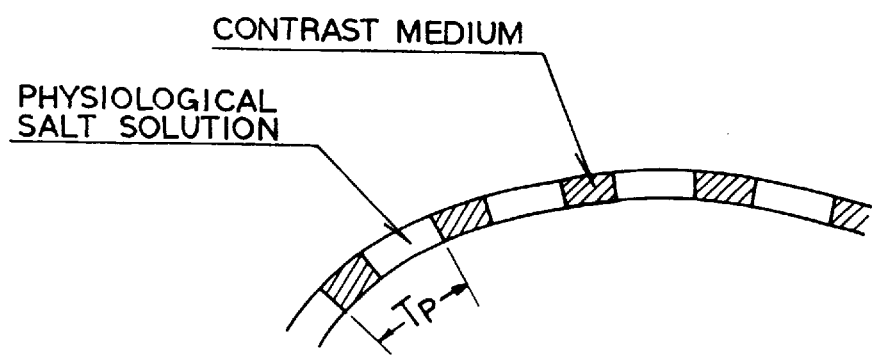
FIG. 56 pictorially shows the pulsed injection of contrast medium in a strobe imaging technique.
Figure 57:
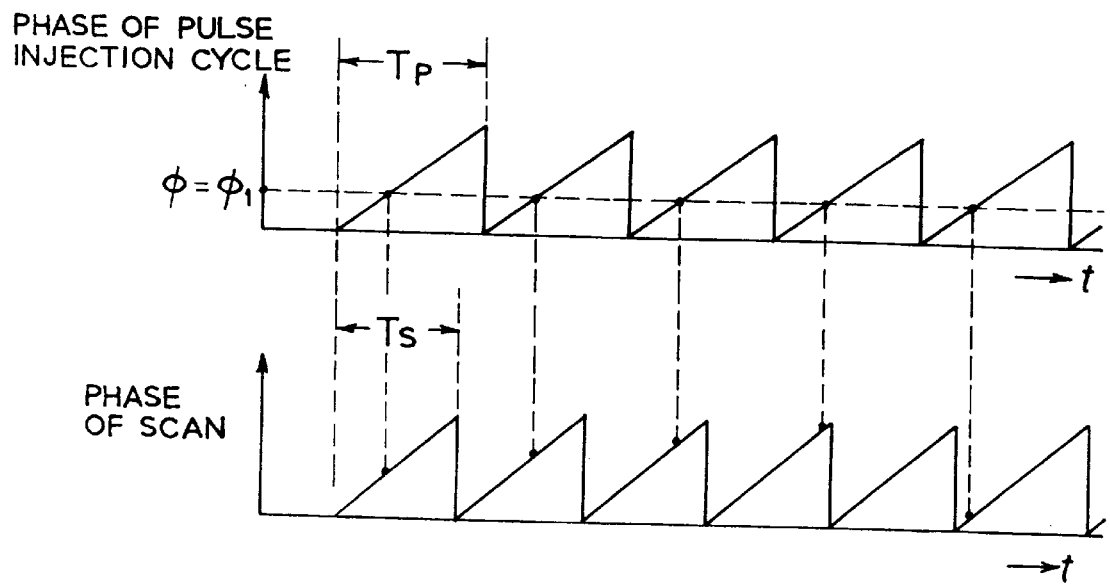
FIG. 57 is a timing chart showing the relationship between pulsed injection cycles of contrast medium and scanning cycles in the strobe imaging.

The strobe imaging is preferable to, for example, the head whose blood flow speeds are relatively slower. As shown in FIG. 56, contrast medium and physiological salt solution are alternately injected into a blood vessel. When this injection cycle (phase) is assigned to Tp, scanning is continuously performed at a rotation cycle of Ts slightly shifted from the injection cycle Tp. These cycles are exemplified in FIG. 57. From projection data resultant from this scanning, particular data existing at the same pulse injection cycle, which are, for example, data having a certain scan phase corresponding to the pulse injection cycle $\phi=\phi 1$ in FIG. 57, are selected. Recombining only the selected data produces a set of volume data acquired different scan phases.

11.1.1. Calculation of Blood Flow Speed

As one example utilizing this feature, blood flow speeds can be calculated based on the positions of the contrast medium at each scan time (phase).

11.1.2. Pulsed Contrast Imaging

One example preferable to the pulsed contrast imaging is a construction in which X-ray contrast medium and physiological salt solution have alternately been packed in a thin tube beforehand (refer to FIG. 56). For scanning, the loaded liquid is output at a specified pulse injection cycle described above.

11.2. ECG-gating Scan

Figure 58:
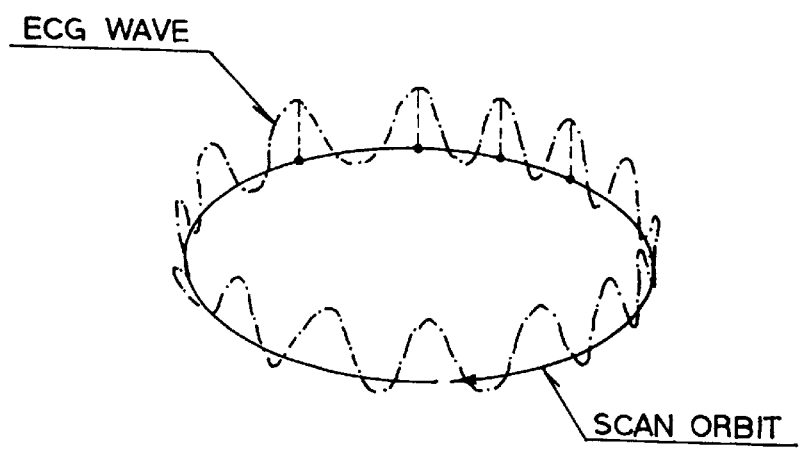
FIG. 58 explains a relation of the scan orbit and the ECG wave.

An alternative feature relates to an ECG-gating scan. In the case of a circular scan orbit, an electrocardiograph wave signal can pictorially be shown in FIG. 58 where the wave signal is together with the scan orbit. From this wave signal, only the data whose cardiac cycles are the same (for example, data only in the diastole) are selected to be recombined. That is, the pulse injection cycle described in the above strobe imaging is replaced by the cardiac cycle and only the data whose cardiac cycles are the same are used for image recombination.

11.3. Perioperative Navigation/perioperative Monitoring

Still an alternative feature relates to use as a perioperative navigator or perioperative monitor preferable to the stereotaxy etc. In such use, it is significant that which slice should be recombined to show it to the physician etc.

Figure 59:
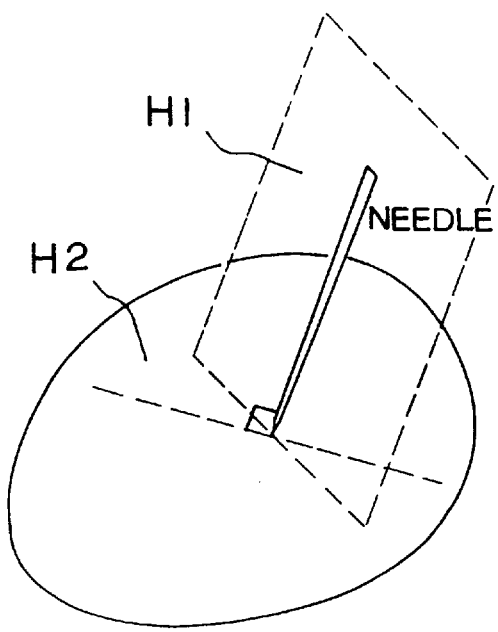
FIG. 59 is an illustration explaining a plane used for producing an image in perioperative navigation or perioperative monitoring.

Hence, in the system adopting this feature, a plane along which a needle is included (a plane H1 in FIG. 59) and/or another plane which passes the tip of the needle and is vertical to the needle (a plane H2 in FIG. 59) are subject to the production of their cross sectional images and their display. This image production can be done based on either of a technique directly recombining the above plane image (or images) from projection data which have been acquired by perioperative scanning, or a technique once performing recombination for a plurality of slices from projection data which have been acquired by perioperaive scanning and cutting out the above plane image (or imaged) through a planar conversion from the volume data. This enables an easy and quick determination of what exists a little ahead of the tip of the needle. By this perioperative navigation or perioperative monitoring, exact position information about, for example, whether or not the needle is allowed to go on can be provided timely and visually.

11.4. Quantification With Volume ROI

Figure 60:
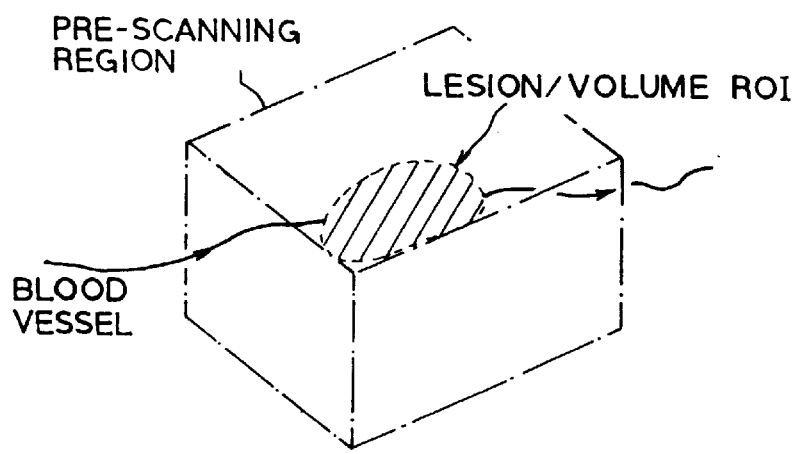
FIG. 60 exemplifies setting of a volume ROI.

An alternative feature about the system entire operation is provided by quantification of lesions using a volume ROI. For performing this method, 1) first, image recombination for a plurality of slices is performed on projection data which have been acquired by scanning preciously a patient region including a lesion, thus a set of volume data being provided. 2) As shown in FIG. 60, a three dimensional region of interest (ROI) referred to as a volume ROI is set in the volume data. 3) Next, contrast medium is injected into the lesion, during which injection a three dimensional region including the volume ROI is scanned a plurality of times. 4) For each scan, acquired projection data are recombined into each of a plurality of the slices to obtain data in the volume ROI. In consequence, a plurality of sets of blood density (voxel value) data each set of which constitutes the volume ROI are produced time-sequentially. 5) From these data, calculated is information representing time density curves or average passing times of contrast medium concerning the volume ROI.

Setting a volume ROI in this way, instead of a planar ROI, can easily provide time-density information of the entire lesion, making it possible a more quantitative dynamic observation of a lesion.

11.5. Filtering Process

Still an alternative feature is employment of a filtering process. In detail, this process is formed by combining a two dimensional filtering process for the projection data with a one dimensional filtering process for the voxel data obtained by the image recombination.

11.5.1. Filtering Direction

The above one dimensional filter is constructed such that its filtering direction is along, for instance, the tube-detector direction.

11.6. Threshold Processing

An alternative feature is a method of performing image recombination after projection data have been distinguished by a threshold. This feature can also be understood as a method developed from the non-linear processes described in the item 5.6.4. By setting a given threshold for projection data to cut off pixels having lower densities, image data can be compressed remarkably.

12. Others

Finally, features and examples relating to the "others" will be explained.

12.1. Employment of Various Techniques Practiced in X-ray Diagnostic System

Various techniques (such as gamma correction, image compression, automatic brightness control (ABC)) which have been practiced in the current X-ray diagnostic system can be employed, in principle. Hence, this X-ray tomosynthesis system achieves a higher performance.

12.2. Confirmation of X-ray Irradiation Field

Another feature relates to a construction capable of previously confirming an X-ray irradiation field in scanning.

Figure 61:
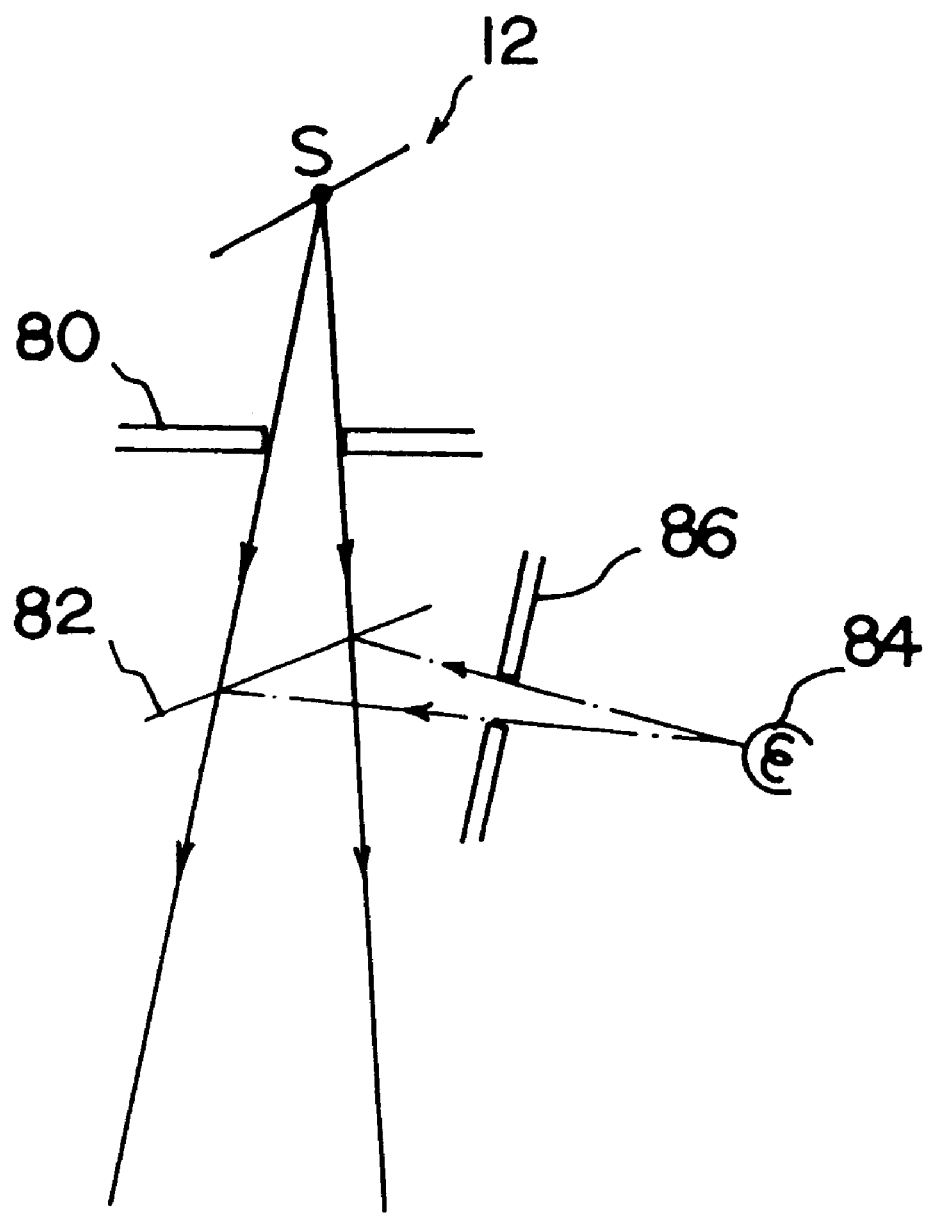
FIG. 61 is a conceptual view of a mechanism for confirmation of x-ray irradiation range by means of light.

As shown in FIG. 61, in the paths along which X-ray beams irradiated by the X-ray tube 12 are transmitted through an x-ray collimator 80, there is provided a mirror 82 which passes the X-rays therethrough, but reflects light. A light source 84 is placed at a geometrically symmetric position to the source S of the tube 12. Hence light beams emanating from the light source 84 reaches the mirror 82 through a light collimator 86 which is always kept in a constant correspondence in opening area and position to the X-ray collimator 80. Light beams which emanate from the light source 84 reflect on the mirror 82, then projected onto the subject body. The projected position and area are equal to those of X-ray beams irradiated during scanning.

Accordingly, light beams are made to emanate from the light source 84 at each view position prior to each scan. By this trial emanation, an actual X-ray irradiation field in scanning can be confirmed with only light, and according to the confirmation, the view position can be adjusted. This makes it possible to confirm an overall range of the actual X-ray irradiation field to be moved on the assumption that the tube and the detector are moved along specified scan orbits. Additionally, it is possible -to perform positioning that considers exposure to X-rays, such as that critical organs are avoided from being exposed.

The light system for confirming X-ray irradiation field may be of a combined unit with the X-ray irradiation system comprising the tube and X-ray collimator, or may be of a sole unit.

The various features and embodiments (examples) practicable to the X-ray tomosynthesis system according to invention are constructed and operate as described above.

One Example of Procedures of Imaging and Image Processing

For the foregoing system, one example of procedures from scanning to image processing is shown in FIGS. 62A to 62D. Assuming that at least one feature and/or embodiment (example) for each of the categories of "system design", "mechanism", "detector and tube", "scan orbit", "data acquisition", "data selection", "multiple modalities", "system entire operation", and "others" are selectively determined beforehand.

Figure 62A:
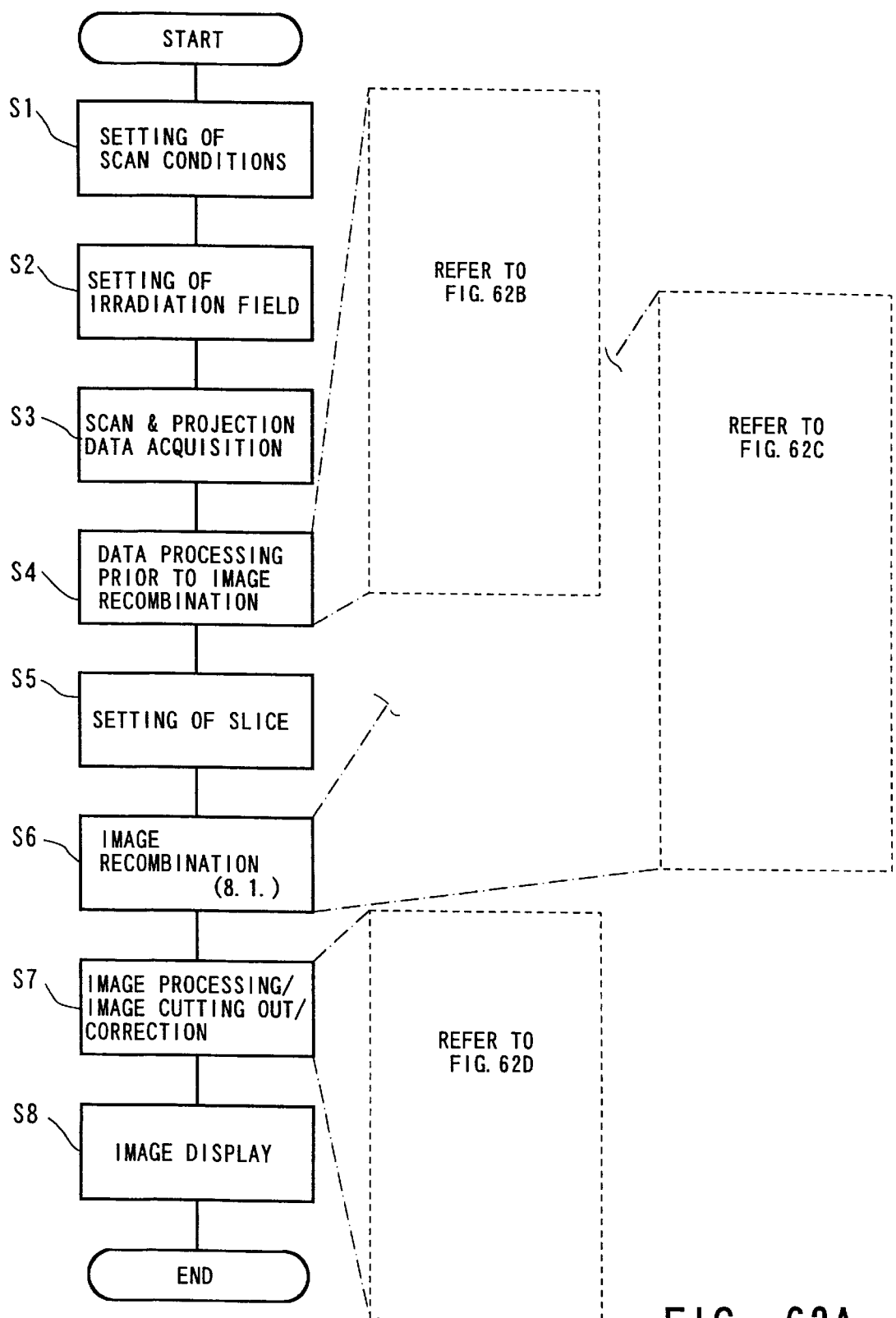
Figure 62C:
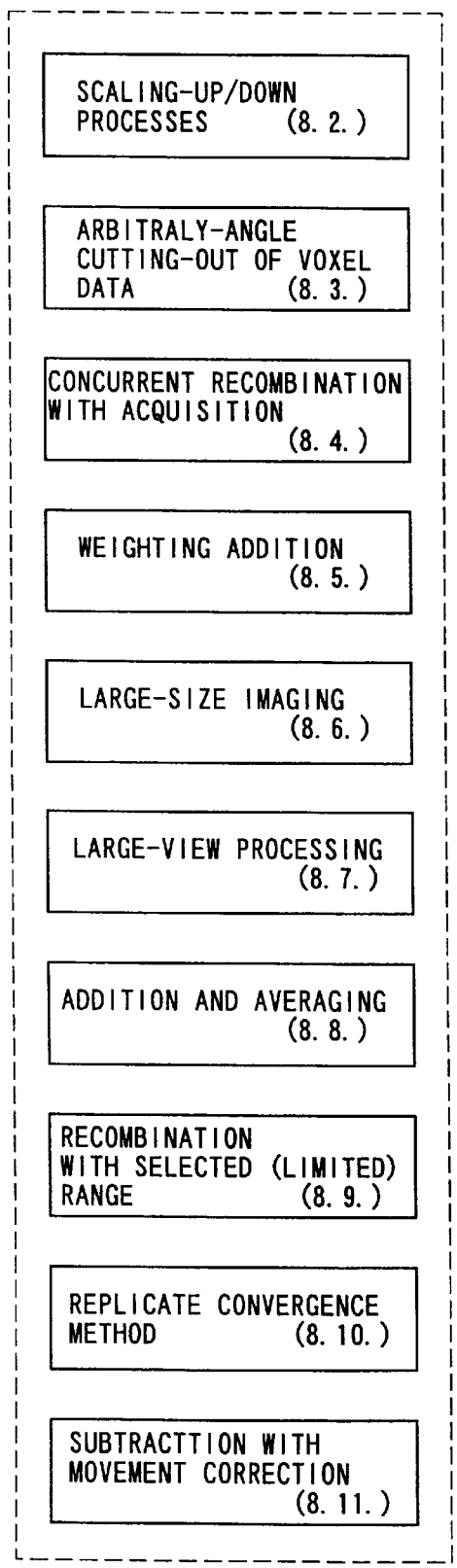

As shown in FIG. 62A, in step S1, such scanning conditions as a sliced region, slice thickness, the number of slice, tube voltage, tube current, scan orbit, and data acquisition method are given to the control/processing apparatus 18 by an operator. In step S2, in answer to an operator's command given via the input apparatus 19, an X-ray irradiation field is set by the apparatus 18. This irradiation field is confirmed based on, for example, the construction and method described in the item 12.2.

Next, in step S3, the control/processing apparatus 18 initiates scanning in answer to a scan-commanding signal from the input apparatus 19. In this scanning, the tube or a subject P(i.e., tabletop 10*a*) is at least moved along a specified scan orbit. Accordingly, in a plurality of views set on the scan orbit, projection data are acquired by the X-ray detector 14, and temporarily stored in the memory of the apparatus 18.

On completion of data acquisition, the control/processing apparatus 18 proceeds to the next step S4, where "data processing prior to image recombination" is executed. This processing is executed based on, for example, any one or more selected solely or selected in a combination form from the features (embodiments) described in the items 7.1. to 7.8. (refer to FIG. 62A).

Then instep S5, one or more slices are set by the apparatus 18 on the basis of information given by an operator via the input apparatus 19.

Then in step S6, from each of a plurality of frames of stored projection data, projection data required for image recombination of each voxel forming the specified slice are selected and added pixel by pixel to those voxels (i.e., recombined). This addition process is done based on a preferable embodiment described in the item 8.1. In addition, the "image recombination" process is possible to be combined with any one or more features (embodiments) described I the items 8.2. to 8.11. (refer to FIG. 62C).

Figure 62D:
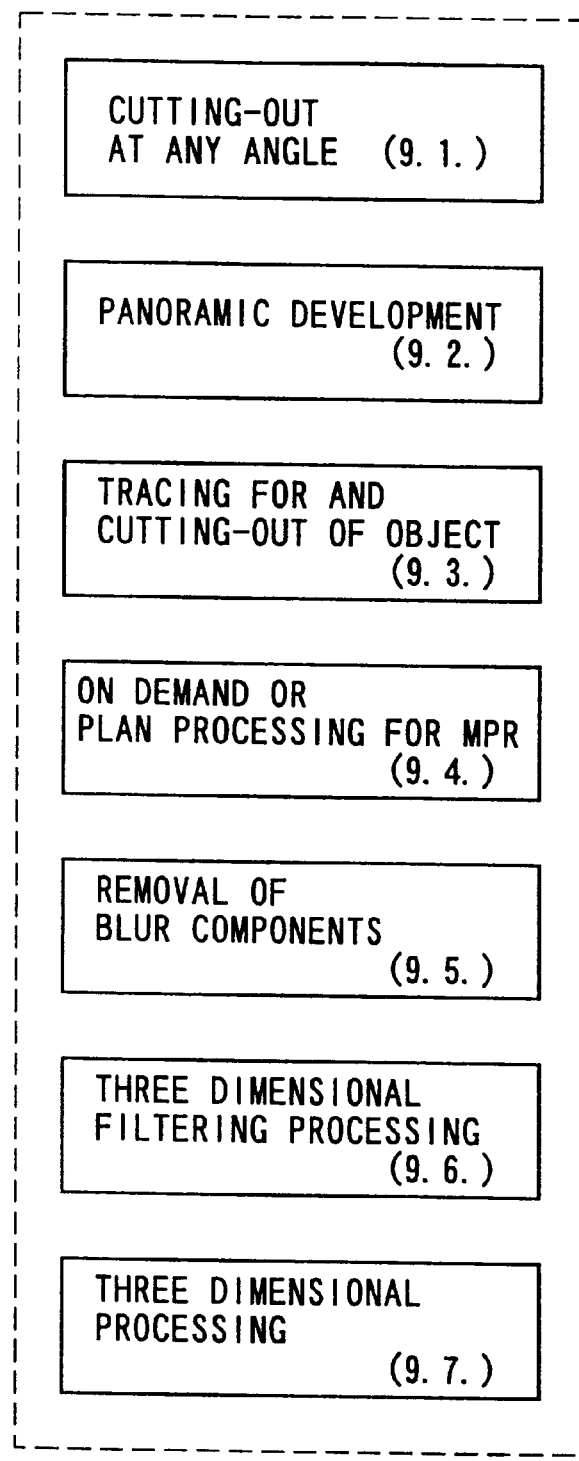

Then, proceeding to step S7, the, "image processing, image cutting-out, and post correction" are executed, in which processing any one or more features (embodiments) described in the items 9.1. to 9.7. are employed (refer to FIG. 62D).

If required, the "data processing" prior to image recombination" in step S4 and "image processing, image cutting-out, and post correction" in step S7 may be omitted from the entire processing.

Finally, in step S8, under the control of the control/processing apparatus 18, a tomogram recombined in step S6, or a tomogram processed, cut out, or corrected in step S7 is visualized by the display apparatus 20.

Therefore, compared to the conventional analog- and digital-types of systems, the foregoing tomosynthesis system has the following various advantages.

First, it is enough that the detector is fixedly positioned and only the tube is moved. Alternatively, it is also enough that both the detector and tube are not moved and only a subject is moved. This eliminates the need for an enforced synchronized movement between the detector and tube, unlike the conventional systems. As a result, deterioration in image quality of tomograms due to difficulties in the synchronization control can be avoided. Further a complicated control mechanism and control circuit for the synchronization control are unnecessary, lowering manufacturing costs.

Second, thanks to incorporating the correction means for positional shifts of the tube (focus), artifacts due to this positional shifts can be prevented or suppressed, increasing image quality.

Third, since the function capable of correcting or removing artifacts in association with the scan orbit patterns of the tube (for example, linear artifacts against a linear orbit) is included in the system, image quality can highly be improved.

Fourth, since countermeasures (such as scattered-ray correction, movement components removal, non-linear processing, and DC blur components removal) for contrast resolution which tends to be sacrificed due to the imaging principle are taken in, the contrast resolution is largely improved, and a higher visibility and diagnostic performance are given to tomograms.

Fifth, the processing of image recombination being generalized up to the three dimension and taking account of image enlargement ratios is executed. Accordingly, for example, even if coronal images acquired at a plurality of different slice positions are displayed in animation, there is no strange feeling for observation. There are provided images which improves visibility of lesions and efficiency of interpretation.

Sixth, compared to the conventional digital-type of X-ray tomosynthesis system, it is advantageous in that image data acquired from slices can fully be utilized. By way of example, such utilization includes image cutting out at arbitrary angles, image cutting-out along curved slices, strobe imaging, ECG-gating scanning, superposed display with positional information given by a coordinate input apparatus, perioperative navigation, or perioperative monitoring. These kinds of utilization can not only permit acquired data to be utilized effectively but also meet to various needs in clinical fields.

Seventh, differently from the conventional digital-type X-ray tomosynthesis system disclosed by the cited prior art, there is no limitation that the tube and the detector must be moved in opposite directions to each other. There is also no limitation that needs to memorize detected image information in association with each moved position. Even when the tube (or, the tube and the detector) is allowed to move, two- or three-dimensionally, image recombination can be realized. I this way, severe limitations concerning the scan orbit and data processing have been abolished, which can greatly enhance degrees of freedom of both the device allocation in designing systems and the image processing procedures. As a result, a highly generalized, easy-to-operate, and lower-cost X-ray tomosynthesis system is provided.

Second Embodiment

A second embodiment of the present invention will now be described in conjunction with FIGS. 63 to 66. This embodiment is practiced into an X-ray tomosynthesis system in which the movement of the tube and the detector is simplified for an easy image recombination.

Figure 63:
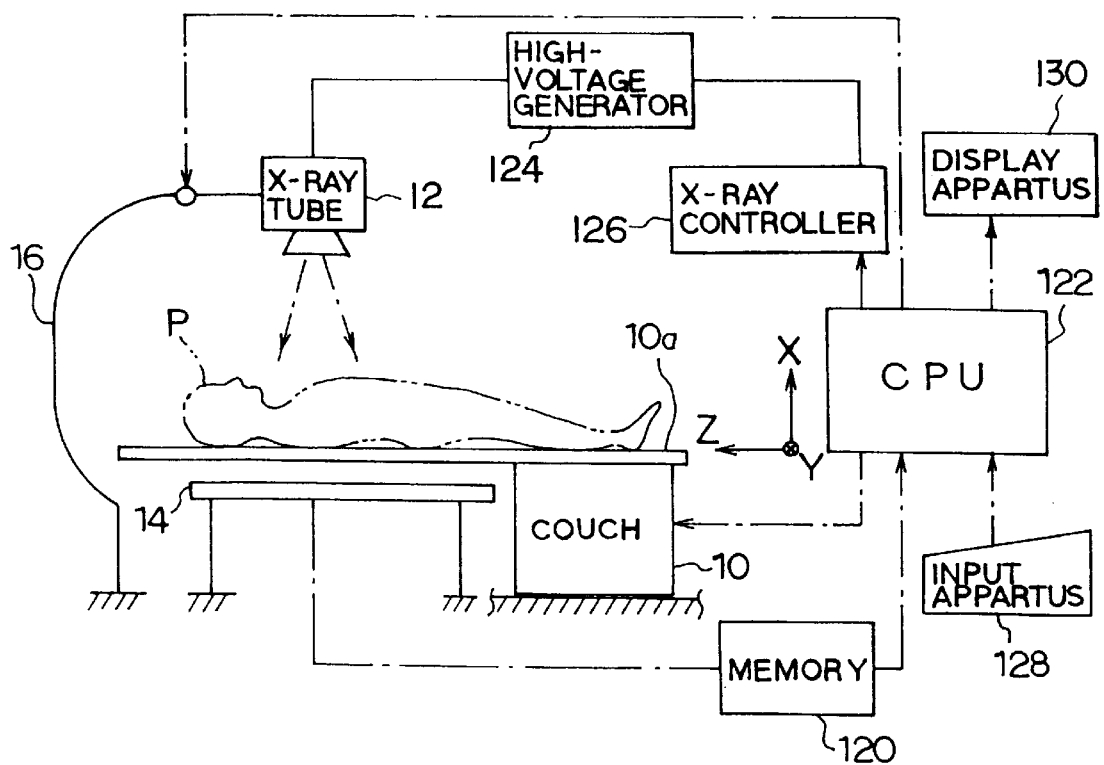
FIG. 63 is a schematic block diagram showing an X-ray tomosynthesis system according to a second embodiment of the present invention.
Figure 64:
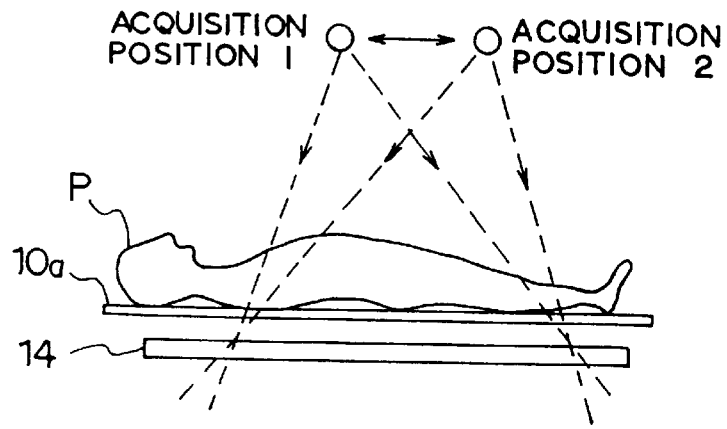
FIG. 64 illustrates a scanning method by which the detector is fixed but the tube is moved.

An X-ray tomosynthesis system shown in FIG. 63 is constructed such that the detector and a subject is fixedly placed in position and only the tube is allowed to move. More specifically, the X-ray detector 14 is formed into a large-size, direct-conversion, digital-type detector, and placed under the tabletop 10a, forming the detector under-arranged system. The term "large-size" used herein means a two-dimensional size which is capable of receiving all the transmitted X-rays in a plurality of views in a state that the detector are positionally fixed and the X-ray tube 12 is moved.

The X-ray detector 14 acquires projection data at intervals (for example, 100 times/sec.) and outputs them through a memory 120 to a CPU 122 serving as the control/processing apparatus. Thus, projection data of digital quantities acquired by the X-ray detector 14 is memorized by the memory 120.

The X-ray tube 12 positions above the patient P in the upper side in the X-axis direct ion and is supported by the moving mechanism 16 so that it is allowed to move, for example, linearly along a parallel plane to a specified slice. The X-ray tube 12 is formed into a type which can be switched between two modes of pulsed X-ray irradiation and continuous X-ray irradiation. The tube 12 is coupled with the CPU 122 via a high-voltage generator 124 and an X-ray controller 126. The CPU 122, which mainly takes in the entire system control and processing, incorporates therein an internal memory which holds control and processing procedures enabling predetermined processes, such as transmittance of X-ray control information to the controller 122, couch control, and image recombination. The CPU 122 is coupled with an input apparatus 128 and display apparatus 130 which can be used for interactive communication with an operator.

The operation of the system will be explained.

As the tube 12 (focus S) is moved along a specified scan orbit (for example, a linear scan orbit as in FIG. 64), X-rays are continuously irradiated. During this scanning, a plurality of N frames of projection data P(N, X, Y) are acquired by the detector 14. Those projection data are then stored frame by frame in the memory 120.

Figure 65:
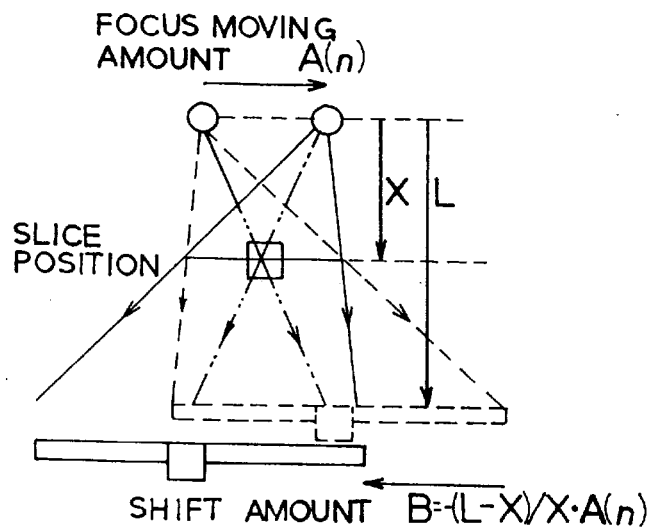
FIG. 65 illustrates shift amounts in the second embodiment.
Figure 66:
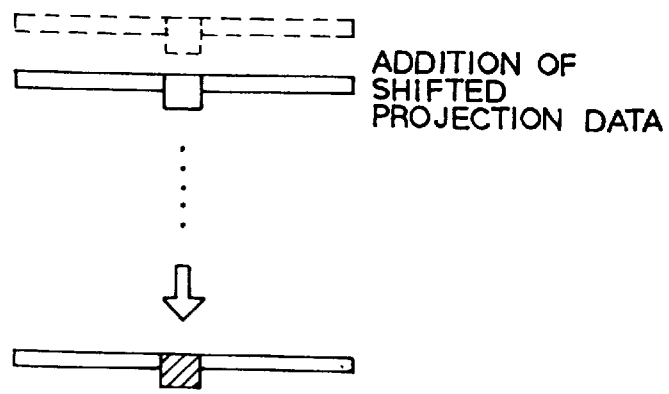
FIG. 66 illustrates addition of projection data in the second embodiment.

By the CPU 122, a plurality of N frames of projection data are read out from the memory 120, and amounts of pixel shifts necessary for image recombination are calculated frame by frame. Assuming that a focus moving amount is A(n), the distance between a focus moving plane along which the focus moves and a slice plane is X(slice position), and distance between the focus moving plane and the detector is L, as shown in FIG. 65, an amount B of the pixel shift is given by the following expression.

$$B(X, A(n))=-(L-X)/X \cdot A(n) \qquad (11)$$

The focus moving amount A(n) differs every frame. Thus, using reference positions such as a certain point in the coordinate system (for example, a focus position (for example, an initial position) in acquiring the first projection data, or an arbitrary coordinate position), or imaged positions of markers put on the patient body, the amounts of shifts are calculated as deviations from the reference positions. Alternatively, in order to obtain the focus moving amounts, such a detector as an infrared focus sensor or encoder may be attached to the system.

After having completed calculation of the shift amounts, a plurality of frames of projection data are positionally shifted by the CPU 122 in agreement with the calculated shift amounts B. And the positionally shifted projection data are mutually added (refer to FIG. 66) or mutually added and averaged. If the shift amounts, which changes every frame, are not integer times of a pixel size, a new frame of projection data may be produced by performing an interpolation process on the already-acquired projection data. By adding or averaging, data S1 of a tomogram recombined at a slice position X are obtained as follows.

$$i\ S1(X, Y, Z)=\Sigma(P\{n, Y, Z+B[X, A(n)]\})/N \qquad (12)$$

Thus, a tomogram is provided at a slice position X.

As understood from the above, in the case that the X-ray detector 14 is positionally fixed and the X-ray tube 12 is moved solely along a plane parallel to a desired slice, the recombination process to obtain the slice image becomes simplified. Furthermore, because only the X-ray tube 12 is to be moved, for example, along a linear scan orbit, its moving control is also simple, avoiding difficulties involved in a synchronized moving control for the detector and the tube.

In the above second embodiment, one time of scanning produces one slice image. However, a plurality of slice images are desired to be obtained from one time of scanning data, the variable X in the above calculation for obtaining the shift amounts should be replaced by X=X+ΔX. And this calculation is performed every slice and every frame. In the same way as the above, for each slice, projection data are pixel-shifted every frame in agreement with the shift amounts, and added pixel by pixel to the voxels of a desired slice. In this state, the enlargement ratios of slice images in the focus side become larger than those in the detector side. Namely, owing to the fact that the enlargement ratios differs depending on sliced positions, it is preferable to make them coincide with each other. From a set of volume data consisting of a plurality of slice images (such as coronal images) thus-produced in one direction, other images (such as axial, sagittal and oblique images) can be cut out along different directions through a technique of multi planar reconstruction (MPR). Accordingly, from projection data acquired by one time of scanning, a plurality of slice images are obtained concurrently, then other slice images are additionally produced through the MPR.

Still, in the second embodiment, a more simplified manner of processing and a faster recombination process can be achieved, which is particularly useful in mass screening. More specifically, a scan orbit of the focus, data acquisition timing of the detector, slice positions, and other parameters are preset, and shift amounts of projection data are also preset on the bases of such parameters. Under this setting, scanning is performed, during which time projection data are acquired for each view, those data are being immediately shifted, interpolated (if required), and added. This technique enables image recombination to be performed concurrently with data acquisition. A process for recombination is very simple, and an interval from scanning to recombination can be shortened.

Third Embodiment

A third embodiment of the present invention will now be described in conjunction with FIGS. 68 to 81A and 81B, an X-ray imaging system of the present invention is practiced into a single plane type of X-ray diagnostic system. Although this system has a total of five imaging modes consisting of "fluoroscopic/radiographic mode", "subtraction imaging mode", "tomographic mode", "reconstruction mode (without subtraction)", and "reconstruction mode of subtraction images", the system constructions of all the modes becomes too complicated to understand them when they are packed together in one drawing. Therefore, for the sake of an easy of understanding, the constructions for each imaging mode is separately depicted from FIGS. 68 to 71.

Construction Corresponding to Fluoroscopic/radiographic Mode

Figure 68:
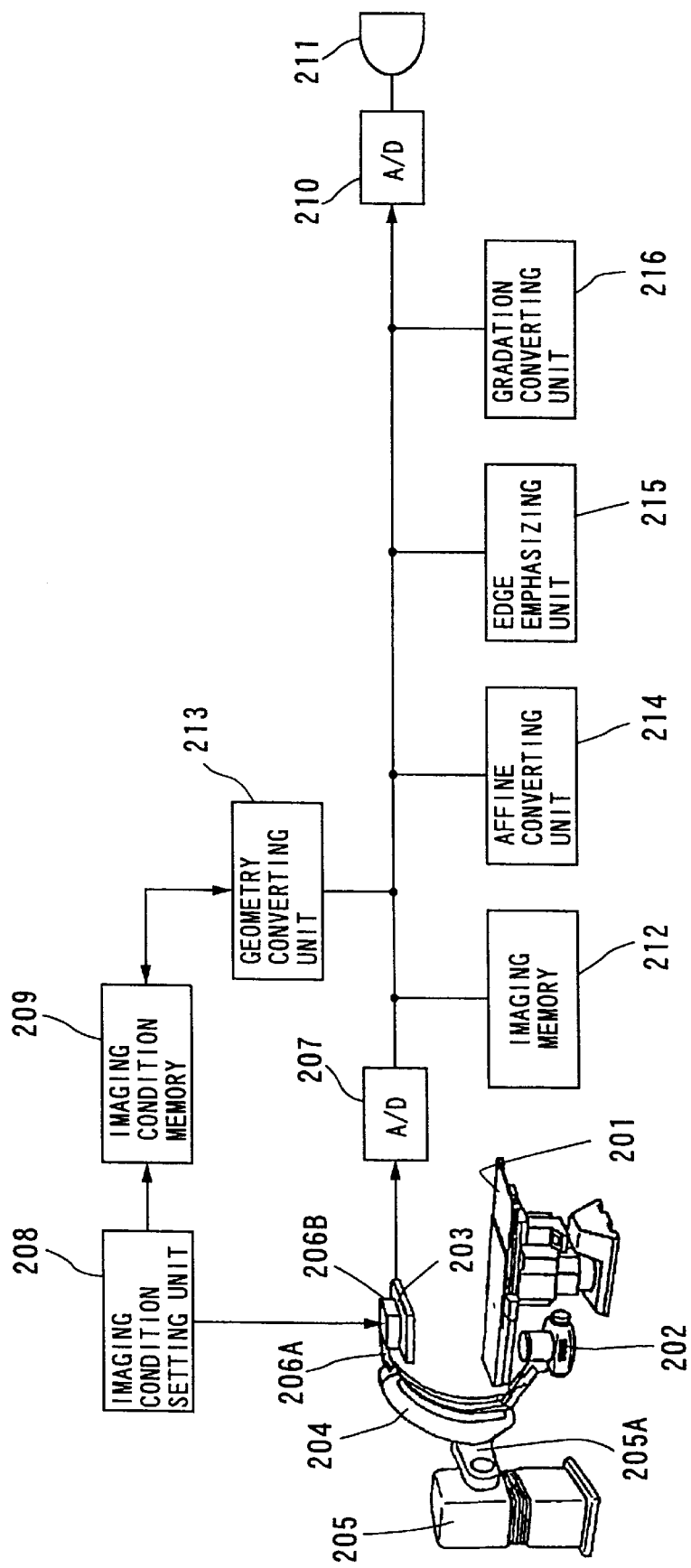
FIG. 68 is a schematic diagram of a single-plane X-ray diagnostic system, which corresponds to its fluoroscopic/radiographic mode, in a third embodiment according to the present invention.
Figure 69:
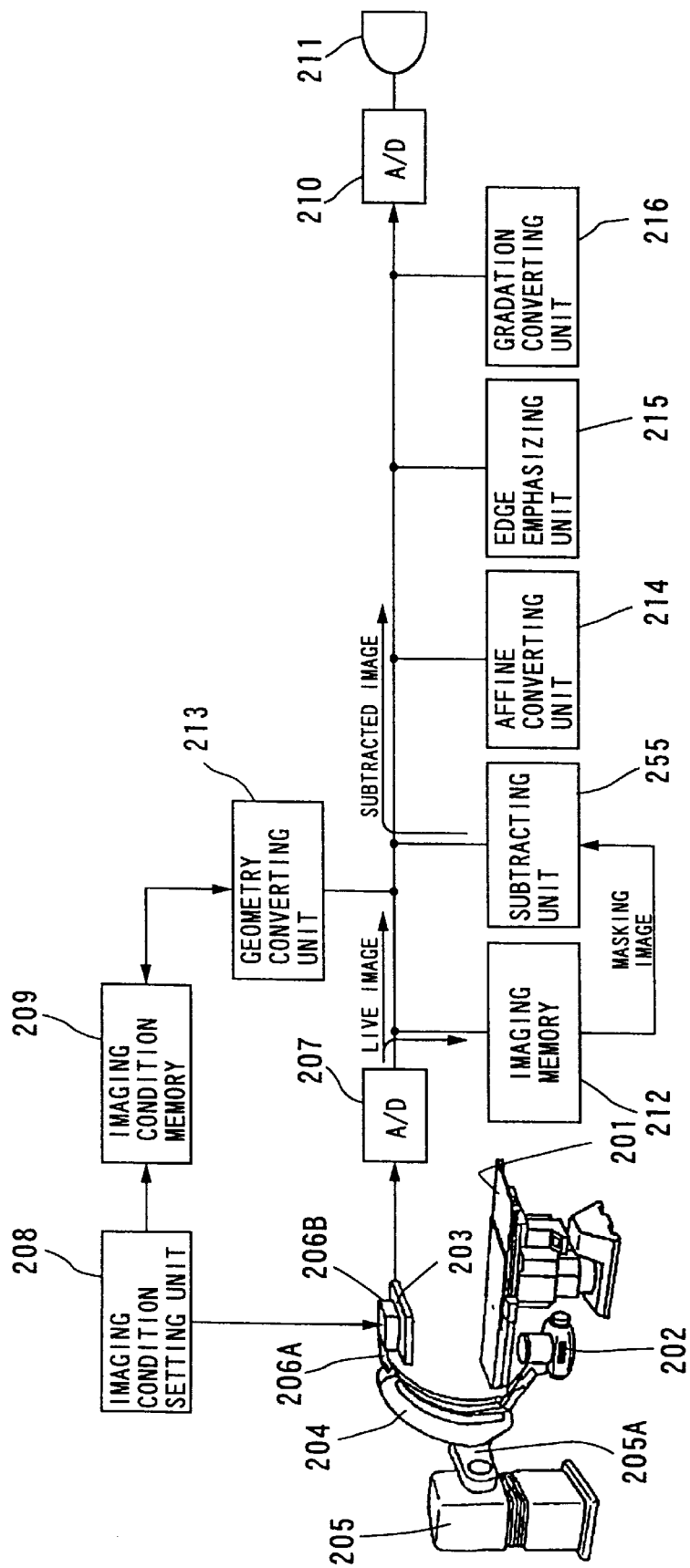
FIG. 69 is a schematic diagram of the X-ray diagnostic system, which corresponds to subtraction mode, in the third embodiment.
Figure 80A:
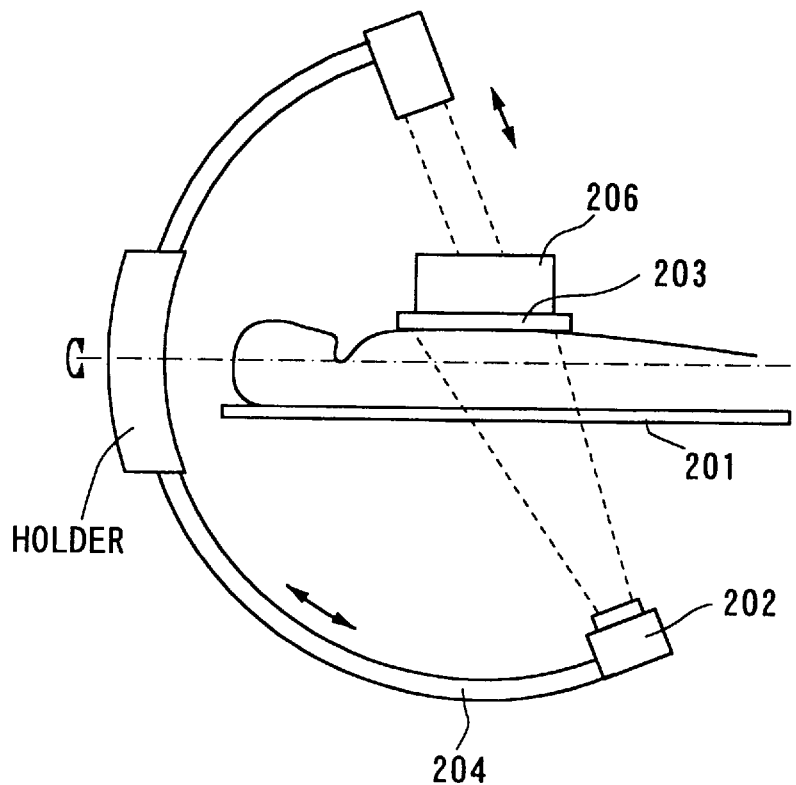
FIGS. 80A and 80B explain states where the planar-type X-ray detector is able to be contacted onto a subject by its rotationally driving.
Figure 80B:
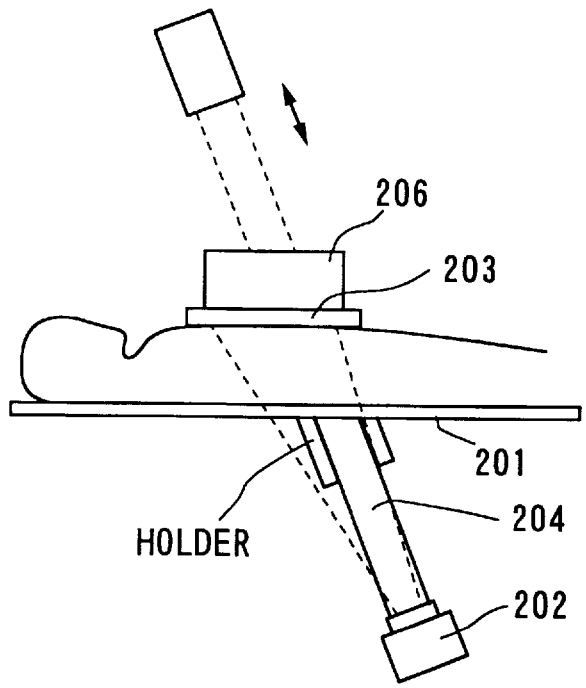

As for the construction corresponding to the fluoroscopic/radiographic mode, the X-ray diagnostic system comprises, as shown in FIGS. 68, 80A and 80B, has a couch 201, an X-ray generator 202, planar-type X-ray detector 203 as a two dimensional X-ray detector, a C-shaped arm, a shrinkable supporting member 206A, and a detector rotating mechanism 206B. The couch 201A is used to lay a subject thereon. The C-shaped arm has the X-ray generator 202 and the X-ray detector at both the ends, respectively. The shrinkable supporting member 206A, which is shrinkable, intervenes between the detector rotating mechanism 206B and C-shaped arm 204. The detector rotating mechanism 6, used for adjusting the incidence angle of X-rays by rotating the detector 3, is arranged between the detector 3 and C-shaped arm 204. The C-shaped arm 204 is supported by a supporting pillar 205. Between the supporting pillar 205 and the C-shaped arm 204 is provided a holder 205A which supports slide-rotatably the C-shaped arm 204 about its slide-rotation axis. This holder 205A is rotatably attached to the supporting pillar 205A about its rotation axis perpendicular to the slide-rotation axis.

Additionally, the X-ray diagnostic system comprises an A/D converter 207 digitizing analog type of imaging signals supplied from the X-ray detector 203 and outputting them, an imaging condition setting unit 208 setting mainly irradiating angles of X-rays, an imaging condition memory 209 memorizing data indicative of imaging conditions set by the setting unit 208, and D/A converter 210 converting imaging signals processed in the fluoroscopic/radiographic mode into analog quantities and sending them to a display 211.

Still, the X-ray diagnostic system comprises an imaging memory 212, geometry converting unit 213, and affine converting unit 214, all of which are connected with a signal line mutually connecting the A/D and D/A converters 207 and 210. The imaging memory 212 temporarily stores digitized imaging signals by the A/D converter 7. The geometry converting unit 213 performs a geometry conversion process (specifically, a trapezoidal conversion process) on the imaging signals stored in the imaging memory 212 according to the imaging condition data (specifically, the rotational angles of the detector 3) memorized in the imaging condition memory 209. Further, the affine converting unit 214 performs affine conversion processes to correct distortions of the imaging signals geometry-converted by the converting unit 213.

Still, the X-ray diagnostic system comprises an edge emphasizing unit 215 and a gradation converting unit 216, which are coupled to the signal line mutually connecting the A/D and D/A converters 207 and 210. The edge emphasizing unit 215 processes imaging signals distortion-corrected by the affine converting unit 214 so that edges of images are emphasized, using, for example, Laplacians (secondary differential operators. The gradation converting unit 216 adjusts contrast and brightness to control luminance and a steady feeling of images.

Construction of Detector

Figure 72:
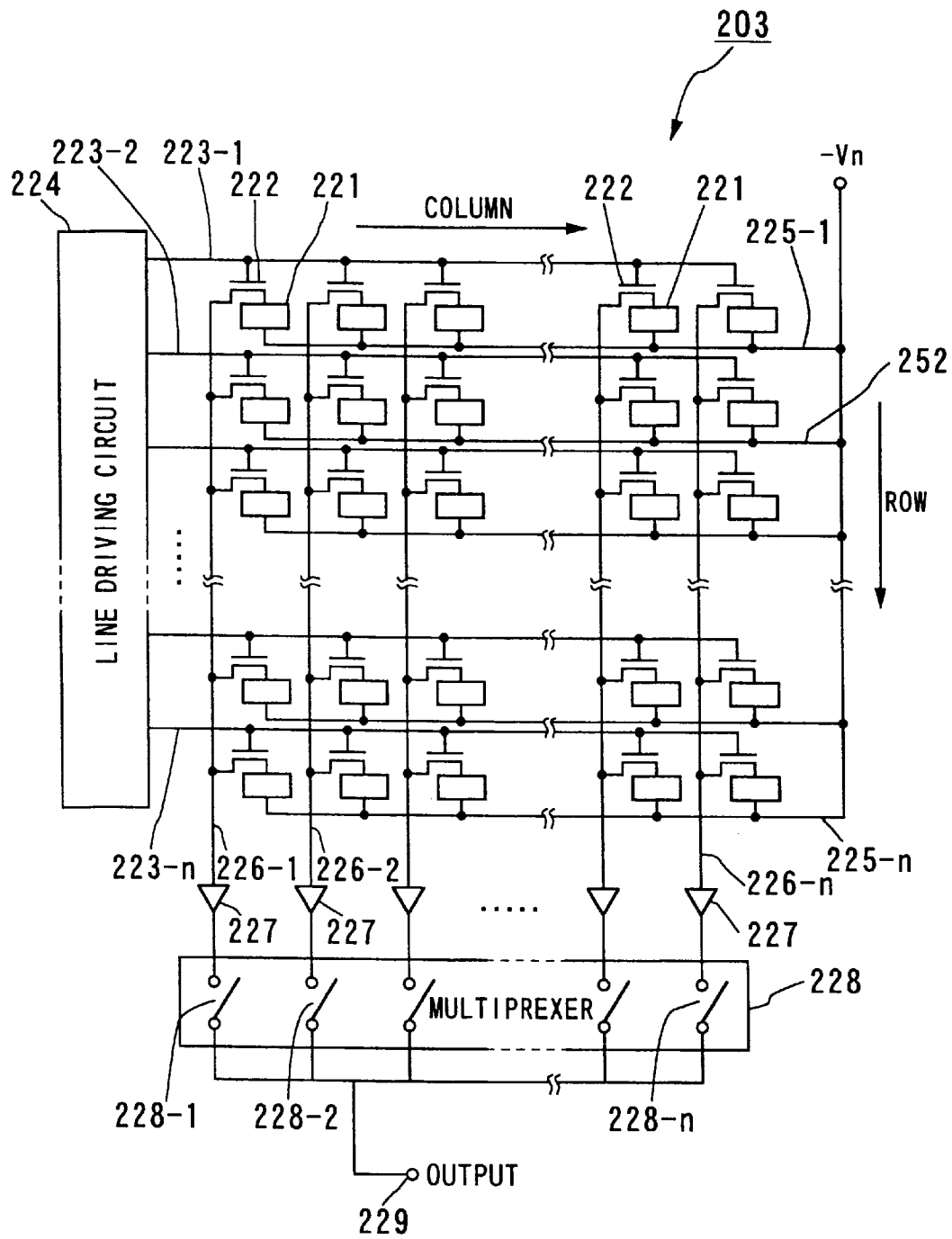
FIG. 72 is a schematic diagram showing a planar-type X-ray detector installed in the system.

The planar-type X-ray detector 203, which is formed into a size of, for example, 4000×4000 pixels in the column and row, comprises a plurality of pixels 221 and a plurality of solid X-ray sensitive elements as X-ray detecting elements, as shown in FIG. 72, both of which are two-dimensionally arranged in the column and row directions. Each of the pixels 21 produces electric charges depending on the amounts of received X-rays. Each solid X-ray sensitive element is comprised of a thin-film transistor (TFT) 222 which serves as a switch reading out electric charges stored in the pixel 221.

Each pixel 221, which converts X-rays to visible light using a later-described fluorescent member 248 in FIG. 73, comprises a photodiode sensing the visible light and producing electric charges according to its received amounts and a capacitor storing the electric charges produced by the photodiode.

A connecting point between the cathode terminal of the photodiode and one terminal of the capacitor is connected with a reversed-bias power source (−Vn) by way of power lines 225 (225-1, 225-2, . . . , 225-n). A connecting point between anode terminal of the photodiode and the other terminal of the capacitor is coupled with the source terminal of TFT 222.

The gate terminal of TFT 222 is connected to each read-out line 223 (223-1, 223-2, . . . , 223-n) in common for each row, and connected to each line output terminal of a line driving circuit 224. On one hand, the drain terminal of TFT 222 is connected to each transfer line 226 (226-1, 226-2, . . . , 226-n) in common for each column, and connected to each switch 228-1 (228-2, . . . , 228-n) of a multiplexer 228 via a read-out amplifier 227.

Figure 73:
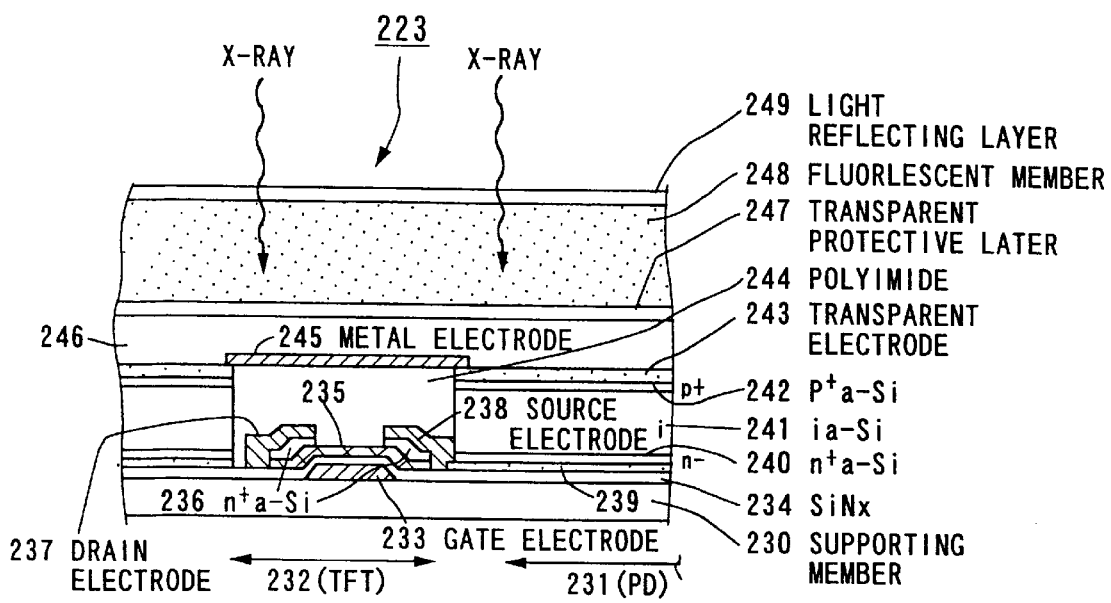
FIG. 73 is a partial cross section of a TFT region and pixel region of the planar-type X-ray detector.

Each X-ray detecting element, as shown in FIG. 73, is composed of a pixel region 231 (PD: corresponding to the pixel 221) and a TFT region 232 (corresponding to the TFT), both of which are formed on a supporting member 230. On the supporting member 230 is formed a gate electrode 233 of TFT 222, on which a SiNx layer 234 is laminated.

On the SiNx layer 234 in the TFT region 232, a polycrystalline silicone layer 235 (channel layer) is laminated, whose both ends shown in the drawing are constructed to have, via $n^+$a-Si layer 236, a drain and source electrodes 237 and 238 laminated thereon. The TFT region 232 is covered by a first polyimide layer 244 on which laminated is a metal electrode 245 which mutually connects transparent electrodes 243 of the pixel region 231.

On the SiNx layer 234 in the pixel region 231, a transparent electrode 239 coupled with the source electrode 238, $n^+$a-Si layer 240, ia-Si layer 241, $p^+$a-Si layer 242, and transparent electrode 243 are laminated in this order, which form the above-mentioned photodiode having a Pin structure.

On the metal electrode 245 in the TFT region 232 and the transparent electrode 243 in the pixel region 231, a second polyimide layer 246 is laminated, on which a transparent protective layer 247, fluorescent member 248, and light reflecting layer 248 are laminated successively.

The X-ray detector 203 thus-constructed takes in only X-rays, with visible light reflected thanks to the light reflecting layer 249. The accepted X-rays are converted to visible light by the fluorescent member 248. The converted visible light is received by the visible-light-sensitive pixel region (i.e., photodiode) and converted into corresponding electric charges, after having passed the transparent protective layer 247, the second polyimide layer 246, and the transparent electrode 243. The converted electric charges are then stored by the storing capacitor, and read out as imaging signals (data) pixel by pixel for each line through the reading-out line 223. The read images signals, which are proportional to energy of the detected X-rays, are provided to the A/D converter 207 shown in FIG. 68 via the multiplexers 228 and an output terminal 229.

Operation in Fluoroscopic/radiographic Mode

The operation in the fluoroscopic/radiographic mode of the X-ray diagnostic system will now be explained.

In this mode, an operator handles a system console to input such imaging conditions as a radiographic angle (fluoroscopic angle), the number of times of X-ray irradiation and its interval, a tube voltage, a detector rotating angle, and shrinking amounts for the shrinkable supporting member. Imaging condition data interpreted from the imaging conditions are sent from the imaging condition setting unit 208 and temporarily stored by the imaging condition memory 209. In response to input of the imaging angle (fluoroscopic angle) given by an operator, the imaging condition setting unit 208 sends it to the detector rotating mechanism 206B.

Figure 74:
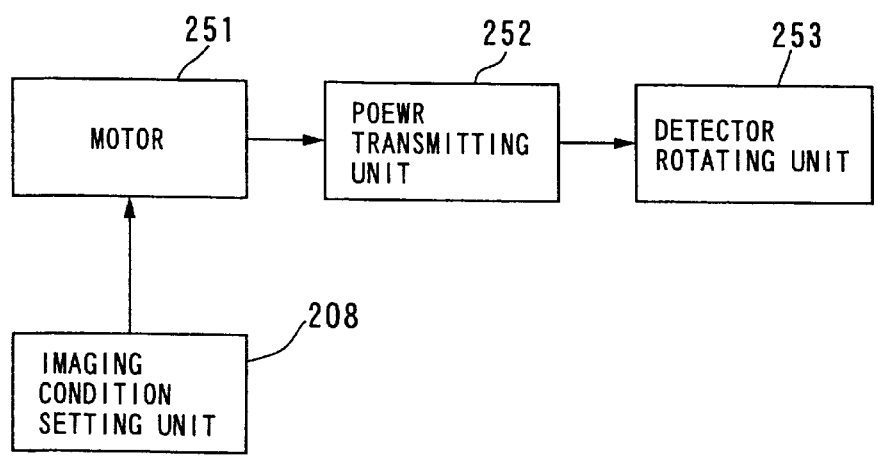
FIG. 74 is a block diagram of rotational driving system in the planar-type X-ray detector.

The detector rotating mechanism 206B is essentially constructed by having a power transmitting unit 252 and detector rotating unit 253, as shown in FIG. 74. When information of the detector rotating angle is supplied from the setting unit 208, a motor 251 begins to drive, and its rotating force is transmitted to the detector rotating mechanism 206B by way of the power transmitting unit 252. This permits angles to the shrinkable supporting member 206A and C-shaped arm 204 to be changed, according to the operator's operation. The detector rotating mechanism 206B is constructed, as shown in FIG. 80A, that it rotates the X-ray detector 203 about an axis parallel to the slide rotating axis of the C-shaped arm 204. Alternatively, as shown in FIG. 80B, the detector rotating mechanism may be constructed to rotate the X-ray detector 203 around an axis perpendicular to the slide rotating axis of the C-shaped arm. Still alternatively, the detector rotating mechanism may be formed to rotate the X-ray detector 203 using two axes perpendicular and parallel to the slide rotating axis of the C-shaped arm 204.

When an operator instructs the shrinkable supporting member 206A to increase or decrease its shrinking amounts, the imaging condition setting unit 208 drives a not-shown motor for the shrinkable supporting member to change its shrinking amounts.

After such rotation of the X-ray detector 203 has completed, X-ray irradiation is performed. In this irradiation, less amounts of continuous X-rays are used for fluoroscopy, while more amounts of pulsed X-rays are used for radiography. Information of an X-ray image formed by this irradiation is detected by the X-ray detector 203 which supplies it as analog imaging signals to the A/D converter 207. The converter 207 digitizes those signals and supplies them to the imaging memory 112, where the imaging signals are temporarily memorized.

In the case that the x-ray detector 203 are always directed toward the X-ray focus, as in the conventional way, the distance between the X-ray focus and the X-ray detector 203 is almost the same at any position existing on its detection surface. In contrast, as described before, if the X-ray detector 203 is always rotationally-driven to be directed along the vertical direction, X-rays are irradiated obliquely to the X-ray detector 203. This causes larger differences in the distances to the X-ray focus, depending to the spatial positions of the detector surface, which sometimes affects image quality.

To avoid such situation, the geometry converting unit 213 operates such that it perform a trapezoidal conversion on the imaging signals memorized by the imaging memory 212 in accordance with imaging angle information memorized by the imaging condition memory 209. Specifically, the geometry converting unit 213 obtains a trapezoidal region in the detection surface of the detector 203, onto which X-rays are irradiated, from imaging position information (imaging angle information and shrinking amounts of the shrinkable supporting member) memorized by the imaging condition memory 209, and then converts the image data residing within the trapezoidal region into those in a rectangular shape. Thus differences in distance from each position on the X-ray detector surface to the X-ray focus can be corrected, preventing images from being affected by drawbacks caused owing to the distance differences.

Next, using affine conversion processes (geometrical conversion processes), the affine converting unit 214 converts each coordinate and corrects their distortions by performing processes such as image scaling-up and scaling-down, reversed, and/or parallel movement on the imaging signals trapezoidal-converted. By the edge emphasizing unit 15, edges of radiographed images are emphasized through high-pass filters such as Laplacian (secondary differential operator). Then, by the gradation converting unit 216, the coordinate-converted imaging signals are subject to correction of gradations (density correction) such as contrast levels and brightness degrees, and sent to the D/A converter 210. By this converter 210, the imaging signals which have been subject to various processes in digital quantities are converted to corresponding analog imaging signals, and then supplied to, for example, the display 211. In consequence, fluoroscopic or radiographic images of desired regions within a subject can be displayed. Further, in performing digital tomography and three dimensional reconstruction, a calculation time can be shortened, because non-linear processes can be omitted. Still further, since the detector rotating mechanism 206B is capable of rotating the detector's angle when deeper-angle imaging is performed, more deeper imaging angles than in the conventional system can be realized.

Construction for Subtraction Imaging Mode

Figure 70:
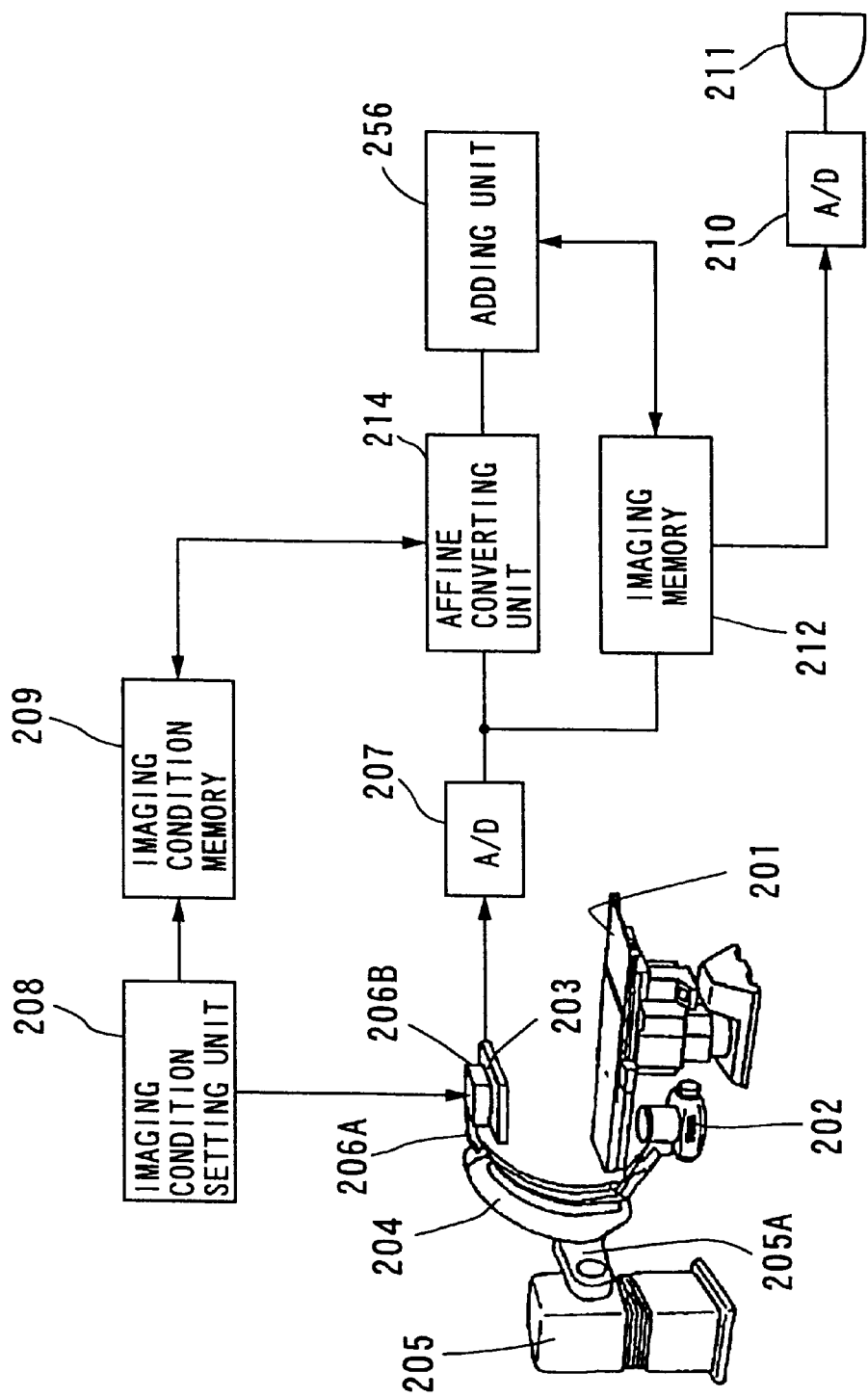
FIG. 70 is a schematic diagram of the X-ray diagnostic system, which corresponds to its tomography mode in the third embodiment.

For the subtraction imaging mode, the X-ray diagnostic system is constructed, as shown in FIG. 70, in addition to the foregoing couch 1 to graduation converting unit 16, to have a subtracting unit 255 which subtracts, from live images supplied from the A/D converter 207, a masking image previously memorized in the imaging memory 212.

Operation in Subtraction Imaging Mode

In this mode, first, radiography is executed for a subject into which contrast medium has not been injected. Imaging information acquired in this first radiography is one stored as masking image data into the imaging memory 212. Then radiography is executed for the contrast-medium-injected subject, which provides image information as live image data to the imaging memory 212 temporarily memorized therein.

The subtracting unit 255 reads out both live image data and corresponding masking image data from the imaging memory 212, and put both the data under the subtraction process to subtraction images. Specifically, with the acquired live image data saved in the memory, the unit 255 subtracts the masking image data from the live image data pixel by pixel.

The subtraction image data are then subject to the trapezoidal conversion, affine conversion, edge emphasizing process, and gradation conversion by the foregoing various units 213 to 216, respectively, and further analyzed by the D/A converter 210 to supply them to the display 211. By this method, subtraction images distinguishing a desired object such as a blood vessel from the entire image can be displayed by the display 211. Additionally, because driving the detector rotating mechanism 206B permits the detector to be rotated, imaging angles deeper than the conventional system can readily be provided for deeper-angle imaging.

Construction for Tomography Mode

The construction of the X-ray diagnostic system for this tomography mode is that, as shown in FIG. 70, in addition to the couch 201 to imaging memory 212 and affine converting unit 214, there is provided an adding unit 256 adding imaging signals from a desired tomographic cross section. This permits angles to the shrinkable supporting member 206A and C-shaped arm204 to be changed, according to the operator's operation. The detector rotating mechanism 206B is constructed, as shown in FIG. 80A, that is rotates the X-ray detector 203 about an axis parallel to the slide rotating axis of the C-shaped arm 204. Alternatively, as shown in FIG. 80B, the detector rotating mechanism may be constructed to rotate the X-ray detector 203 around an axis perpendicular to the slide rotating axis of the C-shaped arm. Still alternatively, the detector rotating mechanism may be formed to rotate the X-ray detector 203 using two axes perpendicular and parallel to the slide rotating axis of the C-shaped arm 204.

When an operator instructs the shrinkable supporting member 206A to increase or decrease shrinking amounts, the imaging condition setting unit 208 drives a not-shown motor for the shrinkable supporting member to change its shrinking amounts.

Operation in Tomography Mode

In this mode, the C-shaped arm 204 is, for instance, rotationally controlled within angle range of −20 to +20 degrees, and image data acquired during this radiography are temporarily stored in the imaging memory 212. When this acquisition has been completed, an arbitrary cross section is specified via not-shown setting means. By the affine converting unit 214, affine conversion processes are performed on image data read out from the imaging memory 212, the affine conversion processes being set to match with scaling-up and -down ratios and shift amounts of each acquired image which can be focused on the specified cross section. And converted image data are sent to the adding unit 256. By the adding unit 256, the affine-converted image data are added to each other to form tomogram data of the specified cross section. The tomogram data are sent via the DIA converter 210 to the display 211, providing a tomogram at any slice position. This permits the C-shaped arm type X-ray diagnostic system for cardiovascular system to obtain tomograms in a relatively higher speed.

Construction for Reconstruction Mode

Figure 71:
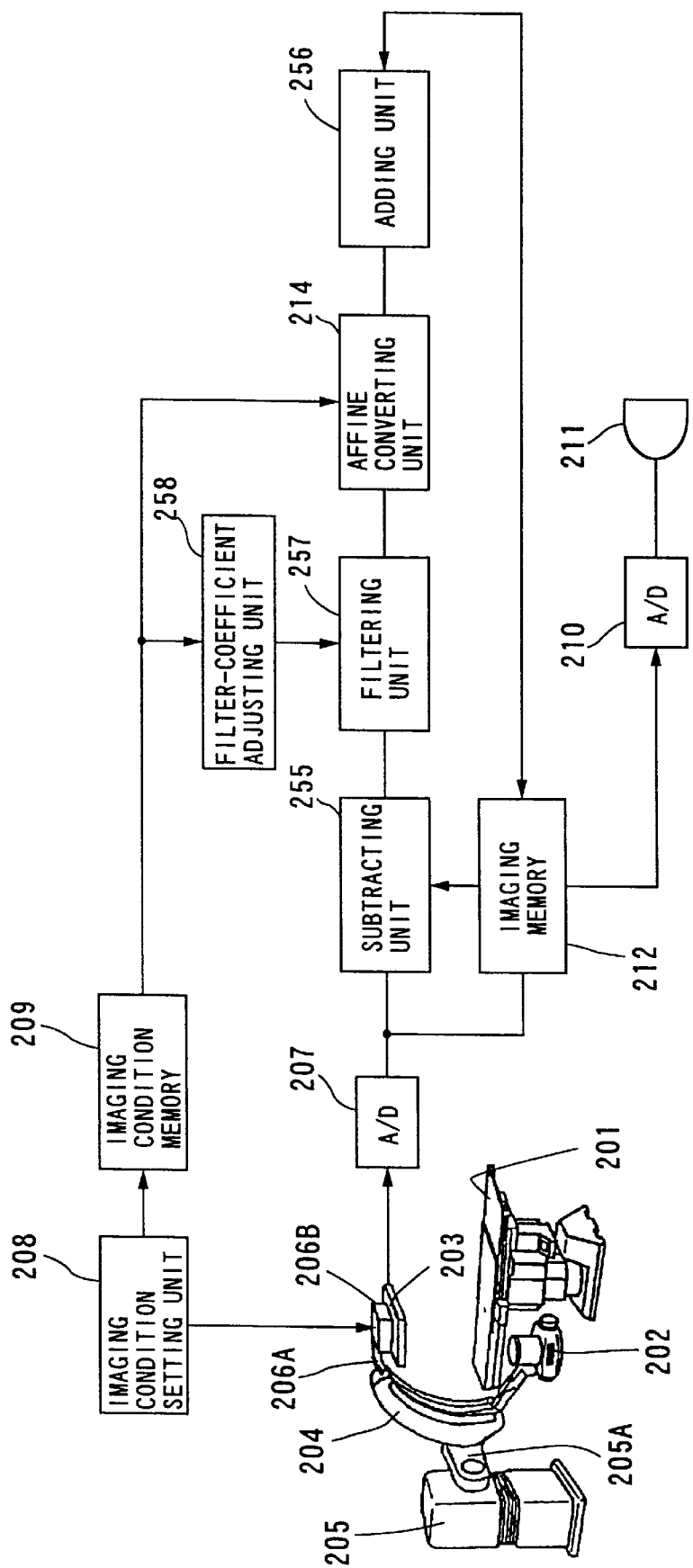
FIG. 71 is a schematic diagram of the X-ray diagnostic system, which corresponds to its recombination mode of subtraction images, in the third embodiment.

For the reconstruction mode, the construction of the X-ray diagnostic system is composed of having a construction that, as shown in FIG. 71, besides the foregoing couch 201 to imaging memory 212 and affine converting unit 214, there are provided a filtering unit 257 performing specified filtering processes (such as a convolution filtering process) on the image signals read from the imaging memory 212, and a filter-coefficient controlling unit 258 adjustably controlling filter-coefficients in the filtering unit 257 according to image angle information memorized in the imaging condition memory 209.

Operation in Reconstruction Mode

Figure 75:
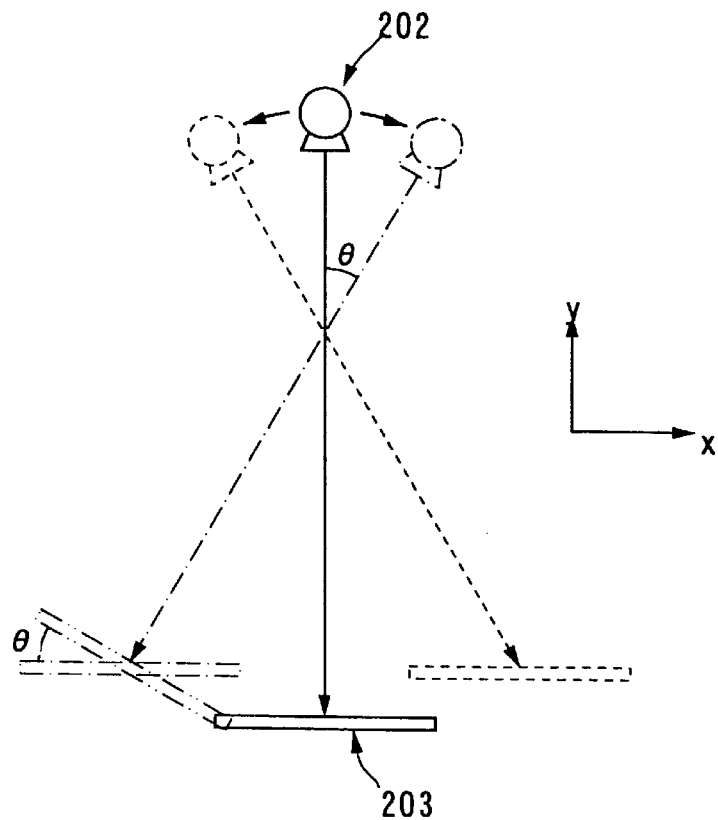
FIG. 75 shows driven states of the X-ray planar-type detector driven by the rotational driving system.
Figure 76:
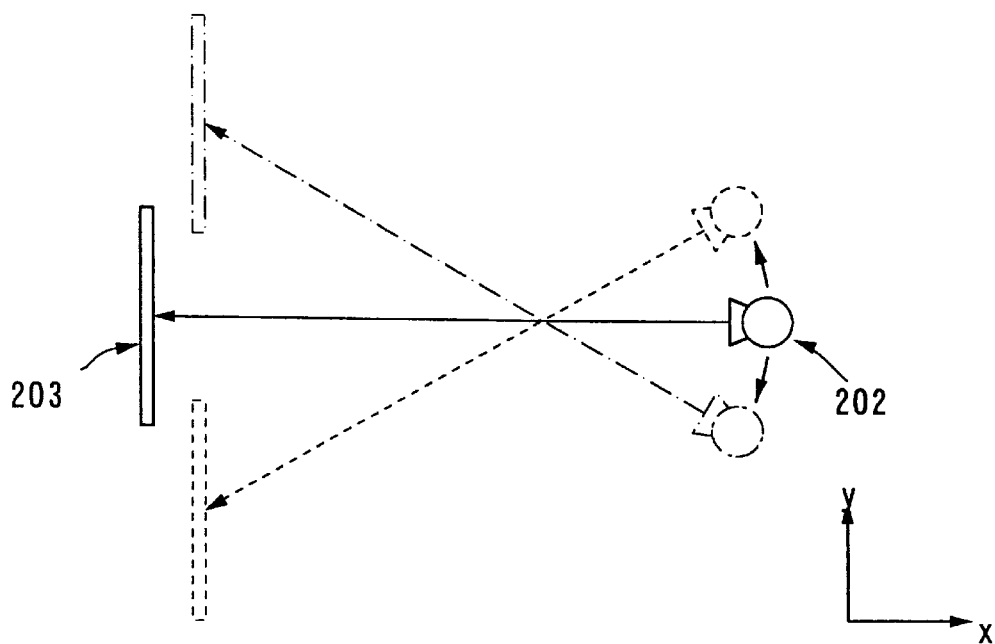
FIG. 76 shows other driven states of the X-ray planar-type detector driven by the rotational driving system.

For performing three dimensional reconstruction imaging, the principle of the three dimensional reconstruction requires image information from at least a view range of 180 degrees. Thus, in this embodiment, because the X-ray diagnostic system is constructed in the signal plane type, as described before, during a first view range of 90 degrees, radiography is executed by rotationally driving the X-ray detector as shown in FIG. 75. If radiography is intended to be executed at angles more than 90 degrees in this situation, the angle of the X-ray detector to the X-ray focusing direction becomes too deep to cover by the detector all X-ray beams transmitting a patient's objective region. To avoid this, on completing the first radiography for the first view range of 90 degrees, the angle of the X-ray detector 203 is rotated by 90 degrees, as shown in FIG. 76, and the X-ray detector 203 is constantly controlled to be directed along a direction perpendicular the vertical direction, regardless of the rotation angles of the C-shaped arm 204, like in the first view range of 90 degrees. This rotation provides image information for a view range of 180 degrees necessary for three dimensional reconstruction.

On one hand, the rotation of the X-ray detector 203 is extremely slower in speed than image information acquisition. Thus, for image signals acquired until the detector's detecting surface has been moved to its vertical position (for example, image signals acquired during a transition period from the position shown in FIG. 75 to that in FIG. 76), because the detecting surface and a desired cross section are not parallel with each other, it is possible that those image data are once projected onto a parallel plane to the cross section, and used for reconstruction. Alternatively, it may also possible that those image data are not used.

The reconstruction mode is composed of a first mode performing a subtraction process between radiographic images and a null image, and a second mode performing a subtraction process between live images and a masking image.

Mode for Subtraction Between Radiographic Image and Null Image

In performing this mode of imaging, in advance of the main scan, scanning is performed with nothing on the couch 1. This scanning provides data of a null image representing unevenness degrees of densities (detected signal intensities) of the X-ray detecting elements of the detector 203, which are stored in the imaging memory 212.

In the next stage, as described before, the C-shaped arm 204 are rotated over a view range of 180 degrees to obtain image information as radiographic image data for each view angle, those image data being stored in the imaging memory 212. By the subtracting unit 255, subtraction is performed between the null image data and radiographic image data both of which have been stored in the imaging memory 212. The resultant subtraction image are supplied to the filtering unit 257.

The filtering unit 257 performs, by way of example, performs three dimensional reconstruction through a filtered backprojection method. A filtering process is thus performed, using a properly-selected convolution filter such as "Shepp & Logan" or "Romanchandran", on the subtraction image data. However, in this system, the detector's surface are always controlled to be parallel with a cross section formed by an array of pixels of an imaging region, during which time image information is acquired. Performing a filtering process using the same convolution filter even if projection angles change causes artifacts, because the filtering width substantially changes depending on the angles (i.e., as the detector's rotation angle becomes deeper and deeper, the filtering width for the convolution filter, when being backprojected, becomes small).

Therefore, the filter-coefficient controlling unit 258 reads out from the imaging condition memory 209 imaging angle information representing imaging angles associated with a subtraction image, and according to the imaging angles, adjustably controls filter functions (filter-coefficients) of the filtering unit 257. In detail, the filter-coefficient controlling unit 258 sets the following filter function q1 in the filtering unit 257. The filter function q1 changes responsively to the imaging angle.

$$Q1(t)=q(\cos \theta t)$$

where q(t) denotes the filter function of the filtering unit 257 and θ denotes the imaging angle.

Figure 77:
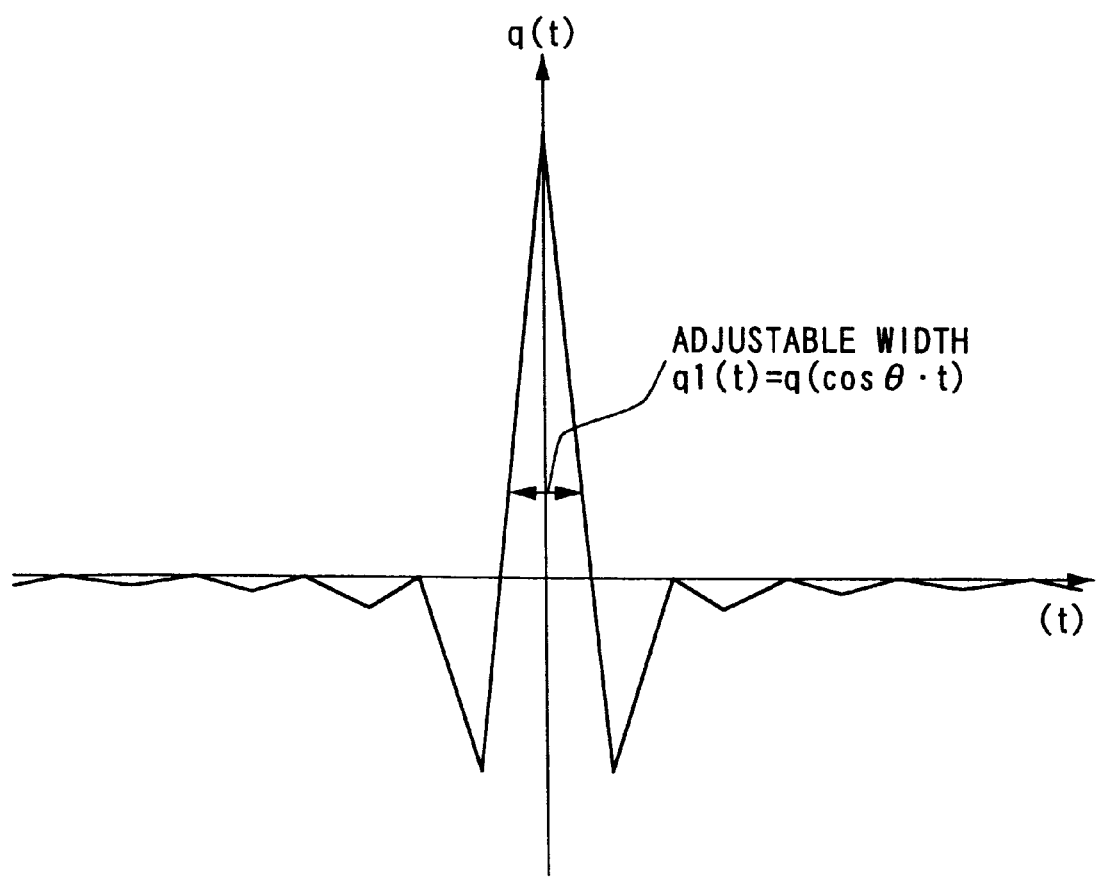
FIG. 77 is a filtering characteristics of a convolution filter of which filtering width is controllable in agreement with rotational agreements of the planar-type X-ray detector.

This setting allows the filtering width of the convolution filter to adjustably be set to optimum values depending on rotation angles of the detector, as shown in FIG. 77, avoiding the generation of artifacts in three dimensional reconstructed images.

Data of subtraction images thus filtering-processed are sent to the imaging memory 212, and read out by the affine converting unit 214. By the unit 214, affine conversion processes are performed on image data read out from the imaging memory 212, the affine conversion processes being set to match with scaling-up and -down ratios and shift amounts of each acquired image which can be focused on the operator-specifying section. And converted image data are sent to the adding unit 256.

Figure 78:
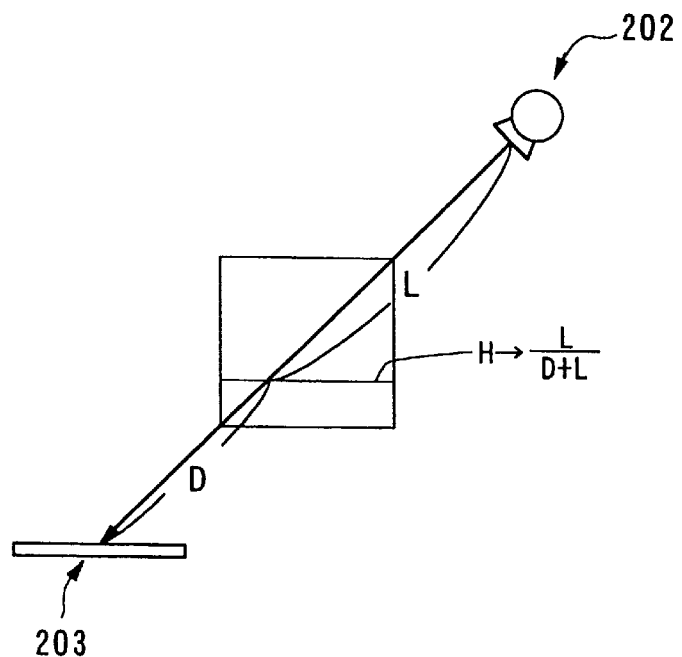
FIG. 78 explains the coincidence between a pixel sample point in a three dimensional recombination region and a sample point in the planar-type X-ray detector.

In the adding unit 256, data of subtraction images thus affine-converted are added (reversely projected) to produce a reconstructed image of the specified cross section. Specifically, as illustrated in FIG. 78, where it is assumed a desired cross section in an imaging region is H, the distance from the cross section to the detection surface of the detector 203 is D, and the distance from the cross section to the focus of the X-ray generator 202 is L, the adding unit 256 adds a subtraction image multiplied by "L/(D+L)" to the desired cross section H to form a reconstructed image of the cross section. This reconstructed image data are then sent to the display 211 via the D/A converter 210. As a result, the present X-ray diagnostic system is capable of performing a subtraction process between radiographic images and a null image and displaying a resultant reconstructed image for any position on the display 211, even if this system is based on a plain diagnostic system which has been used so far.

A reconstructing region (i.e., imaging region) is defined by a cylinder interior-dividing a flux of X-rays oriented to all of the directions from the X-ray generator 202. Since the pixels existing within the cylinder are three-dimensionally made to be discrete by a length at the center of the reconstructing region, at which is projected into the width of a single X-ray detecting element of the detector 203, a reconstructed image of data at the discrete points needs to be obtained. This discretion interval is just one example, and it sometimes differs depending on manufactures or systems; it is basically enough that a discretion interval defined by each system is used.

Mode for Subtraction Between Live Images and Masking Images

In this mode, first, radiography is executed for a subject into which contrast medium has not been injected. Imaging information acquired in this first radiography is once stored as masking image data into the imaging memory 212. Then radiography is executed for the contrast-medium-injected subject, which provides image information as live image data to the imaging memory 212 temporarily memorized therein.

When the masking image data and live image data acquired as image information before and after the injection of contrast medium have been loaded into the imaging memory 212, the subtracting unit 255 performs a subtraction process on both data, and supplies the resultant subtraction image data to the filtering unit 257. The filter-coefficients in this unit 257 are optimally controlled by the filter-coefficient controlling unit 258 in agreement with the imaging angles, as described before. The unit 257 performs, therefore, a filtering process for the subtraction image data using the controlled filter-coefficients, and supplies their results to the affine converting unit 214.

By the affine converting unit 214, affine conversion processes are performed on subtraction image data read out from the imaging memory 212, the affine conversion processes being set to match with scaling-up and -down ratios and shift amounts of each acquired image which can be focused on the specified cross section. And converted subtraction image data are sent to the adding unit 256. By the adding unit 256, the affine-converted subtraction image data are added to each other to form tomogram data of a specified cross section. The tomogram data are sent via the D/A converter 210 to the display 211, providing a tomogram at any slice position. As a result, the present X-ray diagnostic system is capable of performing a subtraction process between live images and a masking image and displaying a resultant reconstructed image at any position on the display 211, even if this system is based on a plain diagnostic system which has been used so far.

As understood from the above, in the X-ray diagnostic system of the third embodiment, regardless of the rotation angles of the C-shaped arm 204, the X-ray detector 203 is rotationally-driven so that it becomes parallel with cross sections along arrays of pixels in a reconstructing region, and the incidence angles of X-rays are adjusted. Therefore, only this system by itself makes it possible to perform imaging in a variety of modes consisting of the "fluoroscopic/radiographic mode", "subtraction imaging mode", "tomography mode", and "reconstruction mode".

Figure 79:
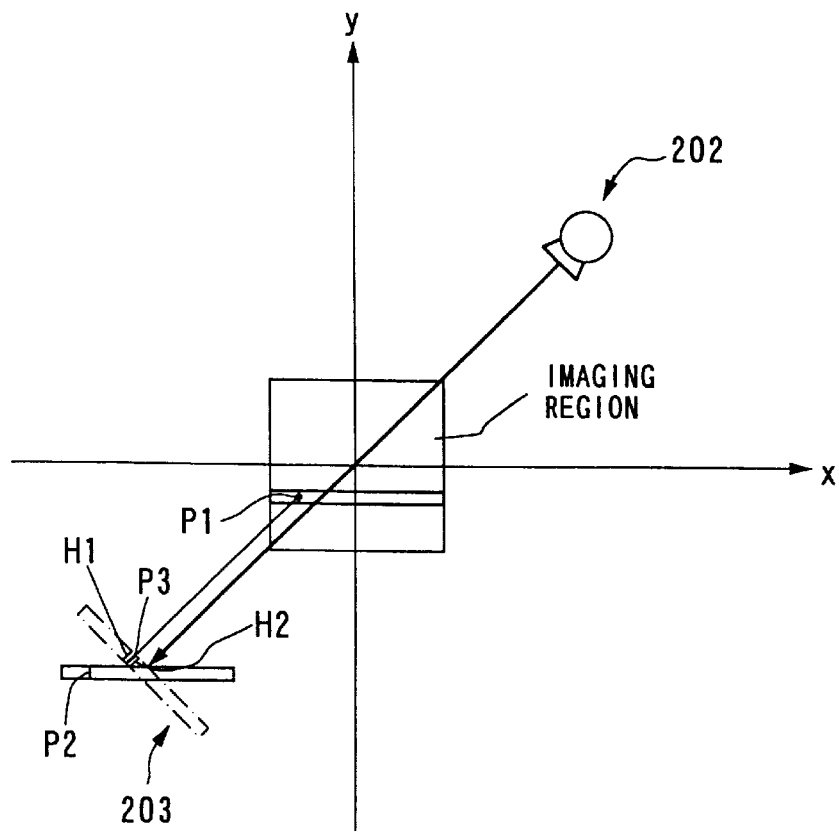
FIG. 79 explains an addition process of pixels in producing a recombination image by the X-ray diagnostic system in the third embodiment.

If the system does not use the detector rotating mechanism 206B, the addition carried out by the adding unit 256 becomes equivalent to a process which adds in each plane parallel with the detection surface with images scaled down (or up). Since a three dimensional cross section is defined discretely, there is only a less possibility that, as shown in FIG. 79, each point H1, H2, . . . , Hn in the detection surface corresponds to a discrete point P1 in the three-dimensional cross section. Thus, if the detector rotating mechanism 206B would not be used, it is necessary to interpolate a point P3 corresponding to the discrete point P1 using the points H1 and H2, and the like, which leads to a useless calculation. In contrast, since the system employs the detector rotating mechanism 206B, the detector's detecting surface is parallel-moved against the three dimensional cross section, as shown by the solid line in FIG. 79. Consequently, the reverse projection calculation can be accomplished by, as shown in FIG. 71, the affine converting unit 214 and adding unit 15. This provides a shortened time image processing, because of being able to use affine conversion processes of less amounts of calculation, instead of using non-linear conversion processes. Additionally, a versatile affine conversion board can be used, providing less cost together with a high-speed calculation.

Fourth Embodiment

A fourth embodiment of the present invention will now be explained.

The X-ray diagnostic system in the third embodiment has been formed into a single-plane type, while an X-ray diagnostic system in the fourth embodiment is applied to a bi-plane type.

In the system of this embodiment, like the third embodiment, the planar-type X-ray detector 203 is rotated depending on the angles of the C-shaped arm rotated, during which rotation image information is acquired. To accomplish the three dimensional reconstruction, image information should be acquired over a view range of 90 degrees or more (in principle, 180 degrees or more). For this reason, in this system, the first plane is controllably rotated over a first view range of 90 degrees as in FIG. 75, while the second plane is controllably rotated over a second view range of 90 degrees which compensates the first view range, as shown in FIG. 76. This rotation of the bi-planes make it possible to acquire image information over a view range of 90 degrees or more. A projection angle realized by each rotating arm for the planes is changed, for example, by one degree for repeated scanning, thereby acquiring, by way of example, X-ray intensity distribution data of 180 patterns corresponding to rotation angles of 180 degrees, and reconstructing those acquired data three-dimensionally.

Accordingly, tomograms can be obtained by the X-shaped arm type of X-ray diagnostic system constructed for cardiovascular systems. Additionally, it is not necessary to take account of a time lag from the completion of the first scanning to the arrival at a starting position at which the second scanning begins (i.e., the time lag from the position shown in FIG. 75 to that in FIG. 76).

Fifth Embodiment

A fifth embodiment of the present invention will now be explained.

In this embodiment, an X-ray diagnostic system according to the present invention uses a synchrotron as means for generating X-rays. The system is constructed to obtain images enlarged by desires ratios by detecting X-rays emanating from the synchrotron using the planar-type X-ray detector 203 of which angle for receiving the X-rays are adjusted.

The synchrotron is an apparatus which generates monochromatic and parallel X-rays and has been highly spotlighted. At present, there is known an image intensifier (I.I.)/TV system as the most practical detection system acquiring in real time X-ray dynamic images. If the planar-type X-ray detector 203 is used as the detection system without any measures, instead of the I.I./TV system, there arises a disadvantage that an enlargement process associated with the TV system cannot be done, through there are provided some advantages that an MTF (Spatial resolution) is high, image distortions are less, and the like.

Figure 81:
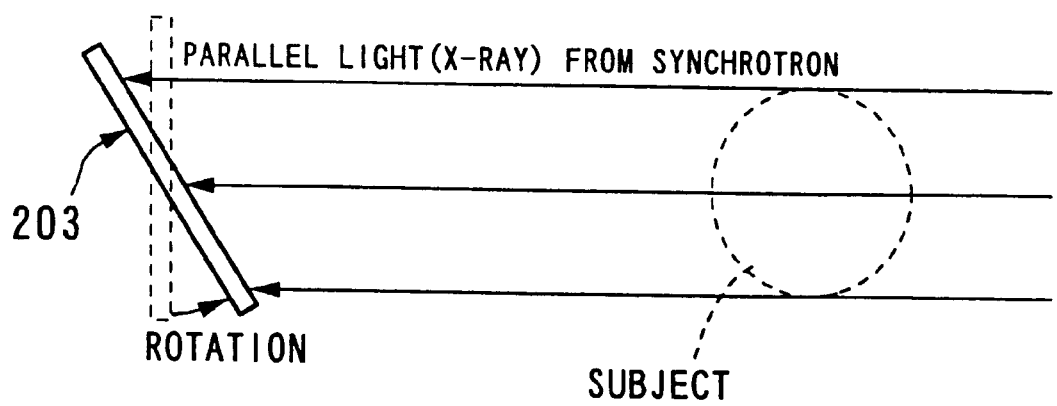
FIG. 81 is an illustration an enlargement imaging method using parallel light beams emanated from a synchrotron, which is executed in an X-ray diagnostic system according to a fifth embodiment of the present invention.

Hence, in this X-ray diagnostic system, as shown in FIG. 81, by using the detector rotating mechanism 206A, the planar-type X-ray detector 203 is adjusted in the incidence angle of the X-rays being generated from the synchrotron such that images can be enlarged by any ratios. In addition to the similar advantages obtained in the third embodiment, this construction make it possible to enlarge images by desired ratios.

In this fifth embodiment, for the sake of an easier understanding, though the explanation has been given to easier one of the longitudinal or lateral direction of the detector, an image can be acquired which is enlarged in its diagonal line direction by rotating the X-ray detector about its diagonal line axis.

Additionally, the longitudinal and lateral sizes of an image are generally the same, however images obtained in this embodiment have finer pixel pitches in one direction. To avoid this inconvenience, the images can be enlarged in the remaining one direction by image processing based on the digital zooming technique.

For the sake of completeness it should be mentioned that the embodiment examples shown in the figures are not definitive lists of possible embodiments. The expert will appreciate that it is possible to combine the various construction details or to supplement or modify them by measures known from the prior art without departing from the basic inventive principle.

What we claim is:

1. An X-ray diagnostic system comprising:
   an X-ray generator configured to irradiate an X-ray through a subject to be imaged;
   a planar-type X-ray detector configured to receive the X-ray which has passed through the subject and to convert the received X-ray into electric two-dimensional imaging signals;
   supporting means for supporting the X-ray detector;
   incidence angle adjusting means, arranged between the X-ray detector and the supporting means, for adjusting an incidence angle of the X-ray upon the X-ray detector view by view by rotationally driving the X-ray detector; and
   image processing means for producing an X-ray tomogram of the subject by performing image processing on the imaging signals obtained at each view.

2. The system of claim 1, wherein the supporting means comprises:
   a C-shaped arm of which a one end supports the X-ray generator and of which an other end angle-adjustably supports the X-ray detector;

an arm holder configured to support the C-shaped arm slidably and rotatably; and a holder supporting mechanism configured to rotatably support the arm holder.

3. The system of claim 1, wherein the image processing means is constructed to convert, view by view, data from the X-ray that has passed through a trapezoidal region defined by the incidence angle of the X-ray on the X-ray detector into rectangular image data, and to obtain the X-ray tomogram on the basis of the plurality of rectangular image data.

4. The system of claim 3, wherein the supporting means comprises:

a C-shaped arm having one end which supports the X-ray generator and an other end which angle-adjustably supports the X-ray detector;

an arm holder configured to support the C-shaped arm slidably and rotatably; and a holder supporting mechanism configured to rotatably support the arm holder.

5. The system of claim 1, wherein the supporting means comprises:

a C-shaped arm configured to support the X-ray generator and the X-ray detector at both ends;

sliding/supporting means slidably and rotatably supporting the C-shaped arm; and rotatably supporting means rotatably supporting the sliding/supporting means, wherein the incidence angle adjusting means is arranged between the C-shaped arm and the X-ray detector.

6. The system of claim 5, wherein the image processing means is constructed to obtain, view by view, a trapezoidal region through which the X-ray irradiated to the X-ray detector passes on the basis of the incidence angle of the X-ray, to convert, view by view, data from the X-ray that has passed through the trapezoidal region into rectangular image data, and to produce the X-ray tomogram on the basis of the plurality of rectangular image data in relation to each respective view.

7. An X-ray diagnostic system comprising:

an X-ray generator configured to irradiate an X-ray through a subject to be imaged;

a planar X-ray detector configured to detect the X-ray which has passed through the subject;

a C-shaped arm of which a one end supports the X-ray generator and of which an other end angle-adjustably supports the X-ray detector;

an arm holder configured to slidably and rotatably support the C-shaped arm; and a holder supporting mechanism configured to rotatably support the arm holder.

8. The X-ray diagnostic system of claim 1, further comprising:

moving means for moving at least one of the X-ray generator and the X-ray detector so that a spatial position of the at least one of the X-ray generator and the X-ray detector is changed relatively to the subject, view by view; and means for obtaining a relative positional relationship between the X-ray generator and the X-ray detector for each view, wherein the image processing means includes:

means for setting a three-dimensional ROI that includes the subject;

means for obtaining a plurality of three-dimensional coordinates of pixels included in the ROI; and means for obtaining, as data of the X-ray tomogram, a pixel value of each of the three-dimensional coordinates on the basis of the two-dimensional imaging signals detected view by view and the relative positional relationship obtained view by view.

9. The X-ray diagnostic system of claim 8, wherein the three-dimensional coordinate pixel value obtaining means comprises:

means for obtaining, view by view, two-dimensional coordinates of signals selected from the two-dimensional imaging signals; and means for producing the pixel values of the three-dimensional coordinates by extracting, view by view, the corresponding signals of the two-dimensional coordinates from the detected two-dimensional imaging signals and adding the extracted data of each view to each other.

10. The system of claim 9, wherein the setting means is constructed to set, as the ROI, a planar cross section of the subject, of which inclination relative to the subject is changeable.

11. The system of claim 9, wherein the setting means is constructed to set, as the ROI, a curved cross section of the subject.

12. An X-ray diagnostic system comprising:

an X-ray generator configured to irradiate an X-ray through a subject to be imaged;

a two-dimensional X-ray detector having a curved detecting plane onto which the X-ray impinges, configured to detect the X-ray which has passed through the subject with the curved detecting plane and to output two-dimensional imaging signals corresponding to the detected X-ray;

supporting/moving means for movably supporting the X-ray generator and the X-ray detector; and image processing means for converting the two-dimensional imaging signals detected through the curved detecting plane into two-dimensional signals of a planar plane that constitutes a tomogram of the subject.

13. An X-ray diagnostic system comprising:

a two-dimensional X-ray detector configured to detect an X-ray passing through a subject to be imaged and configured to output two-dimensional imaging signals corresponding to the detected X-ray; and supporting means for detachably supporting the two-dimensional detector, wherein the two-dimensional X-ray detector comprises a plurality of X-ray detectors whose characteristics are different from each other, and the supporting means is constructed to exchangeably support the plurality of X-ray detectors.

14. The X-ray diagnostic system of claim 1, further comprising:

moving means for moving at least one of the X-ray generator and the X-ray detector so that a spatial position of the at least one of the X-ray generator and the X-ray detector is changed relatively to the subject, view by view, wherein the image processing means comprises:

means for obtaining a set of three-dimensional volume data by obtaining a plurality of tomograms on the basis of a plurality of sets of the two-dimensional imaging signals detected at each view;

means for performing a filtering process to remove blur components from the three-dimensional volume data; and means for obtaining the X-ray tomogram of the subject by performing image processing on the filtered data.

15. An X-ray diagnostic system of claim 13, further comprising:
   means for measuring an electrocardiograph signal of the subject; and
   means for obtaining a tomogram of the subject on the basis of a plurality of sets of the two-dimensional imaging signals detected view by view when the electrocardiograph signal coincides with given timing points.

16. An X-ray diagnostic system comprising:
   a couch configured to movably support a tabletop on which a subject to be imaged is laid;
   an X-ray generator that has an X-ray focus and is configured to irradiate an X-ray through the subject;
   a planar X-ray detector configured to detect the X-ray which has passed through the subject and configured to output two-dimensional imaging signals based on the detected X-ray;
   supporting means for supporting the X-ray generator and the X-ray detector;
   driving means for moving, view by view, at least one of spatial positions of the X-ray focus and the tabletop, thereby changing a relative spatial positional relationship between the X-ray focus and the subject;
   calculating means for calculating the relative spatial positional relationship between the X-ray focus and the X-ray detector for each view;
   processing means for obtaining a tomogram of the subject using the two-dimensional imaging signals detected view by view and the relative spatial positional relationship for each view,
   wherein the supporting means comprises;
   a C-shaped arm of which a one end supports the X-ray generator and of which an other end angle-adjustably supports the X-ray detector,
   an arm holder configured to slidably and rotatably support the C-shaped arm, and
   a holder supporting mechanism configured to rotatably support the arm holder.

17. An X-ray diagnostic system of claim 16, wherein the processing means includes:
   means for setting a plane that includes the subject, the tomogram being formed along the plane and an inclination of the plane to the subject being changeable;
   means for determining coordinates contained in the plane; and
   means for obtaining, as the tomogram, image information about the coordinates using the two-dimensional imaging signals detected view by view and the relative spatial positional relationship calculated for each view.

18. An X-ray diagnostic system of claim 16, wherein the processing means includes:
   means for setting a curved plane that includes the subject, the tomogram being formed along the curved plane;
   means for determining coordinates contained in the curved plane; and
   means for obtaining, as the tomogram, image information about the coordinates using the two-dimensional imaging signals detected view by view and the relative spatial positional relationship calculated for each view.

19. An X-ray diagnostic system of claim 16, wherein the supporting means comprises:
   a first means for supporting the X-ray generator; and
   a second means for supporting the X-ray detector, the first and second supporting means being separable and the second supporting means being portable.

20. An X-ray diagnostic system of claim 14, wherein the means for performing a filtering process comprises a three-dimensionally isotropic filter configured to remove the blur components.

21. An X-ray diagnostic system of claim 14, wherein the means for performing a filtering process comprises a three-dimensionally anisotropic filter configured to remove the blur components.

22. An X-ray diagnostic system of claim 20, wherein the filtering process is performed along each of a plurality of paths of the X-ray.

23. An X-ray diagnostic system of claim 20, wherein the filtering process is performed along a representative of a plurality of paths of the X-ray.

* * * * *

UNITED STATES PATENT AND TRADEMARK OFFICE
CERTIFICATE OF CORRECTION

PATENT NO. : 6,196,715 B1
DATED : March 6, 2001
INVENTOR(S) : Kyojiro Nambu, et al.

It is certified that error appears in the above-identified patent and that said Letters Patent is hereby corrected as shown below:

<u>Title page,</u>
Item [30], the Foreign Application Priority Data is incorrect.
Item [30] should read:

-- [30] Foreign Application Priority Data

Apr. 25, 1997 [JP].................................9-109642 --

Signed and Sealed this

Twenty-fifth Day of September, 2001

Attest:

*Attesting Officer*

NICHOLAS P. GODICI
*Acting Director of the United States Patent and Trademark Office*